(12) United States Patent
Aronin et al.

(10) Patent No.: US 7,947,658 B2
(45) Date of Patent: May 24, 2011

(54) RNA INTERFERENCE FOR THE TREATMENT OF GAIN-OF-FUNCTION DISORDERS

(75) Inventors: Neil Aronin, Newtonville, MA (US); Phillip D. Zamore, Northboro, MA (US)

(73) Assignee: University of Massachusetts, Boston, MA (US)

( * ) Notice: Subject to any disclaimer, the term of this patent is extended or adjusted under 35 U.S.C. 154(b) by 578 days.

(21) Appl. No.: 10/571,705

(22) PCT Filed: Sep. 13, 2004

(86) PCT No.: PCT/US2004/029968
§ 371 (c)(1),
(2), (4) Date: Dec. 9, 2008

(87) PCT Pub. No.: WO2005/027980
PCT Pub. Date: Mar. 31, 2005

(65) Prior Publication Data
US 2009/0118206 A1 May 7, 2009

Related U.S. Application Data

(60) Provisional application No. 60/502,678, filed on Sep. 12, 2003.

(51) Int. Cl.
*A61K 48/00* (2006.01)
*C07H 21/02* (2006.01)
*C07H 21/04* (2006.01)

(52) U.S. Cl. .................... 514/44; 536/23.1; 536/24.5

(58) Field of Classification Search .................. None
See application file for complete search history.

(56) References Cited

U.S. PATENT DOCUMENTS

| | | | |
|---|---|---|---|
| 4,842,996 A | 6/1989 | Huynh-Dinh et al. |
| 5,328,470 A | 7/1994 | Nabel et al. |
| 5,814,014 A | 9/1998 | Elsberry et al. |
| 5,965,722 A | 10/1999 | Ecker et al. |
| 6,093,180 A | 7/2000 | Elsberry |
| 6,107,094 A | 8/2000 | Crooke |
| 6,245,427 B1 | 6/2001 | Duzgunes et al. |
| 6,358,932 B1 | 3/2002 | Monia |
| 6,361,940 B1 | 3/2002 | Van Ness et al. |
| 6,506,559 B1 | 1/2003 | Fire et al. |
| 7,241,618 B2 | 7/2007 | Agami et al. |
| 7,320,965 B2 | 1/2008 | Sah et al. |
| 7,459,547 B2 | 12/2008 | Zamore et al. |
| 2002/0012968 A1 | 1/2002 | Carroll et al. |
| 2002/0086356 A1 | 7/2002 | Tuschl et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0069195 A1 | 4/2003 | Farrar et al. |
| 2003/0108923 A1 | 6/2003 | Tuschl et al. |
| 2003/0144232 A1 | 7/2003 | Agami et al. |
| 2003/0144239 A1 | 7/2003 | Agami et al. |
| 2003/0162734 A1 | 8/2003 | Miller et al. |
| 2003/0180756 A1 | 9/2003 | Shi et al. |
| 2003/0190635 A1 | 10/2003 | McSwiggen |
| 2004/0023390 A1 | 2/2004 | Davidson et al. |
| 2004/0096843 A1 | 5/2004 | Rossi et al. |
| 2004/0162255 A1 | 8/2004 | Kaemmerer |
| 2004/0171030 A1 | 9/2004 | Baker et al. |
| 2004/0175703 A1 | 9/2004 | Kreutzer et al. |
| 2004/0180351 A1 | 9/2004 | Giese et al. |
| 2004/0192629 A1* | 9/2004 | Xu et al. .................. 514/44 |
| 2004/0203145 A1 | 10/2004 | Zamore et al. |
| 2004/0214198 A1 | 10/2004 | Rana |
| 2004/0219671 A1 | 11/2004 | McSwiggen et al. |
| 2004/0220132 A1 | 11/2004 | Kaemmerer |
| 2004/0229266 A1 | 11/2004 | Tuschl et al. |
| 2004/0241854 A1 | 12/2004 | Davidson et al. |
| 2004/0248299 A1 | 12/2004 | Jayasena et al. |
| 2004/0259247 A1 | 12/2004 | Tuschl et al. |
| 2004/0259248 A1 | 12/2004 | Tuschl et al. |
| 2005/0020521 A1 | 1/2005 | Rana |
| 2005/0026278 A1 | 2/2005 | Tuschl et al. |
| 2005/0037988 A1 | 2/2005 | Zamore et al. |
| 2005/0042646 A1 | 2/2005 | Davidson et al. |
| 2005/0059005 A1 | 3/2005 | Tuschl et al. |
| 2005/0074757 A1 | 4/2005 | Kreutzer et al. |
| 2005/0096284 A1 | 5/2005 | McSwiggen |
| 2005/0106731 A1 | 5/2005 | Davidson et al. |
| 2005/0130184 A1 | 6/2005 | Xu et al. |

(Continued)

FOREIGN PATENT DOCUMENTS

CA 2432341 A1 7/2002

(Continued)

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Aronin et al., CAG Expansion Affects the Expression of Mutant Huntingtin in the Huntington's Disease Brain, 1195, Neuron, vol. 15, pp. 1193-1201.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*

(Continued)

*Primary Examiner* — Amy Bowman
(74) *Attorney, Agent, or Firm* — Nelson Mullins Riley & Scarborough LLP; Debra J. Milasincic, Esq.; Briana M. Erickson

(57) ABSTRACT

The present invention relates to the discovery of an effective treatment for a variety of gain-of-function diseases, in particular, Huntington's disease (HD). The present invention utilizes RNA Interference technology (RNAi) against polymorphic regions in the genes encoding various gain-of-function mutant proteins resulting in an effective treatment for the gain-of-function disease.

9 Claims, 19 Drawing Sheets

U.S. PATENT DOCUMENTS

| | | | |
|---|---|---|---|
| 2005/0130919 A1 | 6/2005 | Xu et al. | |
| 2005/0137155 A1 | 6/2005 | McSwiggen et al. | |
| 2005/0176045 A1 | 8/2005 | Fedorov et al. | |
| 2005/0181382 A1 | 8/2005 | Zamore et al. | |
| 2005/0182005 A1 | 8/2005 | Tuschl et al. | |
| 2005/0186586 A1 | 8/2005 | Zamore et al. | |
| 2005/0186591 A1 | 8/2005 | Bumcrot et al. | |
| 2005/0191638 A1 | 9/2005 | McSwiggen | |
| 2005/0227256 A1 | 10/2005 | Hutvagner et al. | |
| 2005/0227940 A1 | 10/2005 | Rossi et al. | |
| 2005/0234006 A1 | 10/2005 | Tuschl et al. | |
| 2005/0234007 A1 | 10/2005 | Tuschl et al. | |
| 2005/0244858 A1 | 11/2005 | Rossi et al. | |
| 2005/0246794 A1 | 11/2005 | Khvorova et al. | |
| 2005/0255086 A1 | 11/2005 | Davidson et al. | |
| 2005/0256072 A1 | 11/2005 | Aronin et al. | |
| 2005/0273868 A1 | 12/2005 | Rana | |
| 2005/0277133 A1 | 12/2005 | McSwiggen | |
| 2005/0277610 A1 | 12/2005 | Rossi et al. | |
| 2006/0009402 A1 | 1/2006 | Zamore et al. | |
| 2006/0009408 A1 | 1/2006 | Davidson et al. | |
| 2006/0069050 A1 | 3/2006 | Rana | |
| 2006/0128650 A1* | 6/2006 | Xu | 514/44 |
| 2006/0134787 A1 | 6/2006 | Zamore et al. | |
| 2006/0166910 A1 | 7/2006 | Tuschl et al. | |
| 2006/0178328 A1 | 8/2006 | Kaemmerer | |
| 2006/0178334 A1 | 8/2006 | Rossi et al. | |
| 2006/0212950 A1 | 9/2006 | Tuschl et al. | |
| 2006/0257912 A1 | 11/2006 | Kaemmerer et al. | |
| 2006/0270623 A1 | 11/2006 | McSwiggen | |
| 2007/0003960 A1 | 1/2007 | Tuschl et al. | |
| 2007/0003961 A1 | 1/2007 | Tuschl et al. | |
| 2007/0003962 A1 | 1/2007 | Tuschl et al. | |
| 2007/0003963 A1 | 1/2007 | Tuschl et al. | |
| 2007/0031844 A1 | 2/2007 | Khvorova et al. | |
| 2007/0039072 A1 | 2/2007 | Khvorova et al. | |
| 2007/0093445 A1 | 4/2007 | Tuschl et al. | |
| 2007/0104688 A1 | 5/2007 | Rossi et al. | |
| 2007/0105803 A1 | 5/2007 | Manoharan et al. | |
| 2007/0111228 A1 | 5/2007 | Jayasena et al. | |
| 2007/0161590 A1 | 7/2007 | Van Bilsen et al. | |
| 2007/0161591 A1 | 7/2007 | Aronin et al. | |
| 2007/0161595 A1 | 7/2007 | Bumcrot et al. | |
| 2007/0207974 A1 | 9/2007 | Khvorova et al. | |
| 2007/0259827 A1 | 11/2007 | Aronin et al. | |
| 2007/0261126 A1 | 11/2007 | Kaemmerer et al. | |
| 2007/0265220 A1 | 11/2007 | Rossi et al. | |
| 2008/0039415 A1 | 2/2008 | Stewart et al. | |

FOREIGN PATENT DOCUMENTS

| | | |
|---|---|---|
| CA | 2432350 A1 | 7/2002 |
| DE | 10160151 A1 | 6/2003 |
| DE | 10302421 A1 | 7/2004 |
| EP | 1389637 A1 | 2/2004 |
| EP | 1527176 B1 | 5/2005 |
| EP | 1857547 A2 | 11/2007 |
| WO | WO-94/19493 A1 | 9/1994 |
| WO | WO-98/48009 A2 | 10/1998 |
| WO | WO-01/75164 A2 | 10/2001 |
| WO | WO-02/055692 A2 | 7/2002 |
| WO | WO-02/055693 A2 | 7/2002 |
| WO | WO-03/006477 A1 | 1/2003 |
| WO | WO-03/013437 A2 | 2/2003 |
| WO | WO-03/020931 A2 | 3/2003 |
| WO | WO-03/035869 A1 | 5/2003 |
| WO | WO-03/050306 A1 | 6/2003 |
| WO | WO-03/056012 A1 | 7/2003 |
| WO | WO-03/068797 A1 | 8/2003 |
| WO | WO-03/070895 A2 | 8/2003 |
| WO | WO-03/080807 A2 | 10/2003 |
| WO | WO-03/001335 A2 | 12/2003 |
| WO | WO-2004/013280 A2 | 2/2004 |
| WO | WO-2004/013310 A2 | 2/2004 |
| WO | WO-2004/013355 A1 | 2/2004 |
| WO | WO-2004/014933 A1 | 2/2004 |
| WO | WO-2004/015107 A2 | 2/2004 |
| WO | WO-2004/029212 A2 | 4/2004 |
| WO | WO-2004/042027 A2 | 5/2004 |
| WO | WO-2004/045543 A2 | 6/2004 |
| WO | WO-2004/046324 A2 | 6/2004 |
| WO | WO-2004/047872 A2 | 6/2004 |
| WO | WO-2004/058940 A2 | 7/2004 |
| WO | WO-2004/065601 A2 | 8/2004 |
| WO | WO-2004/080406 A2 | 9/2004 |
| WO | WO-2004/111072 A2 | 12/2004 |
| WO | WO-2004/111191 A2 | 12/2004 |
| WO | WO-2005/001043 A2 | 1/2005 |
| WO | WO-2005/003350 A2 | 1/2005 |
| WO | WO-2005/007875 A2 | 1/2005 |
| WO | WO-2005/007877 A2 | 1/2005 |
| WO | WO-2005/019453 A2 | 3/2005 |
| WO | WO-2005/023991 A2 | 3/2005 |
| WO | WO-2005/027980 A1 | 3/2005 |
| WO | WO-2005/045034 A2 | 5/2005 |
| WO | WO-2005/062937 A2 | 7/2005 |
| WO | WO-2005/069987 A2 | 8/2005 |
| WO | WO-2005/078096 A2 | 8/2005 |
| WO | WO-2005/079532 A2 | 9/2005 |
| WO | WO-2005/079533 A2 | 9/2005 |
| WO | WO-2005/089287 A2 | 9/2005 |
| WO | WO-2005/116212 A2 | 12/2005 |
| WO | WO-2006/015389 A2 | 2/2006 |
| WO | WO-2006/121960 A2 | 11/2006 |
| WO | WO-2007/002904 A2 | 1/2007 |
| WO | WO-2007/022470 A2 | 2/2007 |
| WO | WO-2007/047692 A2 | 4/2007 |
| WO | WO-2007/087451 A2 | 8/2007 |
| WO | WO-2008/005562 A2 | 1/2008 |
| WO | WO-2008/021136 A2 | 2/2008 |
| WO | WO-2008/021157 A1 | 2/2008 |
| WO | WO-2008/143774 A2 | 11/2008 |

OTHER PUBLICATIONS

Aronin et al., CAG Expansion Affects the Expression of Mutant Huntingtin in the Huntington's Disease Brain, 1195, Neuron, vol. 15, pp. 1193-1201.*

Aronin, Neil et al., "Are there multiple pathways in the pathogenesis of Huntington's disease?" *Phil. Trans. R. Soc. Lond. B*, vol. 354:995-1003 (1999).

Aronin, Neil et al., "CAG Expansion Affects the Expression of Mutant Huntingtin in the Huntington's Disease Brain," *Neuron*, vol. 15:1193-1201 (1995).

Bagella, Luigi et al., "Cloning of Murine CDK9/PITALRE and Its Tissue-Specific Expression in Development," *Journal of Cellular Physiology*, vol. 177:206-213 (1998).

Boudreau, Ryan L. et al., "Nonallele-specific Silencing of Mutant and Wild-type Huntingtin Demonstrates Therapeutic Efficacy in Huntington's Disease Mice," *Molecular Therapy*, doi:10.1038/mt.2009.17 (2009).

Brummelkamp, Thijn R. et al., "A System for Stable Expression of Short Interfering RNAs in Mammalian Cells," *Science*, vol. 296:550-553 (2002).

Calegari, Federico et al., "Tissue-specific RNA interference in postimplantation mouse embryos with endoribonuclease-prepared short interfering RNA," *PNAS*, vol. 99(22):14236-14240 (2002).

Caplen, Natasha J. et al., "Rescue of polyglutamine-mediated cytotoxicity by double-stranded RNA-mediated RNA interference," *Human Molecular Genetics*, vol. 11(2):175-184 (2002).

DiFiglia, Marian et al., "Aggregation of Huntingtin Neuronal Intranuclear Inclusions and Dystrophic Neurites in Brain," *Science*, vol. 277:1990-1993 (1997).

Ding, Hongliu et al., "Selective silencing by RNAi of a dominant allele that causes amyotrophic lateral sclerosis," *Aging Cell*, vol. 2:209-217 (2003).

Elbashir, Sayda M. et al., "RNA interference is mediated by 21- and 22-nucleotide RNAs," *Genes & Development*, vol. 15:188-200 (2001).

Fluiter, K. et al., "Killing cancer by targeting genes that cancer cells have lost: Allele-specific inhibition, a novel approach to the treatment of genetic disorders," *CMLS, Cell. Mol. Life Sci.*, vol. 60:834-843 (2003).

Goto, J. et al., "Suppression of Huntingtin Gene Expression by siRNA: A Possible Therapeutic Tool for Huntington's Disease," *Neurology*, vol. 60(5 Suppl. 1):A286 (2003).

Haley, Benjamin et al., "In vitro analysis of RNA interference in *Drosophila melanogaster*," *Methods*, vol. 30:330-336 (2003).

Hutvágner, György et al., "A microRNA in a Multiple-Turnover RNAi Enzyme Complex," *Science*, vol. 297:2056-2060 (2002).

Jacque, Jean-Marc et al., "Modulation of HIV-1 replication by RNA interference," *Nature*, vol. 418:435-438 (2002).

Kremer, Berry et al., "A Worldwide Study of the Huntington's Disease Mutation: The Sensitivity and Specificity of Measuring CAG Repeats," *The New England Journal of Medicine*, vol. 330(20):1401-1406 (1994).

Laforet, Genevieve A. et al., "Changes in Cortical and Striatal Neurons Predict Behavioral and Electrophysiological Abnormalities in a Transgenic Murine Model of Huntington's Disease," *The Journal of Neuroscience*, vol. 21(23):9112-9123 (2001).

Lee, Yoontae et al., "MicroRNA maturation: stepwise processing and subcellular localization," *The EMBO Journal*, vol. 21(17):4663-4670 (2002).

Lewis, David L. et al., "Efficient delivery of siRNA for inhibition of gene expression in postnatal mice," *Nature Genetics*, vol. 32:107-108 (2002).

Liu, Wanzhao et al., "Linking SNPs to CAG repeat length in Huntington's disease patients," *Nature Methods*, vol. 5(11):951-953 (2008).

MacDonald, Marcy E. et al., "A Novel Gene Containing a Trinucleotide Repeat That Is Expanded and Unstable on Huntington's Disease Chromosomes," *Cell*, vol. 72:971-983 (1993).

McCaffrey, Anton P. et al., "A story of mice and men," *Gene Therapy*, vol. 9:1563 (2002).

McManus, Michael T. et al., "Gene silencing using micro-RNA designed hairpins," *RNA*, vol. 8:842-850 (2002).

Miller, Victor M. et al., "Allele-specific silencing of dominant disease genes," *PNAS*, vol. 100(12):7195-7200 (2003).

Miyagishi, Makoto et al., "U6 promoter-driven siRNAs with four uridine 3' overhangs efficiently suppress targeted gene expression in mammalian cells," *Nature Biotechnology*, vol. 19:497-500 (2002).

Nellemann, Christine et al., "Inhibition of Huntingtin Synthesis by Antisense Oligodeoxynucleotides," *Molecular and Cellular Neuroscience*, vol. 16:313-323 (2000).

Nykanen, Antti et al., "ATP Requirements and Small Interfering RNA Structure in the RNA Interference Pathway," *Cell*, vol. 107:309-321 (2001).

Paddison, Patrick J. et al., "Short hairpin RNAs (shRNAs) induce sequence-specific silencing in mammalian cells," *Genes & Development*, vol. 16:948-958 (2002).

Paul, Cynthia P. et al., "Effective expression of small interfering RNA in human cells," *Nature Biotechnology*, vol. 29:505-508 (2002).

Schwarz, Dianne S. et al., "Designing siRNA That Distinguish between Genes That Differ by a Single Nucleotide," *PLoS Genetics*, vol. 2(9):1307-1318 (2006).

Sui, Guangchao et al., "A DNA vector-based RNAi technology to suppress gene expression in mammalian cells," *PNAS*, vol. 99(8):5515-5520 (2002).

Tuschl, Thomas, "Expanding small RNA interference," *Nature Biotechnology*, vol. 20:446-448 (2002).

Tuschl, Thomas et al., "Targeted mRNA degradation by double-stranded RNA in vitro," *Genes & Development*, vol. 13:3191-3197 (1999).

van Bilsen, P.H.J. et al., "Identification and Allele-Specific Silencing of the Mutant Huntingtin Allele in Huntington's Disease Patient-Derived Fibroblasts," *Human Gene Therapy*, vol. 19:710-718 (2008).

Xia, Haibin et al., "siRNA-mediated gene silencing in vitro and in vivo," *Nature Biotechnology*, vol. 20:1006-1010 (2002).

Yohrling, George J. et al., "Mutant huntingtin increases nuclear corepressor function and enhances ligand-dependent nuclear hormone receptor activation," *Molecular and Cellular Neuroscience*, vol. 23:28-38 (2003).

Yu, Jenn-Yah et al., "RNA interference by expression of short-interfering RNAs and hairpin RNAs in mammalian cells," *PNAS*, vol. 99(9):6047-6052 (2002).

Zamore, Phillip D. et al., "RNAi: Double-Stranded RNA Directs the ATP-Dependent Cleavage of mRNA at 21 to 23 Nucleotide Intervals," *Cell*, 101:25-33 (2000).

Zamore, Phillip D. et al., "siRNAs knock down hepatitis," *Nature Medicine*, vol. 9(3):266-267 (2003).

Zeng, Yan et al., "Both Natural and Designed Micro RNAs Can Inhibit the Expression in Cognate mRNAs When Expressed in Human Cells," *Molecular Cell*, vol. 9:1327-1333 (2002).

Akhtar, Saghir et al., "Nonviral delivery okf synthetic siRNAs in vivo," The Journal of Clinical Investigation, vol. 117(12):3623-3632 (2007).

Bumcrot, David et al., "RNAi therapeutics: a potential new class of pharmaceutical drugs," Nature Chemical Biology, vol. 2(12):711-719 (2006).

Corey, David R., "Chemical modification: the key to clinical application of RNA interference?" The Journal of Clinical Investigation, vol. 117(12):3615-3622 (2007).

Gewirtz, Alan M., "On future's doorstep: RNA interference and the pharmacopeia of tomorrow," The Journal of Clinical Investigation, vol. 117(12):3612-3614 (2007).

Grimm, Dirk et al., "Therapeutic application of RNAi: is mRNA targeting finally ready for prime time?" The Journal of Clinical Investigation, vol. 117(12):3633-3641 (2007).

Hu-Lieskovan, Siwen et al., "Sequence-Specific Knockdown of EWS-FLI1 by Targeted, Nonviral Delivery of Small Interfering RNA Inhibits Tumor Growth in a Murine Model of Metastatic Ewing's Sarcoma," Cancer Res., vol. 65 (19):8984-8992 (2005).

Kim, David H. et al., "Strategies for silencing human disease using RNA interference," Nature Reviews Genetics, vol. 8:173-184 (2007).

Li, Bao-jian et al., "Using siRNA in prophylactic and therapeutic regimens against SARS coronavirus in *Rhesus macaque*," Nature Medicine, vol. 11(9):944-951 (2005).

Reich, Samuel J. et al., "Small interfering RNA (siRNA) targeting VEGF effectively inhibits ocular neovascularization in a mouse model," Molecular Vision, vol. 9:910-916 (2003).

Soutschek, Juergen et al., "Therapeutic silencing of an endogenous gene by systemic administration of modified siRNAs," Nature, vol. 432:173-178 (2004).

Tan, P-H et al., "Gene knockdown with intrathecal siRNA of NMDA receptor NR2B subunit reduces formalin-induced nociception in the rat," Gene Therapy, vol. 12:59-66 (2005).

Thakker, Deepak R. et al., "Neurochemical and behavioral consequences of widespread gene knockdown in the adult mouse brain by using nonviral RNA interference," PNAS, vol. 101(49):17270-17275 (2004).

US 5,782,242, 02/1999, Monia, (withdrawn).

Abdelgany, Amr et al., "Allele-specific silencing of a pathogenic mutant acetylcholine receptor subunit by RNA interference," *Human Molecular Genetics*, vol. 12(20):2637-2644 (2003).

Arriarguioui, Mohammed et al., "Rational design and in vitro and in vivo delivery of Dicer substrate si RNA," *Nature Protocols*, vol. 1(2):508-517 (2006).

Amarzguioui, Mohammed et al., "Tolerance for mutations and chemical modifications in a siRNA," *Nucleic Acids Research*, vol. 31(2):589-595 (2003).

Ambros, Victor et al., "MicroRNAs and Other Tiny Endogenous RNAs in *C. elegans*," *Current Biology*, vol. 13:807-818 (2003).

Aoki, Yuji et al., "Potential tumor-targeting peptide vector of histidylated oligolysine conjugated to a tumor-homing RGD motif," *Cancer Gene Therapy*, vol. 8:783-787 (2001).

Aravin, Alexei A. et al., "The Small RNA Profile during *Drosophila melanogaster* Development," *Developmental Cell*, vol. 5:337-350 (2003).

Bailly, Christian et al., "The use of diaminopurine to investigate structural properties of nucleic acids and molecular recognition between ligands and DNA," *Nucleic Acids Research*, vol. 26(19):4309-4314 (1998).

Bartel DP. MicroRNAs: genomics, biogenesis, mechanism, and function. Cell. Jan. 23, 2004;116(2):281-97.

Bass, Brenda L., "The short answer," *Nature*, vol. 411:428-429 (2001).

Behding, Anders et al., "In vitro photochemical cataract in mice lacking copper-zinc superoxide dismutase," *Free Radical Biology & Medicine*, vol. 31(6):738-744 (2001).
Bernstein, Emily et al., "Role for a bidentate ribonuclease in the initiation step of RNA interference," *Nature*, vol. 409:363-366 (2001).
Bijsterbosch, Martin K. et al., "Modulation of plasma protein binding and in vivo liver cell uptake of phosphorothioate oligodeoxynucleotides by cholesterol conjugation," *Nucleic Acids Research*, vol. 28(14):2717-2725 (2000).
Boden, Daniel et al., "Efficient Gene Transfer of HIV-1-Specific Short Hairpin RNA into Human Lymphocytic Cells Using Recombinant Adeno-associated Virus Vectos," *Molecular Therapy*, vol. 9(3):396-402 (2004).
Boden, Daniel et al., "Enhanced gene silencing of HIV-1 specific siRNA using microRNA designed hairpins," *Nucleic Acids Research*, vol. 32(3):1154-1158 (2004).
Bohnsack, Markus T. et al., "Exportin 5 is a RanGTP-dependent dsRNA-binding protein that mediates nuclear export of pre-miRNAs," *RNA*, vol. 10:185-191 (2004).
Bonnet, Eric et al., "Evidence that microRNA precursors, unlike other non-coding RNAs, have lower folding free energies than random sequences," *Bioinformatics*, vol. 20(17):2911-2917 (2004).
Boutla, Alexandra et al, "Developmental defects by antisense-mediated inactivation of micro-RNAs 2 and 13 in *Drosophila* and the identification of putative target genes," *Nucleic Acids Research*, vol. 31(17):4973-4980 (2003).
Boutla, Alexandra et al, "Short 5'-phosphorylated double-stranded RNAs induce RNA interference in *Drosophila*," *Current Biology*, vol. 11:1776-1780 (2001).
Bracht, John et al., "*Trans*-splicing and polyadenylation of *let-7* microRNA primary transcripts," *RNA*, vol. 10:1586-1594 (2004).
Brennecke, Julius et al., "*bantam* Encodes a Developmentally Regulated microRNA that Controls Cell Proliferation and Regulates the Proapoptotic Gene *hid* in *Drosophila*," *Cell*, vol. 113:25-36 (2003).
Brennecke, Julius et al., "Principles of MicroRNA—Target Recognition," *PLoS Biology*, vol. 3(3):0404-0418 (2005).
Brennecke, Julius et al., "Towards a complete description of the microRNA complement of animal genomes," *Genome Biology*, vol. 4:228.1-228.3 (2003).
Brown, Kirk M. et al., "Target accessibility dictates the potency of human RISC," *Nature Structural & Molecular Biology*, vol. 12(5):469-470 (2005).
Brummelkamp, Thijn R. et al., "Stable suppression of tumorigenicity by virus-mediated RNA interference," *Cancer Cell*, vol. 2:243-247 (2002).
Burgess, Kevin et al., "Photolytic Mass Laddering for Fast Characterization of Oligomers on Single Resin Beads," *J. Org. Chem.*, vol. 62:5662-5663 (1997).
Caccone, Adalgisa et al., "Calibration of the Change in Thermal Stability of DNA Duplexes and Degree of Base Pair Mismatch," *J. Mol. Evol.*, vol. 27:212-216 (1988).
Cai, Xuezhong et al., "Human microRNA are processed from capped, polyadenylated transcripts that can also function as mRNAs," *RNA*, vol. 10:1957-1966 (2004).
Caplen, Natasha J. et al., "dsRNA-mediated gene silencing in cultured *Drosophila* cells: a tissue culture model for the analysis of RNA interference," *Gene*, vol. 252:95-105 (2000).
Caplen, Natasha J., "RNAi as a gene therapy approach," *Expert Opin. Biol. Ther.*, vol. 3(4):575-586 (2003).
Caplen, Natasha J. et al., "Specific inhibition of gene expression by small double-stranded RNAs in invertebrate and vertebrate systems," *PNAS*, vol. 98(17):9742-9747 (2001).
Carthew, Richard W., "Gene silencing by double-stranded RNA," *Current Opinion in Cell Biology*, vol. 13:244-248 (2001).
Catalanotto, Caterina et al., "Gene silencing in worms and fungi," *Nature*, vol. 404:245 (2000).
Catalanotto, Caterina et al., "Involvement of small RNAs and role of the *qde* genes in the gene silencing pathway in Neurospora," *Genes & Development*, vol. 16:790-795 (2002).
Caudy, Amy A. et al., "Fragile X-related protein and VIG associate with the RNA interference machinery," *Genes & Development*, vol. 16:2491-2496 (2002).

Chalk, A.M. et al., "siRNAdb: a database of siRNA sequences," *Nucleic Acids Research*, vol. 33:D131-D134 (2005).
Chaloin, L. et al., "Design of Carrier Peptide-Oligonucleotide Conjugates with Rapid Membrane Translocation and Nuclear Localization Properties," *Biochemical and Biophysical Research Communications*, vol. 243:601-608 (1998).
Check, Erika, "RNA to the rescue?" *Nature*, vol. 425:10-12 (2003).
Chen, Shu-Hsia et al., "Gene therapy for brain tumors: Regression of experimental gliomas by adenovirus-mediated gene transfer in vivo," *Proc. Natl. Acad. Sci. USA*, vol. 91:3054-3057 (1994).
Chen, Zongyu J. et al., "Sleeping Beauty-mediated down-regulation of huntingtin expression by RNA interference," *Biochemical and Biophysical Research Communication*, vol. 329:646-652 (2005).
Chi, Jen-Tsan et al., "Genomewide view of gene silencing by small interfering RNAs," *PNAS*, vol. 100(11):6343-6346 (2003).
Chiu, Ya-Lin et al, "RNAi in Human Cells: Basic Structural and Functional Features of Small Interfering RNA," *Molecular Cell*, vol. 10:549-561 (2002).
Chiu, Ya-lin et al, "siRNA function in RNAi: A chemical modification analysis," RNA, vol. 9:1034-1048 (2003).
Cleveland, Don W. et al., "From Charcot to Lou Gehrig: Deciphering Selective Motor Neuron Death in ALS," *Nature*, vol. 2:806-819 (2001).
Cogoni, Carlo et al., "Gene silencing in *Neurospora crassa* requires a protein homologous to RNA-dependent RNA polymerase," *Nature*, vol. 399:166-168 (1999).
Cogoni, Carlo et al., "Isolation of quelling-defective (*qde*) mutants impaired in posttranscriptional transgene-induced gene silencing in *Neurospora crassa*," *Proc. Natl. Acad. Sci. USA*, vol. 94:10233-10238 (1997).
Cogoni, Carlo et al., "Posttranscriptional Gene Silencing in *Neurospora* by a RecQ DNA Helicase," *Science*, vol. 286:2342-2344 (1999).
Conte, Darryl Jr. et al., "RNA Interference in *Caenorhabditis elegans*," *Current Protocols in Molecular Biology*, F.M. Asubel et al., eds., John Wiley & Sons, pp. 26.3.1-26.3.20 (2003).
Cullen, Bryan R., "Enhancing and confirming the specificity of RNAi experiments," *Nature Methods*, vol. 3(9):677-681 (2006).
Czauderna, Frank et al., "Structural variations and stabilising modifications of synthetic siRNAs in mammalian cells," *Nucleic Acids Research*, vol. 31(11):2705-2716 (2003).
Dalmay, Tamas et al., "*SDE3* encodes an RNA helicase required for posttranscriptional gene silencing in *Arabidopsis*," *The EMBO Journal*, vol. 20(8):2069-2077 (2001).
Dalmay, Tamas et al., "An RNA-Dependent RNA Polymerase Gene in *Arabidopsis* Is Required for Posttranscriptional Gene Silencing Mediated by a Transgene but Not by a Virus," *Cell*, vol. 101:543-553 (2000).
Denli, Ahmet M. et al., "Processing of primary microRNAs by the Microprocessor complex," *Nature*, vol. 432:231-235 (2004).
Davidson, Beverly L. et al., "Molecular medicine for the brain: silencing of disease genes with RNA interference," *The Lancet*, vol. 3:145-149 (2004).
Derossi, Daniele et al., "The Third Helix of the Antennapedia Homeodomain Translocates through Biological Membranes," *The Journal of Biological Chemistry*, vol. 269(14):10444-10450 (1994).
Devroe, Eric et al., "Retrovirus-delivered siRNA," *BMC Biotechnology*, vol. 2:15-19 (2002).
DiFiglia, Marian et al., "Huntingtin Is a Cytoplasmic Protein Associated with Vesicles in Human and Rat Brain Neurons," *Neuron*, vol. 14:1075-1081 (1995).
DiFiglia, M. et al., "Therapeutic silencing of mutant huntingtin with siRNA attenuates striatal and cortical neuropathology and behavioral deficits," *PNAS*, vol. 104(43):17204-17209 (2007).
Doench, John G. et al., "siRNAs can function as miRNAs," *Genes & Development*, vol. 17:438-442 (2003).
Doench, John G. et al., "Specificity of microRNA target selection in translational repression," *Genes & Development*, 2004:504-511 (2004).
Dostie, Josee et al, "Numerous microRNPs in neuronal cells containing novel microRNAs," *RNA*, vol. 9:180-186 (2003).

Du, Quan et al., "A systematic analysis of the silencing effects of an active siRNA at all single-nucleotide nucleotide mismatched target sites," *Nucleic Acids Research*, vol. 33(5):1671-1677 (2005).
Duprez, Laurence, et al., "Pathology of the TSH Receptor," *Journal of Pediatric Endocrinology & Metabolism*, vol. 12:295-302 (1999).
Dykxhoorn, Derek M. et al., "Determinants of specific RNA interference-mediated silencing of human β-globin alleles differing by a single nucleotide polymorphism," *PNAS*, vol. 103(15):5953-5958 (2006).
Elbashir, S.M., et al., "Duplexes of 21-nucleotide RNAs mediate RNA interferences in cultured mammalian cells," *Nature*, vol. 411:494-498 (2001).
Elbashir, S.M., et al., "Functional anatomy of siRNAs for mediateing efficient RNAi in *Drosophila melanogaster* embryo lysate,"*Embo. J.*, vol. 20:6877-6888 (2001).
Elmquist, Anna et al., "VE-Cadherin-Derived Cell-Penetrating Peptide, *p*VEC, with Carrier Functions," *Experimental Cell Research*, vol. 269:237-244 (2001).
Enright, Anton J. et al., "MicroRNA targets in *Drosophila,*" *Genome Biology*, vol. 5:R1.1-R1.14 (2003).
Epa, W. Ruwan et al., "Enhanced Downregulation of the p75 Nerve Growth Factor Receptor by Cholesteryl and Bis-Cholesteryl Antisense Oligonucleotides," *Antisenxe & Nucleic Acid Drug Development*, vol. 8:489-498 (1998).
Fagard, Mathilde et al., "AGO1, QDE-2, and RDE-1 are related proteins required for post-transcriptional gene silencing in plants, quelling in fungi, and RNA interference in animals," *PNAS*, vol. 97(21):11650-11654 (2000).
Fire, Andrew et al., "Potent and specific genetic interference by double-stranded RNA in *Caenorhabditis elegans,*" *Nature*, vol. 391:806-811 (1998).
Flood, Dorothy G. et al., "Hindlimb Motor Neurons Require Cu/Zn Superoxide Dismutase for Maintenance of Neuromuscular Junctions," *American Journal of Pathology*, vol. 155(2):663-672 (1999).
Fluiter, Kees et al., "Tumor Genotype-specific Growth Inhibition in Vivo by Antisense Oligonucleotides against a Polymorphic Site of the Large Subunit of Human RNA Polymerase II," *Cancer Research*, vol. 62:2024-2028 (2002).
Forstemann, K. et al., "Normal microRNA maturation and germ-line stem cell maintenance requires loquacious, a double-stranded RNA-binding domain protein," PLOS Biology, vol. 3(7):1-15 (2005).
Francis, Ross et al., "*aph-1* and *pen-2* Are Required for Notch Pathway Signaling, γ-Secretase Cleavage of βAPP, and Presenilin Protein Accumulation," *Development Cell*, vol. 3:85-97 (2002).
Fressinaud, Edith et al., "Molecular Genetics of Type 2 von Willebrand Disease," *International Journal of Hematology*, vol. 75:9-18 (2002).
Gante, Joachim, "Azapeptides," *Synthesis*, vol. 6:405-406 (1989).
Gaudette, Mara et al., "Current status of SOD1 mutations in familial amyotrophic lateral sclerosis," *Amyotrophic Lateral Sclerosis*, vol. 1(2):83-89 (2000).
GenBank Accession No. NM_002111, Rangone, H. et al., "PHosphorylation of arfaptin 2 at Ser260 by Akt Inhibits PolyQ-huntingtin-induced toxicity by rescuing proteasome impairment," *J. Biol. Chem.*, vol. 280(23):22021-22028 (2005) Aug. 8, 2005.
German Application, File No. 101 55 280.7, dated Oct. 26, 2001.
German Application, File No. 101 58 411.3, dated Nov. 29, 2001.
German Application, File No. 101 60 151.4, dated Dec. 7, 2001.
German Application, File No. 102 35 620.3, dated Aug. 2, 2002.
Ghildiyal, Megha et al., "Small silencing RNAs: an expanding universe," *Nature Review Genetics*, vol. 10:94-108 (2009).
Griffiths-Jones, Sam, "The microRNA Registry," *Nucleic Acids Research*, vol. 32:D109-D111 (2004).
Gewirtz, Alan M. et al., "On future's doorstep: RNA interference and the pharmacopeia of tomorrow," *The Journal of Clinical Investigation*, vol. 117(12):3612-3614 (2007).
Grishok, A. et al.,"Genes and Mechanisms related to RNA interference regulate expression of the small temporal RNAs that control *C. elegans* development timing," *Cell*, vol. 106:23-34 (2001).
Grishok, Alla et al., "Genetic Requirements for Inheritance of RNAi in *C. elegans,*" *Science*, vol. 287:2494-2497 (2000).
Grishok, Alla et al., "RNAi (Nematodes *Caenorhabditis elegans*)," *Advances in Genetics*, vol. 46:339-360 (2002).

Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," *Human Gene Therapy*, 17:751-766 (2006).
Gualberto, Antonio, et al., "An oncogenic form of p53 confers a dominant, gain-of-function phenotype that disrupts spindle checkpoint control," *Proc. Natl. Acad. Sci. USA*, vol. 95:5166-5171 (1998).
Ha, Ilho et al., "A bulged *lin-4/lin-14* RNA duplex is sufficient for *Caenorhabditis elegans lin-14* temporal gradient formation," *Genes & Development*, vol. 10:3041-3050 (1996).
Haley, B. et al.,"Kinetic analysis of the RNAi enzyme complex," Nature Structural & Molecular Biology, vol. 11(7):599-606 (2004).
Halldórsson, Bjarni V. et al., "Optimal Selection of SNP Markers for Disease Association Studies," *Hum. Hered.*, vol. 58:190-202 (2004).
Hamilton, Andrew J. et al., "A Species of Small Antisense RNA in Posttranscriptional Gene Silencing in Plants," *Science*, vol. 286:950-952 (1999).
Hammond, Scott M. et al., "An RNA-directed nuclease mediates post-transcriptional gene silencing in *Drosophila* cells," *Nature*, vol. 404:293-296 (2000).
Hammond, Scott M. et al., "Argonaute2, a Link Between Genetic and Biochemical Analyses of RNAi," *Science*, vol. 293:1146-1150 (2001).
Hammond, Scott M. et al., "Post-Transcriptional Gene Silencing by Double-Stranded RNA," *Nature*, vol. 2:110-119 (2001).
Hannon, Gregory J., "RNA interference," *Nature*, vol. 418:244-251 (2002).
Hannon, Gregory J. et al., "Unlocking the potential of the human genome with RNA interference," *Nature*, vol. 431:371-378 (2004).
Harborth, Jens et al., "Identification of essential genes in cultured mammlian cells using small interfering RNAs," *Journal of Cell Science*, vol. 114:4557-4565 (2001).
Harper, Scott Q. et al., "RNA interference improves motor and neuropathological abnormalities in a Huntington's disease mouse model," *PNAS*, vol. 102(16):5820-5825 (2005).
Haubner, Roland et al., "Glycosylated RGD-Containing Peptides: Tracer for Tumor Targeting and Angiogenesis Imaging with Improved Biokinetics," *The Journal of Nuclear Medicine*, vol. 42(2):326-336 (2001).
Heale, Bret S.E. et al., "siRNA target site secondary structure predictions using local stable substructures," *Nucleic Acids Research*, vol. 33(3):1-10 (2005).
Hirota, Seiichi et al., "Gain-of-function mutation at the extracellular domain of KIT in gastrointestinal stromal tumours," *Journal of Pathology*, vol. 193:505-510 (2001).
Hirota, Seiichi, et al., "Gain-of-Function Mutations of *c-kit* in Human Gastrointestinal Stromal Tumors," *Science*, vol. 279:577-580 (1998).
Hixon, M.L., et al., "Gain of function properties of mutant p53 proteins at the mitotic spindle cell cycle checkpoint," *Histology and Histopathology*, vol. 15:551-556 (2000).
Ho, L.W., et al., "The molecular biology of Huntington's disease," *Psychological Medicine*, vol. 31:3-14 (2001).
Hoehn, Margaret M. et al., "Parkinsonism: onset, progression, and mortality," *Neurology*, vol. 17(5):427-442 (1967).
Hohjoh, Hirohiko, "Enhancement of RNAi activity by improved siRNA duplexes," *FEBS Letters*, vol. 557:193-198 (2004).
Hojo, S. et al., "Heterogeneous point mutations of the p53 gene in pulmonary fibrosis," *Eur. Respir. J.*, vol. 12:1404-1408 (1998).
Holen, Torgeir et al., "Positional effects of short interfering RNAs targeting the human coagulation trigger Tissue Factor," *Nucleic Acids Research*, vol. 30(8):1757-1766 (2002).
Holen, Torgeir et al., "Similar behaviour of single-strand and double-strand siRNAs suggests they act through a common RNAi pathway," *Nucleic Acids Research*, vol. 31(9):2401-2407 (2003).
Holmes, Christopher P., et al., "Strategies for Combinatorial Organic Synthesis: Solution and Polymer-Supported Synthesis of 4-Thiazolidinones and 4-Metathiazanones Derived from Amino Acids," *J. Org. Chem.*, vol. 60:7328-7333 (1995).
Hsieh, Andrew C. et al., "A library of siRNA duplexes targeting the phosphoinositide 3-kinase pathway: determinants of gene silencing for use in cell-based screens," *Nucleic Acids Research*, vol. 32(3):893-901 (2004).

Hutvagner. G. et al.,"A cellular function for the RNA-interference enzyme dicer in the maturation of the let-7 small temporal RNA," Science, vol. 293:834-838 (2001).

Hutvágner, György, et al., "RNAi: nature abhors a double-strand," Curr. Opin. Genet. Dev., vol. 12:225-232 (2002).

Jackson, Aimee L. et al., "Expression profiling reveals off-target gene regulation by RNAi," Nature Biotechnology, vol. 21(6):635-637 (2003).

Jackson, Aimee L. et al., "Position-specific chemical modification of siRNAs reduces 'off-target' transcript silencing," RNA, vol. 12:1197-1205 (2006).

Jackson, Aimee L. et al., "Widespread siRNA 'off-target' transcript silencing mediated by seed region sequence complementarity," RNA, vol. 12:1179-1187 (2006).

Kato, Shinsuke et al., "New consensus research on neuropathological aspects of familial amyotrophic lateral sclerosis with superoxide dismutase 1 (SOD1) gene mutations: Inclusions containing SOD1 in neurons and astrocytes," ALS, vol. 1:163-184 (2000).

Kawase, Makoto et al., "Exacerbation of Delayed Cell Injury After Transient Global Ischemia in Mutant Mice With CuZn Superoxide Dismutase Deficiency," Stroke, vol. 30:1962-1968 (1999).

Ketting, René F. et al., "Dicer functions in RNA interference and in synthesis of small RNA involved in developmental timing in C. elegans," Genes & Development, vol. 15:2654-2659 (2001).

Ketting, René F. et al., "A genetic link between co-suppression and RNA interference in C. elegans," Nature, vol. 404:296-298 (2000).

Ketting, René F. et a., "mut-7 of C. elegans, Required for Transposon Silencing and RNA Interference, Is a Homolog of Werner Syndrome Helicase and RNaseD," Cell, vol. 99:133-141 (1999).

Khan, Alim et al., "Sustained Polymeric Delivery of Gene Silencing Antisense ODNs, siRNA, DNAzymes and Ribozymes: In Vitro and In Vivo Studies," Journal of Drug Targeting, vol. 12(6):393-404 (2004).

Khvorova, A. et al.,"Functional siRNAs and miRNAs exhibit strand bias," Cell, vol. 115:209-216 (2003).

Kierzek, Ryszard et al., "Thermodynamics of Single Mismatches in RNA Duplexes," Biochemistry, vol. 38:14214-14223 (1999).

Kim, V.N. et al.,"MicroRNA Biogenesis: Coordinated cropping and dicing," Nature Reviews, vol. 6:376-385 (2005).

Kim, Dong-Ho et al., "Synthetic dsRNA Dicer substrates enhances RNAi potency and efficacy," Nature Biotechnology, vol. 23(2):222-226 (2005).

Kiriakidou, Marianthi et al., "A combined computational-experimental approach predicts human microRNA targets," Genes & Development, vol. 18:1165-1178 (2004).

Klug, N. et al., "A selective antisense oligonucleotide against the G93A mutant of the Cu/Zn-SOD1 mRNA, applied to the mouse brain," European Journal of Physiology, vol. 441(Suppl. 6):R205, No. P20-7 (2001).

Knight, Scott W. et al., "A Role for the RNase III Enzyme DCR-1 in RNA Interference and Germ Line Development in Caenorhabditis elegans," Science, vol. 293:2269-2271 (2001).

Kondo, Takeo et al., "Reduction of CuZn-Superoxide Dismutase Activity Exacerbates Neuronal Cell Injury and Edema Formation after Transient focal Cerebral Ischemia," The Journal of Neuroscience, vol. 17(11):4180-4189 (1997).

Kopp, P., "Human Genome and Diseases: Review, The TSH receptor and its role in thyroid disease," CMLS, Cell. Mol. Life Sci., vol. 58:1301-1322 (2001).

Kosaki, Kenjiro et al., "PTPN11 (Protein-Tyrosine Phosphatase, Nonreceptor-Type II) Mutations in Seven Japanese Patients with Noonan Syndrome," The Journal of Clinical Endocrinology & Metabolism, vol. 87(8):3529-3533 (2002).

Krol, Jacek et al., "Structural Features of MicroRNA (miRNA) Precursors and Their Relevance to miRNA Biogenesis and Small Interfering RNA/Short Hairpin RNA Design," The Journal of Biological Chemistry, vol. 279(40):42230-42239 (2004).

Kunst, Catherine B. et al., "Mutations in SOD1 associated with amyotrophic lateral sclerosis cause novel protein interactions," Nature Genetics, vol. 15:91-94 (1997).

Kwong, J.Q. et al., "RNAi-mediated inhibition of mutated htt in Huntington's disease models," Society for Neuroscience, Abstract, Presentation No. 208.18 (2003).

Lagos-Quintana, Mariana et al., "Identification of Novel Genes Coding for Small Expressed RNAs," Science, vol. 294:853-858 (2001).

Lagos-Quintana, Mariana et al., "Identification of Tissue-Specific MicroRNAs from Mouse," Current Biology, vol. 12:735-739 (2002).

Lagos-Quintana, Mariana et al., "New MicroRNAs from mouse and human," RNA, vol. 9:175-179 (2003).

Lai, Eric C., "Micro RNAs are complementary to 3' UTR sequence motifs that mediate negative post-transcriptional regulation," Nature Genetics, vol. 30:363-364 (2002).

Lam, Kit S. et al., "A new type of synthetic peptide library for identifying ligand-binding activity," Nature, vol. 354:82-84 (1991).

Lania, Andrea, et al., "G protein mutations in endocrine diseases," European Journal of Endocrinology, vol. 145:543-559 (2001).

Lau, Nelson C. et al., "An Abundant Class of Tiny RNAs with Probable Regulatory Roles in Caenorhabditis elegans," Science, vol. 294:858-862 (2001).

Lee, Rosalind C. et al., "An Extensive Class of Small RNAs in Caenorhabditis elegans," Science, vol. 294:862-864 (2001).

Lee, Nan Sook et al., "Expression of small interfering RNAs targeted against HIV-1 rev transcripts in human cells," Nature Biotechnology, vol. 19:500-505 (2002).

Lee, Sang-Kyung et al., "Lentiviral delivery of short hairpin RNAs protects CD4 T cells from multiple clades and primary isolates of HIV," Blood, vol. 106(3):818-826 (2005).

Lee, Yoontae et al., "MicroRNA genes are transcribed by RNA polymerase II," The EMBO Journal, vol. 23:4051-4060 (2004).

Lee, Rosalind C. et al., "The C. elegans Heterochronic Gene lin-4 Encodes Small RNAs with Antisense Complementarity to lin-14," Cell, vol. 75:843-854 (1993).

Lee, Yoontae et al., "The nuclear RNase III Drosha initiates microRNA processing," Nature, vol. 425:415-419 (2003).

Lewis, Benjamin P. et al., "Conserved Seed Pairings, Often Flanked by Adenosines, Indicates that Thousands of Human Genes are MicroRNA Targets," Cell, vol. 120:15-20 (2005).

Lewis, Benjamin P. et al., "Prediction of Mammalian MicroRNA Targets," Cell, vol. 115:787-798 (2003).

Li, Zhaoyang et al., "Specific inhibition of HIV-1 replication by short hairpin RNAs targeting human cyclin T1 without inducing apoptosis," FEBS Letters, vol. 579:3100-3106 (2005).

Liang, Xue-hai et al., "Small nucleolar RNA interference induced by antisense or double-stranded RNA in trypanosomatids," PNAS, vol. 100(13):7521-7526 (2003).

Lieberman, Judy et al., "Interfering with disease: opportunities and roadblocks to harnessing RNA interference," Trends in Molecular Medicine, vol. 9(9):397-403 (2003).

Lim, Lee P. et al., "Microarray analysis shows that some microRNAs downregulate large numbers Of target mRNAs," Nature, vol. 433:769-773 (2005).

Lim, Lee P. et al., "The microRNAs of Caenorhabditis elegans," Genes & Development, vol. 17:991-1008 (2003).

Lim, Lee P. et al., "Vertebrate MicroRNA Genes," Science, vol. 299:1540 (2003).

Limbach, Patrick A. et al., "Summary; the modified nucleosides of RNA," Nucleic Acids Research, vol. 22(12):2183-2196 (1994).

Lipardi, Concetta et al., "RNAi as Random Degradative PCR: siRNA Primers Convert mRNA into dsRNAs that Are Degraded to Generate New siRNAs," Cell, vol. 107:297-307 (2001).

Liu, Qinghua et al., "R2D2, a Bridge Between the Initiation and Effector Steps of the Drosophila RNAi Pathway," Science, vol. 301:1921-1925 (2003).

Lorenz, Christina et al., "Steroid and lipid conjugates of siRNAs to enhance cellular uptake and gene silencing in liver cells," Bioorganic & Medicinal Chemistry Letters, vol. 14:4975-4977 (2004).

Lund, Elsebet et al., "Nuclear Export of MicroRNA Precursors," Science, vol. 303:95-98 (2004).

Luyten, Ingrid et al., "Hybridization properties of base-modified oligonucleotides within the double and triple helix motif," Eur. J. Med. Chem., vol. 33:515-576 (1998).

Mallory AC, Reinhart BJ, Jones-Rhoades MW, Tang G, Zamore PD, Barton MK, Bartel DP. MicroRNA control of PHABULOSA in leaf development: importance of pairing to the microRNA 5' region. EMBO J. Aug. 18, 2004;23(16):3356-64. Epub Jul. 29, 2004.

Manoharan, Muthiah et al., "Oligonucleotide Conjugates: Alteration of the Pharmacokinetic Properties of Antisense Agents," *Nucleoside & Nucleotides*, vol. 14(3-5):969-973 (1995).

Martinez, Javier et al., "Single-Stranded Antisense siRNAs Guide Target RNA Cleavage in RNAi," *Cell*, vol. 110:563-574 (2002).

Martinez, Luis Alfonso et al., "Synthetic small inhibiting RNAs: Efficient tools to inactivate oncogenic mutations and restore p53 pathways," *PNAS*, vol. 99(23):14849-14854 (2002).

Matz, Paul G. et al., "Cell Death After Exposure to Subarachnoid Hemolysate Correlates Inversely With Expression of CuZn-Superoxide Dismutase," *Stroke*, vol. 31:2450-2458 (2000).

Matzuk, Martin M. et al., "Ovarian Function in Superoxide Dismutase 1 and 2 Knockout Mice," *Endocrinology*, vol. 139(9):4008-4011 (1998).

Maxwell, Michele M. et al., "RNA interference-mediated silencing of mutant superoxide dismutase rescues cyclosporin A-induced death in cultured neuroblastoma cells," *PNAS*, vol. 101(9):3178-3183 (2004).

McCaffrey, Anton P. et al., "RNA interference in adult mice," *Nature*, vol. 418:38-39 (2002).

McFadden, Sandra L. et al., "Anatomical, Metabolic and Genetic Aspects of Age-related Hearing Loss in Mice," *Audiology*, vol. 40:313-321 (2001).

McManus, Michael T. et al., "Gene Silencing in Mammals by Small Interfering RNAs," *Nature Reviews Genetics*, vol. 3:737-747 (2002).

Meister, Gunter et al., "Sequence-specific inhibition of microRNA- and siRNA-induced RNA silencing," *RNA*, vol. 10:544-550 (2004).

Merriam-Webster online, "engineer," retrieved online at http://www.merriam-webster.com/dictonary (2008).

Merriam-Webster online, "pharmaceutical," retrieved online at http://www.merriam-webster.com/dictonary (2009).

Mi, Zhibao et al., "Characterization of a Class of Cationic Peptides Able to Facilitate Efficient Protein Transduction in Vitro and in Vivo," *Molecular Therapy*, vol. 2(4):339-347 (2000).

Miller, Victor M. et al., "Targeting Alzheimer's disease genes with RNA interference: an efficient strategy for silencing mutant alleles," *Nucleic Acids Research*, vol. 32(2):661-668 (2004).

Mitchell, D.J. et al., "Polyarginine enters cells more efficiently than other polycationic homopolymers," *J. Peptide Res.*, vol. 56:318-325 (2000).

Molecular Biology of the Cell, Fourth Edition, "DNA Replication Mechanisms," retrieved online at http://www.ncbi.nlm.nih.gov/books/bv.fcgi?highlight=DNA&rid=mboc4.section.754 (2008).

Molecular Biology of the Cell, Fourth Edition, "Figure 4-4," retrieved online at http://www.ncbi.nlm.nih.gov/books/bv.fcgi?rid=mboc4.figgrp (2008).

Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section165 (2008).

Molecular Biology of the Cell, Fourth Edition, "Wobble base-pairing between codons and anticodons," retrieved online at http://www.ncbi.nlm.nih.gov/books/bv.fcgi?highlight=inosine&rid=mboc4.figgrp.1058 (2008).

Moss, Eric G., "Silencing unhealthy alleles naturally," *Trends in Biotechnology*, vol. 21(5):185-187 (2003).

Moss, Eric G. et al., "The Cold Shock Domain Protein LIN-28 Controls Developmental Timing in *C. elegans* and Is Regulated by the *lin-4* RNA," *Cell*, vol. 88:637-646 (1997).

Mourelatos, Zissimos et al., "miRNPs: a novel class of ribonucleoproteins containing numerous microRNAs," *Genes & Development*, vol. 16:720-728 (2002).

Müller, Jørrn et al., "Severe testotoxicosis phentype associated with Asp$^{578}$→Tyr mutation of the lutrophin/choriogonadotrophin receptor gene," *J. Med. Genet.*, vol. 35:340-341 (1998).

Murchison, Elizabeth P. et al., "miRNAs on the move: miRNA biogenesis and the RNAi machinery," *Current Opinion in Cell Biology*, vol. 16:223-229 (2004).

Oldridge, Michael et al., "Dominant mutations in *ROR2*, encoding an orphan receptor tyrosine kinase, cause brachydactyly type B," *Nature Genetics*, vol. 24:275-278 (2000).

Olsen, Philip H. et al., "The *lin-4* Regulatory RNA Controls Developmental Timing in *Caenorhabditis elegans* by Blocking LIN-14 Protein Synthesis after the Initiation of Translation," *Developmental Biology*, vol. 216:671-680 (1999).

Opalinska, Joanna B. et al., "Nucleic Acid Therapeutic for Hematologic Malignancies—Theoretical Considerations," *Ann. N.Y. Acad. Sci.*, vol. 1082:124-136 (2006).

Opalinska, Joanna B. et al., "Nucleic-Acid Therapeutics: Basic Principles and Recent Applications," *Nature Reviews, Drug Discovery*, vol. 1:503-514 (2002).

Orrell, Richard W. et al., "Clinical implications of the genetics of ALS and other motor neuron diseases," *Neurology*, vol. 57:9-17 (2001).

Parrish, Susan et al., "Functional Anatomy of a dsRNA Trigger: Differential Requirement for the Two Trigger Strands in RNA Interference," *Molecular Cell*, vol. 6:1077-1087 (2000).

Persengiev, Stephan P. et al., "Nonspecific, concentration-dependent stimulation and repression of mammalian gene expression by small interfering RNAs (siRNAs)," *RNA*, vol. 10:12-18 (2004).

Pfister, Edith L. et al., "Five siRNAs Targeting Three SNPs May Provide Therapy for Three-Quarters Quarters of Huntington's Disease Patients," *Current Biology*, vol. 19:774-778 (2009).

Pooga, Margus et al., "Cell penetration by transportan," *FASEB J.*, vol. 12:67-77 (1998).

Poy, Matthew N. et al., "A pancreatic islet-specific microRNA regulates insulin secretion," *Nature*, vol. 432:226-230 (2004).

Pusch, Oliver et al., "Nucleotide sequence homology requirements of HIV-1-specific short hairpin RNA," *Nucleic Acids Research*, vol. 31(22):6444-6449 (2003).

Puttaparthi, Krishna et al., "Disease Progression in a Transgenic Model of Familial Amyotrophic Lateral Sclerosis Is Dependent on Both Neuronal and Non-Neuronal Zinc Binding Proteins," *The Journal of Neuroscience*, vol. 22(20):8790-8796 (2002).

Qin, Zheng-Hong et al., "Autophagy regulates the processing of amino terminal huntingtin fragments," *Human Molecular Genetics*, vol. 12(24):3231-3244 (2003).

Radunovic, Aleksandar et al., "ALSODatabase: Database of SOD1 (and other) gene mutations in ALS on the internet," *Amyot. Lat. Scler.*, vol. 1:45-49 (1999).

Ralph, G. Scott et al., "Silencing mutant SOD1 using RNAi protects against neurodegeneration and extends survival in an ALS model," *Nature Medicine*, vol. 11(4):429-433 (2005).

Raoul, Cédric et al., "Lentiviral-mediated silencing of SOD1 through RNA interference retards disease onset and progression in a mouse model of ALS," *Nature Medicine*, vol. 11(4):423-428 (2005).

Reinhart, Brenda J. et al., "MicroRNAs in plants," *Genes & Development*, vol. 16:1616-1626 (2002).

Reinhart, Brenda J. et al., "The 21-nucleotide *let-7* RNA regulates developmental timing in *Caenorhabditis elegans*," *Nature*, vol. 403:901-906 (2000).

Reynolds, Angela et al., "Rational siRNA design for RNA interference," *Nature Biotechnology*, vol. 22(3):326-330 (2004).

Rival, Thomas et al., "Decreasing Glutamate Buffering Capacity Triggers Oxidative Stress and Neuropil Degeneration in the Drosophila Brain," *Current Biology*, vol. 14:599-605 (2004).

Rose, Scott D. et al., "Functional polarity is introduced by Dicer processing of short substrate RNAs," *Nucleic Acids Research*, vol. 33(13):4140-4156 (2005).

Saenger, Wolfram, Principles of Nucleic Acid Struture, Springer-Verlag, New York, Charles R. Cantor (ed.) (1984).

Sahin-Tóth, Miklós et al., "Gain-of-Function Mutations Associated with Hereditary Pancreatitis Enhance Autoactivation of Human Cationic Trypsinogen," *Biochemical and Biophysical Research Communications*, vol. 278:286-289 (2000).

Savitt, Joseph M. et al., "Diagnosis and treatment of Parkinson disease: molecules to medicine," *The Journal of Clinical Investigation*, vol. 116(7):1744-1754 (2006).

Saxena, Sandeep et al., "Small RNAs with Imperfect Match to Endogenous mRNA Repress Translation," *The Journal of Biological Chemistry*, vol. 278(45):44312-44319 (2003).

Scadden, A.D.J. et al., "Editing of RNA reduces the production of siRNAs," *EMBO Reports*, vol. 21(12):1109-1111 (2001).

Scherer, Lisa J. et al., "Rapid Assessment of Anti-HIV siRNA Efficacy Using PCR-Derived Pol III shRNA Cassettes," *Molecular Therapy*, vol. 10(3):597-603 (2004).

Scherer, Lisa J. et al., "Recent Applications of RNAi in Mammalian Systems," *Current Pharmaceutical Biotechnology*, vol. 5:355-360 (2004).

Scherer, Lisa et al., "Therapeutic Applications of RNA Interference: Recent Advances in siRNA Design," *Advances in Genetics*, vol. 52:1-21 (2004).

Schmidt, Charlie, "Negotiating the RNAi patent thicket," *Nature Biotechnology*, vol. 25(3):273-275 (2007).

Schwarz, Dianne S. et al., "Asymmetry in the Assembly of the RNAi Enzyme Complex," *Cell*, vol. 115:199-208 (2003).

Schwarz, Dianne S. et al., "Evidence that siRNAs Function as Guides, Not Primers, in the Drosophila and Human RNAi Pathways," *Molecular Cell*, vol. 10:537-548 (2002).

Schwarz, Dianne S. et al., "The RNA-Induced Silencing Complex Is a $Mg^{2+}$-Dependent Endonuclease," *Current Biology*, vol. 14:787-791 (2004).

Schwarz, Dianne S. et al., "Why do miRNAs live in the miRNP?," *Genes & Development*, vol. 16:1025-1031 (2002).

Seggerson, Kathy et al., "Two Genetic Circuits Repress the *Caenorhabditis elegans* Heterochronic Gene *lin-28* after Translation Initiation," *Developmental Biology*, vol. 243:215-225 (2002).

Semizarov D, Frost L, Sarthy A, Kroeger P, Halbert DN, Fesik SW. Specificity of short interfering RNA determined through gene expression signatures. Proc Natl Acad Sci U S A. May 27, 2003;100(11):6347-52.

Shackel, Nick A. et al., "Intrahepatic Gene Silencing by RNA Interference," *Gastroenterology*, vol. 126(1):356-358 (2004).

Sharp, Phillip A. et al., "RNA Interference," *Science*, vol. 287:2431-2432 (2000).

Shefner, J.M. et al., "Mice lacking cytosolic copper/zinc superoxide dismutase display a distinctive motor axonopathy," *Neurology*, vol. 53:1239-1246 (1999).

Shi, Yang, "Mammalian RNAi for the masses," *Trends in Genetics*, vol. 19(1):9-12 (2003).

Slack, Frank J. et al., "The *lin-41* RBCC Gene Acts in the *C. elegans* Heterochronic Pathway between the *let-7* Regulatory RNA and the LIN-29 Transcription Factor," *Molecular Cell*, vol. 5:659-669 (2000).

Sledz, Carol A. et al., "Activation of the interferon system by short-interfering RNAs," *Nature Cell Biology*, vol. 5(9):834-838 (2003).

Siddique, Teepu et al., "Molecular genetic basis of familial ALS," *Neurology*, vol. 47(Suppl. 2):S27-S35 (1996).

Sijen, Titia et al., "On the Role of RNA Amplification in dsRNA-Triggered Gene Silencing," *Cell*, vol. 107:465-476 (2001).

Simeoni, Federica et al., "Insight into the mechanism of the peptide-based gene delivery system MPG: implications for delivery of siRNA into mammalian cells," *Nucleic Acids Research*, vol. 31(11):2717-2724 (2003).

Simon, E.S. et al., "Creutzfeldt-Jakob Disease Profile in Pateints Homozygous for the PRNP E200K Mutation," *Annals of Neurology*, vol. 47(2):257-260 (2000).

Snove, Ola Jr., et al., "Chemical Modifications Rescue Off-Target Effects of RNAi," *ACS Chemical Biology*, vol. 1(5):274-276 (2006).

Song, Erwei et al., "RNA interference targeting Fas protects mice from fulminant hepatitis," *Nature Medicine*, vol. 9(3):347-351 (2003).

Stark, Alexander et al., "Identification of Drosophila MicroRNA Targets," *PLOS Biology*, vol. 1(3):397-409 (2003).

Sundaralingam, Muttaiya et al., "Hydrogen and hydration of DNA and RNA oligonucleotides," *Biophysical Chemistry*, vol. 95:273-282 (2002).

Tabara, Hiroaki et al., "The dsRNA Binding Protein RDE-4 Interacts with RDE-1, DCR-1, and a DExH-Box Helicase to Direct RNAi in *C. elegans*," *Cell*, vol. 109:861-871 (2002).

Tabara, Hiroaki et al., "The *rde-1* Gene, RNA Interference and Transposon Silencing in *C. elegans*," *Cell*, vol. 99:123-132 (1999).

Tang, Guiliang et al., "A biochemical framework for RNA silencing in plants," *Genes & Development*, vol. 17:49-63 (2003).

Tang, Guiliang et al., "Biochemical Dissection of RNA Silencing in Plants," *Methods in Molecular Biology*, vol. 257:223-243 (2004).

Taylor, J. Paul et al., "Toxic Proteins in Neurodegenerative Disease," *Science*, vol. 296:1991-1995 (2002).

ten Asbroek, Anneloor L.M.A. et al., "Polymorphisms in the large subunit of human RNA polymerase II as target for allele-specific inhibition," *Nucleic Acids Research*, vol. 28(5):1133-1138 (2000).

Tijsterman, Marcel et al., "PPW-1, a PAZ/PIWI Protein Required for Efficient Germline RNAi, Is Defective in a Natural Isolate of *C. elegans*," *Current Biology*, vol. 12:1535-1540 (2002).

Tijsterman, Marcel et al., "RNA Helicase MUT-14-Dependent Gene Silencing Triggered in *C. elegans* by Short Antisense RNAs," *Science*, Vo. 295:694-697 (2002).

Tomari, Yukihide et al., "A Protein Sensor for siRNA Asymmetry," *Science*, vol. 306:1377-1380 (2004).

Tomari, Yukihide et al., "Perspective: machines for RNAi," *Genes & Development*, vol. 19:517-529 (2005).

Tomari, Yukihide et al., "RISC ASsembly Defects in the *Drosophila* RNAi Mutant *armitage*," *Cell*, vol. 116:831-841 (2004).

Tuschl, Thomas et al., "siRNAs and miRNAs," *Keystone Symposia*, Abstract Book (2004).

Tuschl, Thomas et al., "Small Interfering RNAs: A Revolutionary Tool for the Analysis of Gene Function and Gene Therapy," *Molecular Interventions*, vol. 2(3):158-167 (2002).

Vargason, Jeffrey M. et al., "Size selective recognition of siRNA by an RNA silencing suppressor," *Cell*, vol. 115:799-811 (2003).

Valdink, Jan H. et al., "The future of motor neuron disease," *J. Neurol.*, vol. 241:491-500 (2004).

Vella, Monica C. et al., "The *C. elegans* microRNA *let-7* binds to imperfect *let-7* complementary sites from the *lin-41* 3'UTR," *Genes & Development*, vol. 18:132-137 (2004).

Victor, Martin et al., "HAT activity is essential for CBP-1-dependent transcription and differentiation in *Caenorhabditis elegans*," *EMBO Reports*, vol. 31(1):50-55 (2002).

Vivès, Eric et al., "A Truncated HIV-1 Tat Protein Basic Domain Rapidly Translocates through the Plasma Membrane and Accumulates in the Cell Nucleus," *The Journal of Biological Chemistry*, vol. 272(25):16010-16017 (1997).

Wang, J. et al., "Fas siRNA Reduces Apoptotic Cell Death of Allogeneic-Transplanted Hepatocytes in Mouse Spleen," *Transplantation Proceedings*, Vo. 35:1594-1595 (2003).

Wianny, Florence et al., "Specific interference with gene function by double-stranded RNA in early mouse development," *Nature Cell Biology*, vol. 2:70-75 (2000).

Wightman, Bruce et al., "Posttranscriptional Regulation of the Heterochronic Gene *lin-14* by *lin-4* Mediates Temporal Pattern Formation in *C. elegans*," *Cell*, vol. 75:855-862 (1993).

Wikipedia, "Human genetic variation," obtained online at: http://en.wikipedia.org/wiki/Human_genetic-variation (2008).

Wu-Sharf, Dancia et al., "Transgene and Transposon Silencing in *Chlamydomonas reinhardtii* by a DEAH-Box RNA Helicase," *Science*, vol. 290:1159-1162 (2000).

Xia, Xu Gang et al., "An enhanced U6 promoter for synthesis of short hairpin RNA," *Nucleic Acids Research*, vol. 31(17):e100 (2003).

Xia, Xu Gang et al., "An RNAi strategy for treatment of amyotrophic lateral sclerosis caused by mutant Cu,Zn superoxide dismutase," *Journal of Neurochemistry*, vol. 92:362-367 (2005).

Xie, Zhongcong et al., "Effects of RNA Interference-mediated Silencing of γ-Secretase Complex Components on Cell Sensitivity to Caspase-3 Activation," *The Journal of Biological Chemistry*, vol. 279(33):34130-34137 (2004).

Xie, Jun et al., "RNAi knockdown of Par-4 inhibits neurosynaptic degeneration in ALS-linked mice," *Journal of Neurochemistry*, vol. 92:59-71 (2005).

Xu, Peizhang et al., "The *Drosophila* MicroRNA Mir-14 Suppresses Cell Death and Is Required for Normal Fat Metabolism," *Current Biology*, vol. 13:790-795 (2003).

Yi, Rui et al., "Exportin-5 mediates the nuclear export of pre-microRNAs and short hairpin RNAs," *Genes & Development*, vol. 17:3011-3016 (2003).

Zeng, Yan et al., "MicroRNAs and small interfering RNAs can inhibit mRNA expression by similar mechanisms," *PNAS*, vol. 100(17):9779-9784 (2003).

Zeng, Yan et al, "Sequence requirements for micro RNA processing and function in human cells," *RNA*, vol. 9:112-123 (2003).

Zeng, Yan et al., "Structural requirements for pre-microRNA binding and nuclear export by Exportin 5," *Nucleic Acids Research*, vol. 32(16):4776-4785 (2004).

Zhang, Yingjie et al., "Engineering Mucosal RNA Interference in Vivo," *Molecular Therapy*, vol. 14(3):336-342 (2006).

Zhang, Haidi et al., "Human Dicer preferentially cleaves dsRNAs at their termini without a requirement for ATP," *The EMBO Journal*, vol. 21(21):5875-5885 (2002).

Zhou, Hongxia et al., "An RNA polymerase II construct synthesizes short-hairpin RNA with a quantitative indicator and mediates highly efficient RNAi," *Nucleic Acids Research*, vol. 33(6):e62 (2005).

Zimmermann, Tracy S. et al, "RNAi-mediated Gene Silencing in Non-human Primates," *Nature*, vol. 441, 111-114 (2006).

Zitzmann, Sabine et al., "Arginine-Glycine-Aspartic Acid (RGD)-Peptide Binds to Both Tumor and Tumor-Endothelial Cells in Vivo," *Cancer Research*, vol. 62:5139-5143 (2002).

Zuccato, Chiara et al., "Loss of Huntingtin-Mediated BDNF Gene Transcription in Huntington's Disease," *Science*, vol. 293:493-498 (2001).

Invitation to Pay Additional Fees for Application No. PCT/US2005/029011, dated Feb. 20, 2006.

International Search Report for Application No. PCT/US2005/029011, dated Apr. 13, 2006.

Supplementary Partial European Search Report for Application No. 04753972, dated Oct. 31, 2006.

International Preliminary Report on Patentability for Application No. PCT/US2006/038704, dated Apr. 2, 2008.

International Search Report for Application No. PCT/US07/02324, dated Nov. 20, 2008.

Supplementary European Search Report for Application No. 06836174, dated Dec. 10, 2008.

European Office Action for Application No. 047783980, dated Sep. 29, 2009.

\* cited by examiner

FIG.1A

```
   1 TTGCTGTGTG AGGCAGAACC TGCGGGGGCA GGGGCGGGCT GGTTCCCTGG CCAGCCATTG
  61 GCAGAGTCCG CAGGCTAGGG CTGTCAATCA TGCTGGCCGG CGTGGCCCCG CCTCCCGCGG
 121 CGCGGCCCCG CCTCCGCCGG CGCACGTCTG GGACGCAAGG CGCCGTGGGG GCTGCCGGGA
 181 CGGGTCCAAG ATGGACGGCC GCTCAGGTTC TGCTTTTACC TGCGGCCCAG AGCCCCATTC
 241 ATTGCCCCGG TGCTGAGCGG CGCCGCGAGT CGGCCCGAGG CCTCCGGGGA CTGCCGTGCC
 301 GGGCGGGAGA CCGCC▓GC GACCCTGGAA AAGCTGATGA AGGCCTTCGA GTCCCTCAAG
 361 TCCTTCCAGC AGCAGCAGCA GCAGCAGCAG CAGCAGCAGC AGCAGCAGCA GCAGCAGCAG
 421 CAGCAGCAGC AACAGCCGCC ACCGCCCCCG CCGCCCCCGC CGCCTCCCTCA GCTTCCTCAG
 481 CCGCCGCCGC AGGCACAGCC GCTGCTGCCT CAGCCGCAGC CGCCCCCGCC GCCGCCCCCG
 541 CCGCCACCCG GCCCGGCTGT GGCTGAGGAG CCGCTGCACC GACCAAAGAA AGAACTTTCA
 601 GCTACCAAGA AAGACCGTGT GAATCATTGT CTGACAATAT GTGAAAACAT AGTGGCACAG
 661 TCTGTCAGAA ATTCTCCAGA ATTTCAGAAA CTTCTGGGCA TCGCTATGGA ACTTTTTCTG
 721 CTGTGCAGTG ATGACGCAGA GTCAGATGTC AGGATGGTGG CTGACGAATG CCTCAACAAA
 781 GTTATCAAAG CTTTGATGGA TTCTAATCTT CCAAGGTTAC AGCTCGAGCT CTATAAGGAA
 841 ATTAAAAAGA ATGGTGCCCC TCGGAGTTTG CGTGCTGCCC TGTGGAGGTT TGCTGAGCTG
 901 GCTCACCTGG TTCGGCCTCA GAAATGCAGG CCTTACCTGG TGAACCTTCT GCCGTGCCTG
 961 ACTCGAACAA GCAAGAGACC CGAAGAATCA GTCCAGGAGA CCTTGGCTGC AGCTGTTCCC
1021 AAAATTATGG CTTCTTTTGG CAATTTTGCA AATGACAATG AAATTAAGGT TTTGTTAAAG
1081 GCCTTCATAG CGAACCTGAA GTCAAGCTCC CCCACCATTC GGCGGACAGC GGCTGGATCA
1141 GCAGTGAGCA TCTGCCAGCA CTCAAGAAGG ACACAATATT TCTATAGTTG GCTACTAAAT
1201 GTGCTCTTAG GCTTACTCGT TCCTGTGTCG GATGAACACT CCACTCTGCT GATTCTTGGC
```

FIG.1B

```
1261  GTGCTGCTCA CCCTGAGGTA TTTGGTGCCC TTGCTGCAGC AGCAGGTCAA GGACACAAGC
1321  CTGAAAGGCA GCTTCGGAGT GACAAGGAAA GACAAGGAAG TCTCTCCTTC TGCAGAGCAG
1381  CTTGTCCAGG TTTATGAACT GACGTTACAT CATACACAGC ACCAAGACCA CAATGTTGTG
1441  ACCGGAGCCC TGGAGCTGTT GCAGCAGCTC TTCAGAACGC CTCCACCCGA GCTTCTGCAA
1501  ACCCTGACCG CAGTCGGGGG CATTGGGCAG CTCACCGCTG CTAAGGAGGA GTCTGGTGGC
1561  CGAAGCCGTA GTGGGAGTAT TGTGGAACTT ATAGCTGGAG GGGGTTCCTC ATGCAGCCCT
1621  GTCCTTTCAA GAAAACAAAA AGGCAAAGTG CTCTTAGGAG AAGAAGAAGC CTTGGAGGAT
1681  GACTCTGAAT CGAGATCGGA TGTCAGCAGC TCTGCCTTAA CAGCCTCAGT GAAGGATGAG
1741  ATCAGTGGAG AGCTGGCTGC TTCTTCAGGG GTTTCCACTC CAGGGTCAGC AGTCATGAC
1801  ATCATCACAG AACAGCCACG GTCACAGCAC ACACTGCAGG CGGACTCAGT GGATCTGGCC
1861  AGCTGTGACT TGCCACTGAT GGGGATGAGG AGGATATCTT GAGCCACAGC
1921  TCCAGCCAGG TCAGCGCCGT CCCATCTGAC CCTGCCATGG ACCTGAATGA TGGACCCAG
1981  GCCTCGTCGC CCATCAGCGA CAGCTCCCAG ACCACCACCG AAGGGCCTGA TTCAGCTGTT
2041  ACCCCTTCAG ACAGTTCTGA AATTGTGTTA GACGGTACCG ACAACCAGTA TTTGGCCTG
2101  CAGATTGGAC AGCCCCAGGA TGAAGATGAG GAAGCCACAG GTATTCTTCC TGATGAAGCC
2161  TCGGAGGCCT TCAGGAACTC TTCCATGGCC CTTCAACAGG CACATTATTT GAAAAAACATG
2221  AGTCACTGCA GGCAGCCCTTC TGACAGCAGT GTTGATAAAT TTGTGTTGAG AGATGAAGCT
2281  ACTGAACCGG GTGATCAAGA AAACAAGCCT TGCCGCATCA AAGGTGACAT TGGACAGTCC
2341  ACTGATGATG ACTCTGCACC TCTTGTCCAT TGTGTCCGCC TTTTATCTGC TTCGTTTTTG
2401  CTAACAGGGG GAAAAAATGT GCTGGTTCCG GACAGGGATG TGAGGGTCAG CGTGAAGCC
2461  CTGGCCCTCA GCTGTGTGGG AGCAGCTGTG GCCCTCCACC CGGAATCTTT CTTCAGCAAA
```

FIG.1C

```
2521  CTCTATAAAG  TTCCTCTTGA  CACCACGGAA  TACCCTGAGG  AACAGTATGT  CTCAGACATC
2581  TTGAACTACA  TCGATCATGG  AGACCCACAG  GTTCGAGGAG  CCACTGCCAT  TCTCTGTGGG
2641  ACCCTCATCT  GCTCCATCCT  CAGCAGGTCC  CGCTTCCACG  TGGGAGATTG  GATGGGCACC
2701  ATTAGAACCC  TCACAGAAAA  TACATTTTCT  TTGGCGGATT  GCATTCCTTT  GCTGCGGAAA
2761  ACACTGAAGG  ATGAGTCTTC  TGTTACTTGC  AAGTTAGCTT  GTACAGCTGT  GAGGAACTGT
2821  GTCATGAGTC  TCTGCAGCAG  CAGCTACAGT  GAGTTAGGAC  TGCAGCTGAT  CATCGATGTG
2881  CTGACTCTGA  GGAACAGTTC  CTATTGGCTG  GTGAGGACAG  AGCTTCTGGA  AACCCTTGCA
2941  GAGATTGACT  TCAGGCTGGT  GAGCTTTTTG  GAGGCAAAAG  CAGAAAACTT  ACACAGAGGG
3001  GCTCATCATT  ATACAGGGCT  TTTAAAACTG  TGCTCAATAA  TGTTGTCATC
3061  CATTTGCTTG  GAGATGAAGA  CCCCAGGGTG  CGACATGTTG  CCGCAGCATC  ACTAATTAGG
3121  CTTGTCCCAA  AGCTGTTTTA  TAAATGTGAC  CAAGGACAAG  CTGATCCAGT  AGTGGCCGTG
3181  GCAAGAGATC  AAAGCAGTGT  TTACCTGAAA  CTTCTCATGC  ATGAGACGCA  GCCTCCATCT
3241  CATTTCTCCG  TCAGCACAAT  AACCAGAATA  TATAGAGGCT  ATAACCTACT  ACCAAGCATA
3301  ACAGACGTCA  CTATGGAAAA  TAACCTTTCA  AGAGTTATTG  CAGCAGTTTC  TCATGAACTA
3361  ATCACATCAA  CCACCAGAGC  ACTCACATTT  GGATGCTGTG  AAGCTTTGTG  TCTTCTTTCC
3421  ACTGCCTTCC  CAGTTTGCAT  TGGAGTTTA  GGTTGGCACT  GTGGAGTGCC  TCCACTGAGT
3481  GCCTCAGATG  AGTCTAGGAA  GAGCTGTACC  GTTGGGATGG  CCACAATGAT  TCTGACCCTG
3541  CTCTCGTCAG  CTTGGTTCCC  ATTGGATCTC  TCAGCCCATC  AAGATGCTTT  GATTTTGGCC
3601  GGAAACTTGC  TTGCAGCCAG  TGCTCCCAAA  TCTCTGAGAA  GTTCATGGGC  CTCTGAAGAA
3661  GAAGCCAACC  CAGCAGCCAC  CAAGCAAGAG  GAGGTCTGGC  CAGCCCTGGG  GGACCGGGCC
3721  CTGGTGCCCA  TGGTGGAGCA  GCTCTTCTCT  CACCTGCTGA  AGGTGATTAA  CATTTGTGCC
```

FIG.1D

```
3781 CACGTCCTGG ATGACGTGGC TCCTGGACCC GCAATAAAGG CAGCCCTTGCC TTCTCTAACA
3841 AACCCCCCTT CTCTAAGTCC CATCCGACGA AAGGGGAAGG AGAAAGAACC AGGAGAACAA
3901 GCATCTGTAC CGTTGAGTCC CAAGAAAGGC AGTGAGGCCA GTGCAGCTTC TAGACAATCT
3961 GATACCTCAG GTCCTGTTAC AACAAGTAAA TCCTCATCAC TGGGGAGTTT CTATCATCTT
4021 CCTTCATACC TCAAAACTGCA TGATGTCCTG AAAGCTACAC ACGCTAACTA CAAGGTCACG
4081 CTGGATCTTC AGAACAGCAC GGAAAAGTTT GGAGGGTTTC TCCGCTCAGC CTTGGATGTT
4141 CTTTCTCAGA TACTAGAGCT GGCCACACTG CAGGACATTG GGAAGTGTGT TGAAGAGATC
4201 CTAGGATACC TGAAATCCTG CTTTAGTCGA GAACCAATGA TGGCAACTGT TTGTGTTCAA
4261 CAATTGTTGA AGACTCTCTT TGGCACACAC TTGGCCTCCC AGTTTGATGG CTTATCTTCC
4321 AACCCCAGCA AGTCACAAGG CCGAGCACAG CGCCTTGGCT CCTCCAGTGT GAGGCCAGGC
4381 TTGTACCACT ACTGCTTCAT GGCCCCGTAC ACCCACTTCA CCCAGGCCCT CGCTGACGCC
4441 AGCCTGAGGA ACATGGTGCA GGCGGAGCAG CCTCGGGATG GTTTGATGTC
4501 CTCCAGAAAG TGTCTACCCA GTTGAAGACA AACCCTCACGA GTGTCACAAA GAACCGTGCA
4561 GATAAGAATG CTATTCATAA TCACATTCGT TTGTTTGAAC CTCTTGTTAT AAAAGCTTTA
4621 AAACAGTACA CGACTACAAC ATGTGTGCAG TTACAGAAGC AGGTTTTAGA TTTGCTGGCG
4681 CAGCTGGTTC AGTTACGGGT TAATTACTGT CTTCTGGATT CAGATCAGGT GTTTATTGGC
4741 TTTGTATTGA AACAGTTTGA ATACATTGAA GTGGGCCAGT TCAGGGAATC AGAGGCAATC
4801 ATTCCAAACA TCTTTTTCTT CTTGGTATTA CTATCTTATG AACGCTATCA TTCAAAACAG
4861 ATCATTGGAA TTCCTAAAAT CATTCAGCTC TGTGATGGCA TCATGGCCAG TGGAAGGAAG
4921 GCTGTGACAC ATGCCATACC GGCTCTGCAG CCCATAGTCC ACGACCTCTT TGTATTAAGA
4981 GGAACAAATA AAGCTGATGC AGGAAAAGAG CTTGAAACCC AAAAAGAGGT GGTGGTGTCA
```

```
5041  ATGTTACTGA GACTCATCCA GTACCATCAG GTGTTGGAGA TGTTCATTCT TGTCCTGCAG
5101  CAGTGCCACA AGGAGAATGA AGACAAGTGG AGACGACTGT CTCGACAGAT AGCTGACATC
5161  ATCCTCCCAA TGTTAGCCAA ACAGCAGATG CACATTGACT CTCATGAAGC CCTTGGAGTG
5221  TTAAATACAT TATTTGAGAT TTTGGCCCCT TCCTCCCTCC GTCCGGTAGA CATGCTTTTA
5281  CGGAGTATGT TCGTCACTCC AAACACAATG GCGTCCGTGA GCACTGTTCA ACTGTGGATA
5341  TCGGGAATTC TGGCCATTTT GAGGGTTCTG ATTTCCCAGT CAACTGAAGA TATTGTTCTT
5401  TCTCGTATTC AGGAGCTCTC CTTCTCTCCG TATTTAATCT CCTGTACAGT AATTAATAGG
5461  TTAAGAGATG GGGACAGTAC TTCAACGCTA GAAGAACACA GTGAAGGGAA ACAAATAAAG
5521  AATTTGCCAG AAGAAACATT TTCAAGGTTT CTATTACAAC TGGTTGGTAT TCTTTTAGAA
5581  GACATTGTTA CAAAACAGCT GAAGGTGGAA ATGAGTGAGC AGCAACATAC TTTCTATTGC
5641  CAGGAACTAG GCACACTGCT AATGTGTCTG ATCCACATCT TCAAGTCTGG AATGTTCCGG
5701  AGAATCACAG CAGCTGCCAC TAGGCTGTTC CGCAGTGATG GCTGTGGGCG CAGTTTCTAC
5761  ACCCTGGACA GCTTGAACTT GCGGGGCTCG TCCATGATCA CCACCCACCC GGCCCTGGTG
5821  CTGCTCTGGT GTCAGATACT GCTGCTTGTC AACCACACCG ACTACCGCTG GTGGGCAGAA
5881  GTGCAGCAGA CCCCGAAAAG ACACAGTCTG TCCAGCACAA AGTTACTTAG TCCCCAGATG
5941  TCTGGAGAAG AGGAGGATTC TGACTTGGCA GCCAAACTTG GAATGTGCAA TAGAGAAATA
6001  GTACGAAGAG GGGCTCTCAT TCTCTTCTGT GTCAGAACCT CCATGACTCC
6061  GAGCACTTAA CGTGCCGTT CAGTGCCGTT TGTAAATCAC ATTCAAGATC TGATCAGCCT TTCCCACGAG
6121  CCTCCAGTAC AGGACTTCAT CAGTGCCGTT CATCGGAACT CTTTCAACTC CAACCATGCT CGGCCTGTTC
6181  ATCCAGGCAA TTCAGTCTCG TTGTGAAAAC CTTTCAACTC CAACCATGCT GAAGAAAACT
6241  CTTCAGTGCT TGGAGGGGAT CCATCTCAGC CAGTCGGGAG CGTGCTCAC GCTGTATGTG
```

```
6301 GACAGGCTTC TGTGCACCCC TTTCCGTGTG CTGGCTCGCA TGGTCGACAT CCTTGCTTGT
6361 CGCCGGGTAG AAATGCTTCT GGCTGCAAAT TTACAGAGCA GCATGGCCCA GTTGCCAATG
6421 GAAGAACTCA ACAGAATCCA GGAATACCTT CAGAGCAGCG GGCTCGCTCA GAGACACCAA
6481 AGGCTCTATT CCCTGCTGGA CAGGTTTCGT CTCTCCACCA TGCAAGACTC ACTTAGTCCC
6541 TCTCCTCCAG TCTCTTCCCA CCCGCTGGAC GGGGATGGGC ACGTGTCACT GGAAACAGTG
6601 AGTCCGGACA AAGACTGGTA CGTTCATCTT GTCAAATCCC AGTGTTGGAC CAGGTCAGAT
6661 TCTGCACTGC TGGAAGGTGC AGAGCTGGTG AATCGGATTC CTGCTGAAGA TATGAATGCC
6721 TTCATGATGA ACTCGGAGTT CAACCTAAGC CTGCTAGCTC CATGCTTAAG CCTAGGGATG
6781 AGTGAAATTT CTGGTGGCCA GAAGAGTGCC CTTTTTGAAG CAGCCCGTGA GGTGACTCTG
6841 GCCCGTGTGA GCGGCACCGT GCAGCAGCTC CCTGCTGTCC ATCATGTCTT CCAGCCCGAG
6901 CTGCCTGCAG AGCCGGCGGC CTACTGGAGC AAGTTGAATG ATCTGTTTGG GGATGCTGCA
6961 CTGTATCAGT CCCTGCCCAC TCTGGCCCGG GCCCTGGCAC AGTACCTGGT GGTGGTCTCC
7021 AAACTGCCCA GTCATTTGCA CCTTCCTCCT GAGAAAGAGA AGGACATTGT GAAATTCGTG
7081 GTGGCAACCC TTGAGGCCCT GTCCTGGCAT TTGATCCATG AGCAGATCCC GCTGAGTCTG
7141 GATCTCCAGG CAGGGCTGGA CTGCTGCTGC CTGGCCCTGC AGCTGCCTGG CCTCTGGAGC
7201 GTGGTCTCCT CCACAGAGTT TGTGACCCAC GCCTGCTCCC TCATCTACTG TGTGCACTTC
7261 ATCCTGGAGG CCGTTGCAGT GCAGCCTGGA GAGCAGCTTC TTAGTCCAGA AAGAAGGACA
7321 AATACCCAA AAGCCATCAG CGAGGAGGAG GAGGAAGTAG ATCCAAACAC ACAGAATCCT
7381 AAGTATATCA CTGCAGCCTG TGAGATGGTG GCAGAAATGG TGGAGTCTCT GCAGTCGGTG
7441 TTGGCCTTGG GTCATAAAAG GAATAGCGGC GTGCCGGCGT TTCTCACGCC ATTGCTCAGG
7501 AACATCATCA TCAGCCTGGC CCGCCTGCCC CTTGTCAACA GCTACACACG TGTGCCCCCA
```

FIG.1G

```
7561  CTGGTGTGGA AGCTTGGATG GTCACCCAAA CCGGGAGGGG ATTTTGGCAC AGCATTCCCT
7621  GAGATCCCCG TGGAGTTCCT CCAGAAAAG GAAGTCTTTA AGGAGTTCAT CTACCGCATC
7681  AACACACTAG GCTGGACCAG TCGTACTCAG TTTGAAGAAA CTTGGGCCAC CCTCCTTGGT
7741  GTCCTGGTGA CGCAGCCCCT CGTGATGGAG CAGGAGGAGA GCCCACCAGA AGAAGACACA
7801  GAGAGGACCC AGATCAACGT CCTGGCCGTG CAGGCCATCA CCTCACTGGT GCTCAGTGCA
7861  ATGACTGTGC CTGTGCCCGG CAACCCAGCT GTAAGCTGCT TGGAGCAGCA GCCCCGGAAC
7921  AAGCCTCTGA AAGCTCTCGA CACCAGGTTT GGGAGGAAGC TGAGCATTAT CAGAGGGATT
7981  GTGGAGCAAG AGATTCAAGC AATGGTTTCA ATATTGCCAC CCATCATTTA
8041  TATCAGGCAT GGGATCCTGT CCCTTCTCTG TCTCCGGCTA CTACAGGTGC CCTCATCAGC
8101  CACGAGAAGC TGCTGCTACA GATCAACCCC GAGCGGGGAG TGGGGAGCAT GAGCTACAAA
8161  CTCGGCCAGG TGTCCATACA CTCCGTGTGG CTGGGGAACA GCATCACACC CCTGAGGGAG
8221  GAGGAATGGG ACGAGGAAGA GGAGGAGGAG GCCGACGCCC CTGCACCTTC GTCACCACCC
8281  ACGTCTCCAG TCAACTCCAG GAAACACCGG GCTGGAGTTG ACATCCACTC CTGTTCGCAG
8341  TTTTTGCTTG AGTTGTACAG CCGGCTGGATC GCTCAGCCAG GAGGACCCCG
8401  GCCATCCTGA TCAGTGAGGT GGTCAGGGT TCTCAGACTT GTTCACCGAG
8461  CGCAACCAGT TTGAGCTGAC GTATGTGACG CTGACAGAAC TGCGAAGGGT GCACCCTTCA
8521  GAAGACGAGA TCCTCGCTCA GTACCTGGTG CCTGCCACCT GCAAGGCCAG TGCCGTCCTT
8581  GGGATGGACA AGGCCGTGGC GGAGCCTGTC AGCCGCCTGC TGGAGAGCAC GCTCAGGAGC
8641  AGCCACCTGC CCAGCAGGGT TGGAGCCCTG CACGGCGTCC TCTATGTGCT GGAGTGCGAC
8701  CTGCTGGACG ACACTGCCAA GCAGCTCATC CCGGTCATCA GCGACTATCT CCTCTCCAAC
8761  CTGAAAGGGA TCGCCCACTG CGTGAACATT CACAGCCAGC AGCACGTACT GGTCATGTGT
```

```
8821  GCCACTGCGT TTTACCTCAT TGAGAACTAT CCTCTGGACG TAGGGCCGGA ATTTTCAGCA
8881  TCAATAATAC AGATGTGTGG GGTGATGCTG TCTGGAAGTG AGGAGTCCAC CCCCTCCATC
8941  ATTTACCACT GTGCCCTCAG AGGCCTGGAG CGCCTCCTGC TCTCTGAGCA GCTCTCCCGC
9001  CTGGATGCAG AATCGCTGGT CAAGCTGAGT GTGGACAGAG TGAACGTGCA CAGCCCGCAC
9061  CGGGCCATGG CGGCTCTGGG CCTGATGCTC ACCTGCATGT ACACAGGAAA GGAGAAAGTC
9121  AGTCCGGGTA GAACTTCAGA CCCTAATCCT GCAGCCCCCG ACAGGCGAGTC AGTGATTGTT
9181  GCTATGGAGC GGGTATCTGT TCTTTTTGAT AGGATCAGGA AAGGCTTTCC TTGTGAAGCC
9241  AGAGTGGTGG CCAGGATCCT GCCCCAGTTT CTAGACGACT TCTTCCCACC CCAGGACATC
9301  ATGAACAAAG TCATCGGAGA GTTTCTGTCC AACCAGCAGC CATACCCCCA GTTCATGGCC
9361  ACCGTGGTGT ATAAGGTGTT TCAGACTCTG CACAGCACCG GGCAGTCGTC CATGGTCCGG
9421  GACTGGGTCA TGCTGTCCCT CTCCAACTTC ACGCAGAGGG CCCCGGTCGC CATGGCCACG
9481  TGGAGCCTCT CCTGCTTCTT TGTCAGCGCG TCCACCAGCC CGTGGGTCGC GGCGATCCTC
9541  CCACATGTCA TCAGCAGGAT GGGCAAGCTG ACACCAGATA GAGCAGGTGG ACGTGAACCT TTTCTGCCTG
9601  GTCGCCACAG ACTTCTACAG ACACCAGATA GAGGAGGAGC TCGACCGCAG GGCCTTCCAG
9661  TCTGTGCTTG AGTGGTTGC AGCCCCAGGA AGCCCATATC ACCGGCTGCT GACTTGTTTA
9721  CGAAATGTCC ACAAGGTCAC CACCTGC GCGCCATGGT GGGAGAGACT GTGAGGCGGC
9781  AGCTGGGGGC GGAGCCTTTG GAAGTCTGTG CCCTTGTGCC CTGCCTCCAC CGAGCCAGCT
9841  TGGTCCCTAT GGGCTTCCGC ACATGCCGCG GGGGCCAGG CAACGTGCGT GTCTCTGCCA
9901  TGTGGCAGAA GTGCTCTTTG TGGCAGTGGC CAGGCAGGGA GTGTCTGCAG TCCTGGTGGG
9961  GCTGAGCCTG AGGCCTTCCA GAAAGCAGGA GCAGCTGTGC TGCACCCCAT GTGGGTGACC
10021 AGGTCCTTTC TCCTGATAGT CACCTGCTGG GTTGCAGCTG CTCTTGCATC
```

```
10081  TGGGCCAGAA GTCCTCCCTC CTGCAGGCTG GCTGTTGGCC CCTCTGCTGT CCTGCAGTAG
10141  AAGGTGCCGT GAGCAGGCTT TGGGAACACT GGCCTGGGTC TCCCTGGTGG GGTGTGCATG
10201  CCACGCCCCG TGTCTGGATG CACAGATGCC ATGGCCTGTG CTGGGCCAGT GGCTGGGGGT
10261  GCTAGACACC CGGCACCATT CTCCCTTCTC TCTTTTCTTC TCAGGATTTA AAATTTAATT
10321  ATATCAGTAA AGAGATTAAT TTTAACGAAC TCTTTCTATG CCCGTGTAAA GTATGTGAAT
10381  CGCAAGGCCT GTGCTGCATG CGACAGCGTC CGGGGTGGTG GACAGGGCCC CCGGCCACGC
10441  TCCCTCTCCT GTAGCCACTG GCATAGCCCT CCTGAGCACC CGCTGACATT TCCGTTGTAC
10501  ATGTTCCTGT TTATGCATTC ACAAGGTGAC TGGGATGTAG AGAGGCGTTA GTGGGCAGGT
10561  GGCCACAGCA CAGGCCCCCA TTATCCTAGG GGTGCGCTCA ACTGCAGCCC
10621  CTCCCTCCTCG GGCACAGACG ACTGTCGTTC TCCACCCACC AGTCAGGGAC AGCAGCCTCC
10681  CTGTCACTCA GCTGAGAAGG CCAGCCCCTC CTGGCTGTGA GCAGCCTCCA CTGTGTCCAG
10741  AGACATGGGC CTCCCACTCC TGTTCCTTGC TAGCCCTGGG GTGGCGTCTG CCTAGGAGCT
10801  GGCTGGCAGG TGTTGGGACC TGCTGCTCCA TGGATGCATG CCCTAAGAGT GTCACTGAGC
10861  TGTGTTTTGT CTGAGCCTCT CTCGGTCAAC AGCAAAGCTT GGTGTCTTGG CACTGTTAGT
10921  GACAGAGCCC AGCATCCCTT CTGCCCCCGT TCCAGCTGAC ATCTTGCACG GTGACCCCTT
10981  TTAGTCAGGA GAGTGCAGAT CTGTGCTCAT CGGAGACTGC CCCACGGCCC TGTCAGAGCC
11041  GCCACTCCTA TCCCCAGGAC AGGTCCCTGG ACCAGCCTCC TGTTTGCAGG CCCAGAGGAG
11101  CCAAGTCATT AAAATGGAAG TGGATTCTGG ATGGCCGGGC TGCTGCTGAT GTAGGAGCTG
11161  GATTTGGGAG CTCTGCTTGC CGACTGGCTG TGAGACGAGG CAGGGCTCT GCTTCCTCAG
11221  CCCTAGAGGC GAGCCAGGCA AGGTTGGCGA CTGTCATGTG GCTTGGTTTG GTCATGCCCG
11281  TCGATGTTTT GGGTATTGAA TGTGGTAAGT GGAGGAAATG TTGGAACTCT GTGCAGGTGC
```

```
11341  TGCCTTGAGA  CCCCCAAGCT  TCCACCTGTC  CCTCTCCTAT  GTGGCAGCTG  GGGAGCAGCT
11401  GAGATGTGGA  CTTGTATGCT  GCCCACATAC  GTGAGGGGGA  GCTGAAAGGG  AGCCCCTGCT
11461  CAAAGGGAGC  CCCTCCTCTG  AGCAGCCTCT  GCCAGGCCTG  TATGAGGCTT  TTCCCACCAG
11521  CTCCCAACAG  AGGCCCTCCC  CAGCCAGGAC  CACCTCGTCC  TCGTGGCGGG  GCAGCAGGAG
11581  CGGTAGAAAG  GGGTCCGATG  TTTGAGGAGG  CCCTTAAGGG  AAGCTACTGA  ATTATAACAC
11641  GTAAGAAAAT  CACCATTCTT  CCGTATTGGT  TGGGGGCTCC  TGTTTCTCAT  CCTAGCTTTT
11701  TCCTGGAAAA  GCCCGCTAGA  AGGTTTGGGA  ACGAGGGGAA  AGTTCTCAGA  ACTGTTGCTG
11761  CTCCCCACCC  GCCTCCCGCC  TCCCCCGCAG  GTTATGTCAG  CAGCTCTGAG  ACAGCAGTAT
11821  CACAGGCCAG  ATGTTGTTCC  TGGCTAGATG  TTTACATTTG  TAAGAAATAA  CACTGTGAAT
11881  GTAAAACAGA  GCCATTCCCT  TGGAATGCAT  ATCGCTGGGC  TCAACATAGA  GTTTGTCTTC
11941  CTCTTGTTTA  CGACGTGATC  TAAACCAGTC  CTTAGCAAGG  GGCTCAGAAC  ACCCCGCTCT
12001  GGCAGTAGGT  GTCCCCCACC  CCCAAAGACC  TGCCTGTGTG  CTCCGGAGAT  GAATATGAGC
12061  TCATTAGTAA  AAATGACTTC  ACCCACGCAT  ATACATAAAG  TATCCCATGCA  TGTGCATATA
12121  GACACATCTA  TAATTTTACA  CACACACCTC  TCAAGACGGA  GATGCATGGC  CTCTAAGAGT
12181  GCCCGTGTCG  GTTCTTCCTG  GAAGTTGACT  TTCCTTAGAC  CCGCCAGGTC  AAGTTAGCCG
12241  CGTGACGGAC  ATCCAGGCGT  GGGACGTGGT  CAGGGCAGGG  CTCATTCATT  GCCCACTAGG
12301  ATCCCACTGG  CGAAGATGGT  CTCCATATCA  GCTCTCTGCA  GAAGGGAGGA  AGACTTTATC
12361  ATGTTCCTAA  AAATCTGTGG  CAAGCACCCA  TCGTATTATC  CAAATTTTGT  TGCAAATGTG
12421  ATTAATTTGG  TTGTCAAGTT  TTGGGGGTGG  GCTGTGGGGA  GATTGCTTTT  GTTTTCCTGC
12481  TGGTAATATC  GGGAAAGATT  TTAATGAAAC  CAGGGTAGAA  TTGTTTGGCA  ATGCACTGAA
12541  GCGTGTTTCT  TTCCCAAAAT  GTGCCTCCCT  TCCGCTGCGG  GCCCAGCTGA  GTCTATGTAG
```

```
12601 GTGATGTTTC CAGCTGCCAA GTGCTCTTTG TTACTGTCCA CCCTCATTTC TGCCAGCGCA
12661 TGTGTCCTTT CAAGGGGAAA ATGTGAAGCT GAACCCCCTC CAGACACCCA GAATGTAGCA
12721 TCTGAGAAGG CCCTGTGCCC TAAAGGACAC CCCTCGCCCC CATCTTCATG GAGGGGTCA
12781 TTTCAGAGCC CTCGGAGCCA ATGAACAGCT CCTCCTCTTG GAGCTGAGAT GAGCCCCACG
12841 TGGAGCTCGG GACGGATAGT AGACAGCAAT AACTCGGTGT GTGGCCGCCT GGCAGGTGGA
12901 ACTTCCTCCC GTTGCGGGGT GGAGTGAGGT TAGTTCTGTG TGTCTGGTGG GTGGAGTCAG
12961 GCTTCTCTTG CTACCTGTGA GCATCCTTCC CAGCAGACAT CCTCATCGGG CTTTGTCCCT
13021 CCCCGCTTC CTCCCTCTGC GGGGAGGACC CGGGACCACA GCTGCTGGCC AGGGTAGACT
13081 TGGAGCTGTC CTCCAGAGGG GTCACGTGTA GGAGTGAGAA GAAGGAAGAT CTTGAGAGCT
13141 GCTGAGGGAC CTTGGAGAGC TCAGGATGGC TCAGACGAGG ACACTCGCTT GCCGGGCCTG
13201 GCCCTCCTGG GAAGGAGGGA GCTGCTCAGA ATGCCGCATG ACAACTGAAG GCAACCTGGA
13261 AGGTTCAGGG CCCGCTCTTC CCCCATGTGC CTGTCACGCT CTGGTGCAGT CAAAGGAACG
13321 CCTTCCCCTC AGTTGTTTCT AAGAGCAGAG TCTCCCGCTG CAATCTGGGT GGTAACTGCC
13381 AGCCTTGGAG GATCGTGGCC AACGTGGACC TGCCTACGGA GGGTGGGCTC TGACCCAAGT
13441 GGGGCCTCCT TGCCCAGGTC TCACTGCTTT GCACCGTGGT CAGAGGGACT GTCAGCTGAG
13501 CTTGAGCTCC CCTGGAGCCA GCAGGGCTGT GATGGGCGAG TCCCGGAGCC CCACCCAGAC
13561 CTGAATGCTT CTGAGAGCAA AGGGAAGGAC TGACGAGAGA TGTATATTTA ATTTTTAAC
13621 TGCTGCAAAC ATTGTACATC CAAATTAAAG GAAAAAAATG GAAACCATCA AT
```

```
   1 matleklmka feslksfqqq qqqqqqqqq qqqqqqqqq pppppppppp pqlpqpppqa
  61 qplpqpqpp ppppppppgp avaeeeplhrp kkelsatkkd rvnhcltice nivaqsvrns
 121 pefqkllgia melfllcsdd aesdvrmvad eclnkvikal mdsnlprlql elykeikkng
 181 aprslraalw rfaelahlvr pqkcrpylvn llpcltrtsk rpeesvqetl aaavpkimas
 241 fgnfandnei kvllkafian lksssptirr taagsavsic qhsrrtqyfy swlnvllgl
 301 lvpvedehst llilgvlltl rylvpllgqq vkdtslkgsf gvtrkemevs psaeqlvqvy
 361 eltlhhtqhg dhnvvtgale llqqlfrtpp pellqtltav ggigqltaak eesggrsrsg
 421 siveliaggg sscspvlsrk qkgkvllgee ealeddsesr sdvsssalta svkdeisgel
 481 aassgvstpg saghdiiteg prsqhtlqad svdlascdlt ssatgdeed ilshsssqvs
 541 avpsdpamdl ndgtqasspi sdssqttteg pdsavtpsds seivldgtdn qylglqigqp
 601 qdedeeatgi lpdeaseafr nssmalqqah llknmshcrq psdssvdkfv lrdeatepgd
 661 qenkpcrikg digqstddds aplvhcvrll sasflltggk nvlvpdrdvr vsvkalalsc
 721 vgaavalhpe sffsklykvp ldtteypeeq yvsdilnyid hgdpqvrgat ailcgtlics
 781 ilsrsrfhvg dwmgtirtlt gntfsladci pllrktlkde ssvtcklact avrncvmslc
 841 sssyselglq liidvltlrn ssywlvrtel letlaeidfr lvsfleakae nlhrgahhyt
 901 glikqervl nnvvihllgd edprvrhvaa aslirlvpkl fykcdggqad pvvavardqs
 961 svylkllmhe tqppshfsvs titriyrgyn llpsitdvtm ennlsrviaa vshelitstt
1021 raltfgccea lcllstafpv ciwslgwhcg vpplsasdes rksctvgmat miltlssaw
1081 fpldlsahqd alilagnlla asapkslrss waseeeanpa atkqeevwpa lgdralvpmv
1141 eqlfshllkv inicahvldd vapgpaikaa lpsltnppsl spirrkgkek epgeqasvpl
1201 spkkgseasa asrqsdtsgp vttsksslg sfyhipsylk lhdvlkatha nykvtldlqn
1261 stekfggflr saldvlsqil elatlqdigk cveeilgylk scfsrepmma tvcvqqllkt
1321 lfgtnlasgf dglssnpsks ggraqrlgss svrpglyhyc fmapythftq aladaslrnm
1381 vgaeqendts gwfdvlqkvs tqlktnltsv tknradknai hnhirlfepl vikalkqytt
1441 ttcvqlqkqv ldllaqlvql rvnyclldsd qvfigfvlkq feyievgqfr eseaiipnif
1501 fflvllsyer yhskqiigip kiiqlcdgim asgrkavtha ipalqpivhd lfvlrgtnka
1561 dagkeletqk evvvsmllrl iqyhqvlemf ilvlqqchke nedkwkrlsr qiadiilpml
1621 akqqmhidsh ealgvlntlf eilapsslrp vdmllrsmfv tpntmasvst vqlwisgila
1681 ilrvlisqst edivlsriqe lsfspylisc tvinrlrdgd ststleehse gkqiknlpee
```

```
1741  tfsrfllqlv  gilledivtk  qlkvemseqq  htfycqelgt  llmclihifk  sgmfrritaa
1801  atrlfrsdgc  ggsfytldsl  nlrarsmitt  hpalvllwcq  illlvnhtdy  rwwaevqqtp
1861  krhslsstkl  lspqmsgeee  dsdlaaklgm  cnreivrrga  lilfcdyvcq  nlhdsehltw
1921  livnhiqdli  sisheppvqd  fisavhrnsa  asglfiqaiq  srcenlstpt  mlkktlqcle
1981  gihlsqsgav  ltlyvdrllc  tpfrvlarmv  dilacrrvem  llaanlqssm  aqlpmeelnr
2041  iqeylqssgl  aqrhqrlysl  ldrfrlstmq  dslspsppvs  shpldgdghv  sletvspdkd
2101  wyvhlvksqc  wtrsdsalle  gaelvnripa  edmnafmmns  efnlsllapc  lslgmseisg
2161  gqksalfeaa  revtlarvsg  tvqqlpavhh  vfqpelpaep  aaywsklndl  fgdaalyqsl
2221  ptlaralaqy  lvvvsklpsh  lhlppekekd  ivkfvvatle  alswhliheq  iplsldlqag
2281  ldccclalql  pglwsvvsst  efvthacsli  ycvhfileav  avqpgeqlls  perrtntpka
2341  iseeeeevdp  ntqnpkyita  acemvaemve  slqsvlalgh  krnsgvpafl  tpllrniiis
2401  larlplvnsy  trvpplvwkl  gwspkpggdf  gtafpeipve  flqekevfke  fiyrintlgw
2461  tsrtqfeetw  atllgvlvtq  plvmeqeesp  peedtertgi  nvlavqaits  lvlsamtvpv
2521  agnpavscle  qqprnkplka  ldtrfgrkls  iirgiveqei  qamvskreni  athhlyqawd
2581  pvpslspatt  galishekll  lqinperelg  smsyklgqvs  ihsvwlgnsi  tplreeewde
2641  eeeeeadapa  psspptspvn  srkhragvdi  hscsqfllel  ysrwilpsss  arrtpailis
2701  evvrsllvvs  difterngfe  lmyvtltelr  rvhpsedeil  aqylvpatck  aaavlgmdka
2761  vaepvsrlle  stlrsshlps  rvgalhgvly  vlecdllddt  akqlipvisd  yllsnlkgia
2821  hcvnihsqqh  vlvmcatafy  lienypldvg  pefsasiiqm  cgvmlsgsee  stpsiiyhca
2881  lrglerllls  eqlsrldaes  lvklsvdrvn  vhsphramaa  lglmltcmyt  gkekvspgrt
2941  sdpnpaapds  esvivamerv  svlfdrirkg  fpcearvvar  ilpqflddff  ppqdimnkvi
3001  geflsnqqpy  pqfmatvvyk  vfqtlhstgq  ssmvrdwvml  slsnftqrap  vamatwslsc
3061  ffvsastspw  vaailphvis  rmgkleqvdv  nlfclvatdf  yrhqieeeld  rrafqsvlev
3121  vaapgspyhr  lltclrnvhk  vttc
```

FIG. 3 htt sense target:     5´-..ugcagcugaucaucgaugugcugacccugaggaacaguuc..-3´ htt anti-sense target: 3´-..acgucgacuaguagcuacacgacugggacuccuugucaag..-5´

FIG. 4

SEQ ID NO:20

SEQ ID NO:21 $\Delta G = -10.5$

SEQ ID NO:22

SEQ ID NO:23 $\Delta G = -10.5$

FIG. 5A
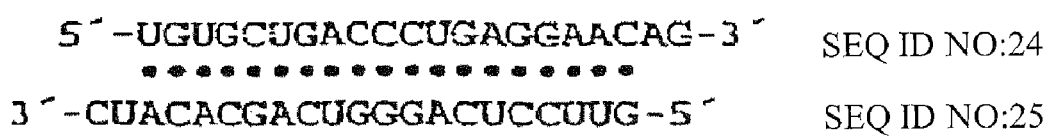
5´-UGUGCUGACCCUGAGGAACAG-3´  SEQ ID NO:24
3´-CUACACGACUGGGACUCCUUG-5´  SEQ ID NO:25
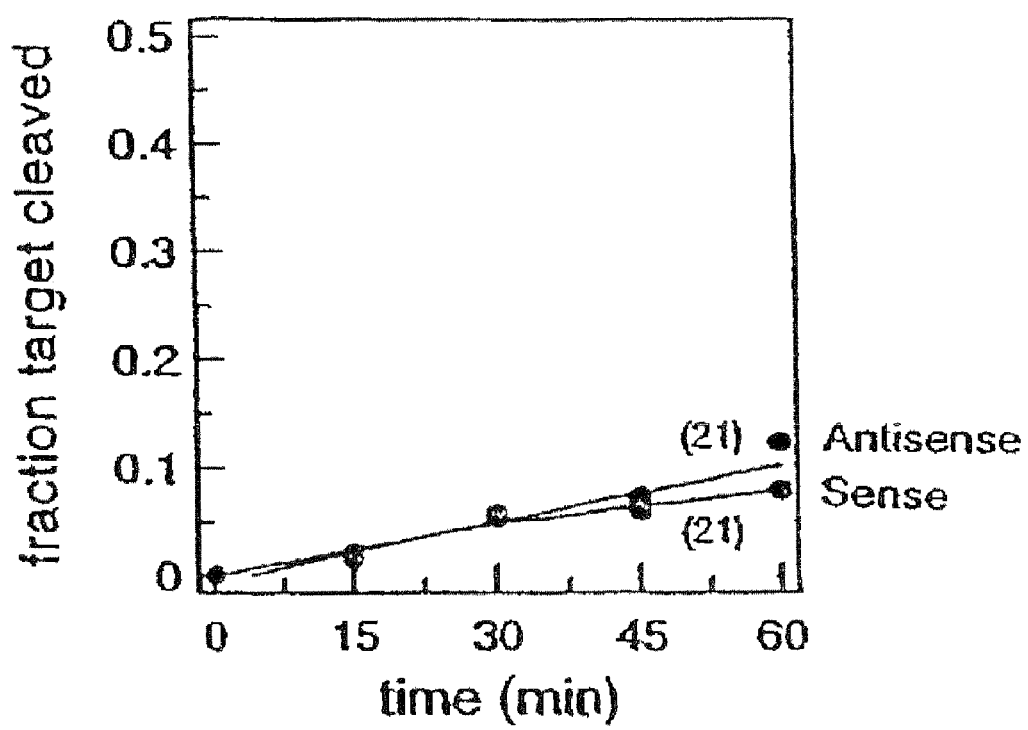

FIG. 5B
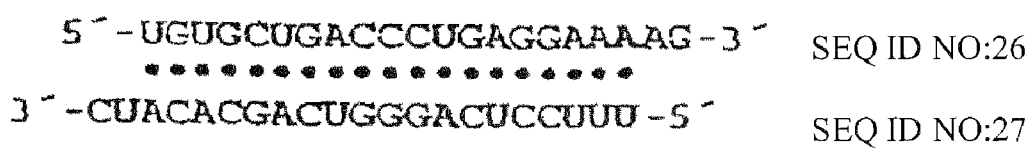
5'-UGUGCUGACCCUGAGGAAAAG-3'  SEQ ID NO:26
3'-CUACACGACUGGGACUCCUUU-5'  SEQ ID NO:27
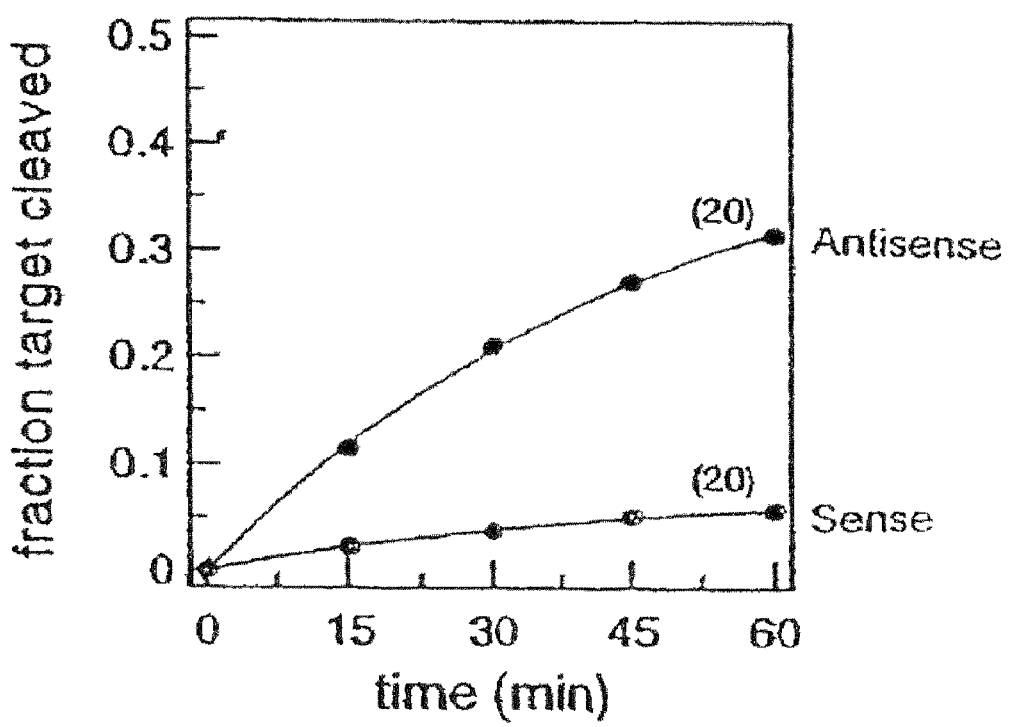

FIG. 6
A
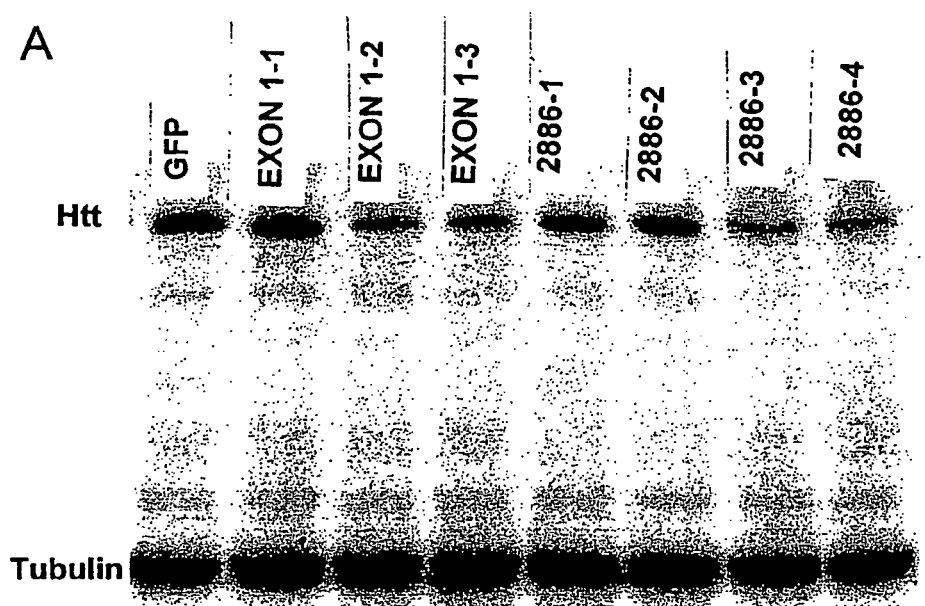
B
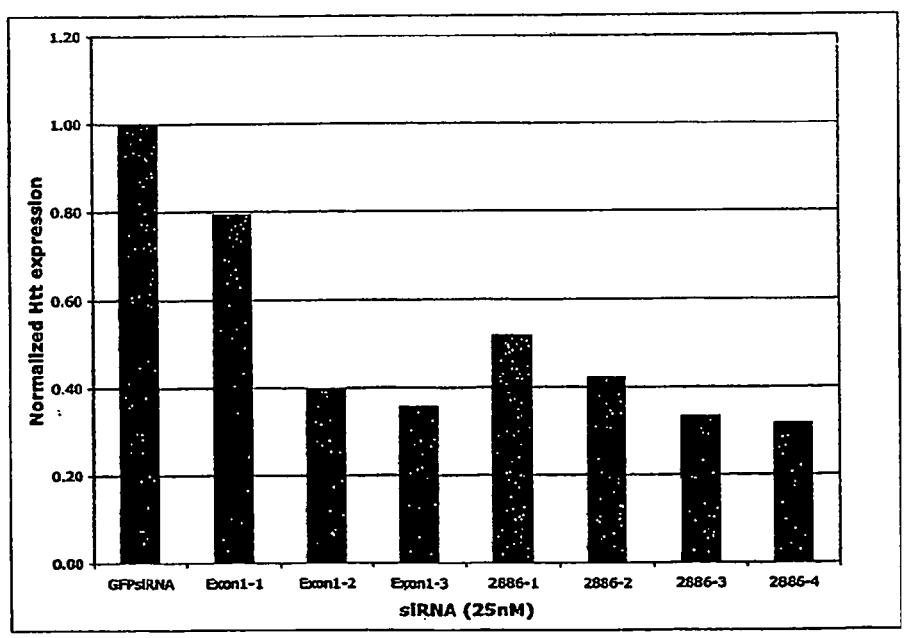

```
                          SEQUENCE LISTING

<160> NUMBER OF SEQ ID NOS: 33

<210> SEQ ID NO 1
<211> LENGTH: 13672
<212> TYPE: DNA
<213> ORGANISM: Homo sapiens

<400> SEQUENCE: 1
ttgctgtgtg aggcagaacc tgcgggggca ggggcgggct ggttccctgg ccagccattg    60
gcagagtccg caggctaggg ctgtcaatca tgctggccgg cgtggccccg cctccgccgg   120
cgcggccccg cctccgccgg cgcacgtctg ggacgcaagg cgccgtgggg gctgccggga   180
cgggtccaag atggacggcc gctcaggttc tgcttttacc tgcggcccag agccccattc   240
attgccccgg tgctgagcgg cgccgcgagt cggcccgagg cctccgggga ctgccgtgcc   300
gggcgggaga ccgccatggc gaccctggaa aagctgatga aggccttcga gtccctcaag   360
tccttccagc agcagcagca gcagcagcag cagcagcagc agcagcagca gcagcagcag   420
cagcagcagc aacagccgcc accgccgccg ccgccgccgc cgcctcctca gcttcctcag   480
ccgccgccgc aggcacagcc gctgctgcct cagccgcagc cgccccgcc gccgccccg   540 ccgccacccg gcccggctgt ggctgaggag ccgctgcacc gaccaaagaa agaactttca   600
gctaccaaga aagaccgtgt gaatcattgt ctgacaatat gtgaaaacat agtggcacag   660
tctgtcagaa attctccaga atttcagaaa cttctgggca tcgctatgga actttttctg   720
ctgtgcagtg atgacgcaga gtcagatgtc aggatggtgg ctgacgaatg cctcaacaaa   780
gttatcaaag ctttgatgga ttctaatctt ccaaggttac agctcgagct ctataaggaa   840
attaaaaaga atggtgcccc tcggagtttg cgtgctgccc tgtggaggtt tgctgagctg   900
gctcacctgg ttcggcctca gaaatgcagg ccttacctgg tgaaccttct gccgtgcctg   960
actcgaacaa gcaagagacc cgaagaatca gtccaggaga ccttggctgc agctgttccc  1020
aaaattatgg cttcttttgg caattttgca aatgacaatg aaattaaggt tttgttaaag  1080
gccttcatag cgaacctgaa gtcaagctcc cccaccattc ggcggacagc ggctggatca  1140
gcagtgagca tctgccagca ctcaagaagg acacaatatt tctatagttg gctactaaat  1200
gtgctcttag gcttactcgt tcctgtcgag gatgaacact ccactctgct gattcttggc  1260
gtgctgctca ccctgaggta tttggtgccc ttgctgcagc agcaggtcaa ggacacaagc  1320
ctgaaaggca gcttcggagt gacaaggaaa gaaatggaag tctctccttc tgcagagcag  1380
cttgtccagg tttatgaact gacgttacat catacacagc accaagacca caatgttgtg  1440
accggagccc tggagctgtt gcagcagctc ttcagaacgc ctccacccga gcttctgcaa  1500
accctgaccg cagtcggggg cattgggcag ctcaccgctg ctaaggagga gtctggtggc  1560
cgaagccgta gtgggagtat tgtggaactt atagctggag ggggttcctc atgcagccct  1620
```

```
gtcctttcaa gaaaacaaaa aggcaaagtg ctcttaggag aagaagaagc cttggaggat    1680
gactctgaat cgagatcgga tgtcagcagc tctgccttaa cagcctcagt gaaggatgag    1740
atcagtggag agctggctgc ttcttcaggg gtttccactc cagggtcagc aggtcatgac    1800
atcatcacag aacagccacg gtcacagcac acactgcagg cggactcagt ggatctggcc    1860
agctgtgact tgacaagctc tgccactgat ggggatgagg aggatatctt gagccacagc    1920
tccagccagg tcagcgccgt cccatctgac cctgccatgg acctgaatga tgggacccag    1980
gcctcgtcgc ccatcagcga cagctcccag accaccaccg aagggcctga ttcagctgtt    2040
accccttcag acagttctga aattgtgtta gacggtaccg acaaccagta tttgggcctg    2100
cagattggac agccccagga tgaagatgag gaagccacag gtattcttcc tgatgaagcc    2160
tcggaggcct tcaggaactc ttccatggcc cttaacagg cacatttatt gaaaaacatg     2220
agtcactgca ggcagccttc tgacagcagt gttgataaat ttgtgttgag agatgaagct    2280
actgaaccgg gtgatcaaga aaacaagcct tgccgcatca aggtgacat tggacagtcc     2340
actgatgatg actctgcacc tcttgtccat tgtgtccgcc ttttatctgc ttcgttttg     2400
ctaacagggg gaaaaaatgt gctggttccg gacaggatg tgagggtcag cgtgaaggcc     2460
ctggccctca gctgtgtggg agcagctgtg gccctccacc cggaatcttt cttcagcaaa    2520
ctctataaag ttcctcttga caccacggaa taccctgagg aacagtatgt ctcagacatc    2580
ttgaactaca tcgatcatgg agacccacag gttcgaggag ccactgccat tctctgtggg    2640
accctcatct gctccatcct cagcaggtcc cgcttccacg tgggagattg gatgggcacc    2700
attagaaccc tcacaggaaa tacatttct ttggcggatt gcattccttt gctgcggaaa     2760
acactgaagg atgagtcttc tgttacttgc aagttagctt gtacagctgt gaggaactgt    2820
gtcatgagtc tctgcagcag cagctacagt gagttaggac tgcagctgat catcgatgtg    2880
ctgactctga ggaacagttc ctattggctg gtgaggacag agcttctgga aacccttgca    2940
gagattgact tcaggctggt gagcttttg gaggcaaaag cagaaaactt acacagaggg     3000
gctcatcatt atacagggct tttaaaactg caagaacgag tgctcaataa tgttgtcatc    3060
catttgcttg gagatgaaga ccccagggtg cgacatgttg ccgcagcatc actaattagg    3120
cttgtcccaa agctgtttta taaatgtgac caaggacaag ctgatccagt agtggccgtg    3180
gcaagagatc aaagcagtgt ttacctgaaa cttctcatgc atgagacgca gcctccatct    3240
catttctccg tcagcacaat aaccagaata tatagaggct ataacctact accaagcata    3300
acagacgtca ctatggaaaa taaccttcca agagttattg cagcagtttc tcatgaacta    3360
atcacatcaa ccaccagagc actcacattt ggatgctgtg aagctttgtg tcttctttcc    3420
actgccttcc cagttgcat ttggagttta ggttggcact gtggagtgcc tccactgagt     3480
gcctcagatg agtctaggaa gagctgtacc gttgggatgg ccacaatgat tctgaccctg    3540
ctctcgtcag cttggttccc attggatctc tcagcccatc aagatgcttt gattttggcc    3600
ggaaacttgc ttgcagccag tgctcccaaa tctctgagaa gttcatgggc tctctgaagaa   3660
gaagccaacc cagcagccac caagcaagag gaggtctggc cagccctggg ggaccgggcc    3720
ctggtgccca tggtggagca gctcttctct cacctgctga aggtgattaa catttgtgcc    3780
cacgtcctgg atgacgtggc tcctggaccc gcaataaagg cagccttgcc ttctctaaca    3840
aacccccctt ctctaagtcc catccgacga aggggaagg agaaagaacc aggagaacaa     3900
gcatctgtac cgttgagtcc caagaaaggc agtgaggcca gtgcagcttc tagacaatct    3960
gataccctcag gtcctgttac aacaagtaaa tcctcatcac tggggagttt ctatcatctt    4020
```

```
ccttcatacc tcaaactgca tgatgtcctg aaagctacac acgctaacta caaggtcacg   4080
ctggatcttc agaacagcac ggaaaagttt ggagggtttc tccgctcagc cttggatgtt   4140 cttttctcaga tactagagct ggccacactg caggacattg ggaagtgtgt tgaagagatc   4200
ctaggatacc tgaaatcctg ctttagtcga gaaccaatga tggcaactgt ttgtgttcaa   4260
caattgttga agactctctt tggcacaaac ttggcctccc agtttgatgg cttatcttcc   4320
aaccccagca agtcacaagg ccgagcacag cgccttggct cctccagtgt gaggccaggc   4380
ttgtaccact actgcttcat ggccccgtac acccacttca cccaggccct cgctgacgcc   4440
agcctgagga acatggtgca ggcggagcag gagaacgaca cctcgggatg gtttgatgtc   4500
ctccagaaag tgtctaccca gttgaagaca aacctcacga gtgtcacaaa gaaccgtgca   4560
gataagaatg ctattcataa tcacattcgt ttgtttgaac ctcttgttat aaaagcttta   4620
aaacagtaca cgactacaac atgtgtgcag ttacagaagc aggttttaga tttgctggcg   4680
cagctggttc agttacgggt taattactgt cttctggatt cagatcaggt gtttattggc   4740
tttgtattga aacagtttga atacattgaa gtgggccagt tcagggaatc agaggcaatc   4800
attccaaaca tctttttctt cttggtatta ctatcttatg aacgctatca ttcaaaacag   4860
atcattggaa ttcctaaaat cattcagctc tgtgatggca tcatggccag tggaaggaag   4920 gctgtgcacac atgccatacc ggctctgcag cccatagtcc acgacctctt tgtattaaga   4980
ggaacaaata aagctgatgc aggaaaagag cttgaaaccc aaaaagaggt ggtggtgtca   5040
atgttactga gactcatcca gtaccatcag gtgttggaga tgttcattct tgtcctgcag   5100
cagtgccaca aggagaatga agacaagtgg aagcgactgt ctcgacagat agctgacatc   5160
atcctcccaa tgttagccaa acagcagatg cacattgact ctcatgaagc ccttggagtg   5220
ttaaatacat tatttgagat tttggcccct tcctccctcc gtccggtaga catgctttta   5280
cggagtatgt tcgtcactcc aaacacaatg gcgtccgtga gcactgttca actgtggata   5340
tcgggaattc tggccatttt gagggttctg atttcccagt caactgaaga tattgttctt   5400
tctcgtattc aggagctctc cttctctccg tatttaatct cctgtacagt aattaatagg   5460
ttaagagatg gggacagtac ttcaacgcta gaagaacaca gtgaagggaa acaaataaag   5520
aatttgccag aagaaacatt ttcaaggttt ctattacaac tggttggtat tcttttagaa   5580
gacattgtta caaacagct gaaggtggaa atgagtgagc agcaacatac tttctattgc   5640
caggaactag gcacactgct aatgtgtctg atccacatct tcaagtctgg aatgttccgg   5700
agaatcacag cagctgccac taggctgttc cgcagtgatg gctgtggcgg cagtttctac   5760
accctggaca gcttgaactt gcgggctcgt tccatgatca ccacccaccc ggccctggtg   5820
ctgctctggt gtcagatact gctgcttgtc aaccacaccg actaccgctg gtgggcagaa   5880
gtgcagcaga ccccgaaaag acacagtctg tccagcacaa agttacttag tcccagatg   5940 tctggagaag aggaggattc tgacttggca gccaaacttg gaatgtgcaa tagagaaata   6000
gtacgaagag gggctctcat tctcttctgt gattatgtct gtcagaacct ccatgactcc   6060
gagcacttaa cgtggctcat tgtaaatcac attcaagatc tgatcagcct ttcccacgag   6120
cctccagtac aggacttcat cagtgccgtt catcggaact ctgctgccag cggcctgttc   6180
atccaggcaa ttcagtctcg ttgtgaaaac cttttcaactc caaccatgct gaagaaaact   6240
cttcagtgct tggaggggat ccatctcagc cagtcgggag ctgtgctcac gctgtatgtg   6300
gacaggcttt gtgcaccccc tttccgtgtg ctggctcgca tggtcgacat ccttgcttgt   6360
cgccgggtag aaatgcttct ggctgcaaat ttacagagca gcatggccca gttgccaatg   6420
```

```
gaagaactca acagaatcca ggaatacctt cagagcagcg ggctcgctca gagacaccaa    6480
aggctctatt ccctgctgga caggtttcgt ctctccacca tgcaagactc acttagtccc    6540
tctcctccag tctcttccca cccgctggac ggggatgggc acgtgtcact ggaaacagtg    6600
agtccggaca aagactggta cgttcatctt gtcaaatccc agtgttggac caggtcagat    6660
tctgcactgc tggaaggtgc agagctggtg aatcggattc ctgctgaaga tatgaatgcc    6720
ttcatgatga actcggagtt caacctaagc ctgctagctc catgcttaag cctagggatg    6780
agtgaaattt ctggtggcca gaagagtgcc ctttttgaag cagcccgtga ggtgactctg    6840
gcccgtgtga gcggcaccgt gcagcagctc cctgctgtcc atcatgtctt ccagcccgag    6900
ctgcctgcag agccggcggc ctactggagc aagttgaatg atctgtttgg ggatgctgca    6960
ctgtatcagt ccctgcccac tctggcccgg ccctggcac agtacctggt ggtggtctcc     7020
aaactgccca gtcatttgca ccttcctcct gagaaagaga aggacattgt gaaattcgtg    7080
gtggcaaccc ttgaggccct gtcctggcat ttgatccatg agcagatccc gctgagtctg    7140
gatctccagg cagggctgga ctgctgctgc ctggccctgc agctgcctgg cctctggagc    7200
gtggtctcct ccacagagtt tgtgacccac gcctgctccc tcatctactg tgtgcacttc    7260
atcctggagg ccgttgcagt gcagcctgga gagcagcttc ttagtccaga aagaaggaca    7320
aatacccccaa aagccatcag cgaggaggag gaggaagtag atccaaacac acagaatcct    7380
aagtatatca ctgcagcctg tgagatggtg gcagaaatgg tggagtctct gcagtcggtg    7440
ttggcccttgg gtcataaaag gaatagcggc gtgccggcgt ttctcacgcc attgctcagg    7500
aacatcatca tcagcctggc ccgcctgccc cttgtcaaca gctacacacg tgtgccccca    7560
ctggtgtgga agcttggatg gtcacccaaa ccggggaggg attttggcac agcattccct    7620
gagatccccg tggagttcct ccaggaaaag gaagtctta aggagttcat ctaccgcatc      7680
aacacactag gctggaccag tcgtactcag tttgaagaaa cttgggccac cctccttggt    7740
gtcctggtga cgcagcccct cgtgatggag caggaggaga gcccaccaga agaagacaca    7800
gagaggaccc agatcaacgt cctggccgtg caggccatca cctcactggt gctcagtgca    7860
atgactgtgc ctgtggccgg caacccagct gtaagctgct tggagcagca gccccggaac    7920
aagcctctga aagctctcga caccaggttt ggggaggaagc tgagcattat cagagggatt    7980
gtggagcaag agattcaagc aatggtttca aagagagaga atattgccac ccatcattta    8040
tatcaggcat gggatcctgt cccttctctg tctccggcta ctacaggtgc cctcatcagc    8100
cacgagaagc tgctgctaca gatcaaccc gagcgggagc tggggagcat gagctacaaa     8160
ctcggccagg tgtccataca ctccgtgtgg ctggggaaca gcatcacacc cctgagggag    8220
gaggaatggg acgaggaaga ggaggaggag gccgacgccc ctgcaccttc gtcaccaccc    8280
acgtctccag tcaactccag gaaacaccgg gctggagttg acatccactc ctgttcgcag    8340
tttttgcttg agttgtacag ccgctggatc ctgccgtcca gctcagccag gaggacccg     8400
gccatcctga tcagtgaggt ggtcagatcc cttctagtgg tctcagactt gttcaccgag    8460
cgcaaccagt ttgagctgat gtatgtgacg ctgacagaac tgcgaagggt gcacccttca    8520
gaagacgaga tcctcgctca gtacctggtg cctgccacct gcaaggcagc tgccgtcctt    8580
gggatggaca aggccgtggc ggagcctgtc agccgcctgc tggagagcac gctcaggagc    8640
agccacctgc ccagcagggt tggagccctg cacggcgtcc tctatgtgct ggagtgcgac    8700
ctgctgacg acactgccaa gcagctcatc ccggtcatca gcgactatct cctctccaac     8760
ctgaaaggga tcgcccactg cgtgaacatt cacagccagc agcacgtact ggtcatgtgt    8820
```

```
gccactgcgt tttacctcat tgagaactat cctctggacg tagggccgga attttcagca    8880
tcaataatac agatgtgtgg ggtgatgctg tctggaagtg aggagtccac cccctccatc    8940
atttaccact gtgccctcag aggcctggag cgcctcctgc tctctgagca gctctcccgc    9000
ctggatgcag aatcgctggt caagctgagt gtggacagag tgaacgtgca cagcccgcac    9060
cgggccatgg cggctctggg cctgatgctc acctgcatgt acacaggaaa ggagaaagtc    9120
agtccgggta gaacttcaga ccctaatcct gcagccccg acagcgagtc agtgattgtt    9180
gctatggagc gggtatctgt tcttttgat aggatcagga aaggctttcc ttgtgaagcc    9240
agagtggtgg ccaggatcct gccccagttt ctagacgact tcttcccacc ccaggacatc    9300
atgaacaaag tcatcggaga gtttctgtcc aaccagcagc catacccca gttcatggcc    9360
accgtggtgt ataaggtgtt tcagactctg cacagcaccg ggcagtcgtc catggtccgg    9420
gactgggtca tgctgtccct ctccaacttc acgcagaggg ccccggtcgc catggccacg    9480
tggagcctct cctgcttctt tgtcagcgcg tccaccagcc cgtgggtcgc ggcgatcctc    9540
ccacatgtca tcagcaggat gggcaagctg gagcaggtgg acgtgaacct tttctgcctg    9600
gtcgccacag acttctacag acaccagata gaggaggagc tcgaccgcag ggccttccag    9660
tctgtgcttg aggtggttgc agccccagga agcccatatc accggctgct gacttgttta    9720
cgaaatgtcc acaaggtcac cacctgctga gcgccatggt gggagagact gtgaggcggc    9780
agctggggcc ggagcctttg gaagtctgtg cccttgtgcc ctgcctccac cgagccagct    9840
tggtccctat gggcttccgc acatgccgcg ggcggccagg caacgtgcgt gtctctgcca    9900
tgtggcagaa gtgctctttg tggcagtggc caggcaggga gtgtctgcag tcctggtggg    9960
gctgagcctg aggccttcca gaaagcagga gcagctgtgc tgcacccat gtgggtgacc   10020
aggtccttc tcctgatagt cacctgctgg ttgttgccag gttgcagctg ctcttgcatc   10080
tgggccagaa gtcctccctc ctgcaggctg gctgttggcc cctctgctgt cctgcagtag   10140
aaggtgccgt gagcaggctt tgggaacact ggcctgggtc tccctggtgg ggtgtgcatg   10200
ccacgccccg tgtctggatg cacagatgcc atggcctgtg ctgggccagt ggctgggggt   10260
gctagacacc cggcaccatt ctcccttctc tcttttcttc tcaggattta aaatttaatt   10320
atatcagtaa agagattaat tttaacgaac tctttctatg cccgtgtaaa gtatgtgaat   10380
cgcaaggcct gtgctgcatg cgacagcgtc cggggtggtg gacagggccc ccggccacgc   10440
tccctctcct gtagccactg gcatagccct cctgagcacc cgctgacatt tccgttgtac   10500
atgttcctgt ttatgcattc acaaggtgac tgggatgtag agaggcgtta gtgggcaggt   10560
ggccacagca ggactgagga caggccccca ttatcctagg ggtgcgctca actgcagccc   10620
ctcctcctcg ggcacagacg actgtcgttc tccacccacc agtcagggac agcagcctcc   10680
ctgtcactca gctgagaagg ccagcccctcc ctggctgtga gcagcctcca ctgtgtccag   10740
agacatgggc ctcccactcc tgttccttgc tagccctggg gtggcgtctg cctaggagct   10800
ggctggcagg tgttgggacc tgctgctcca tggatgcatg ccctaagagt gtcactgagc   10860
tgtgttttgt ctgagcctct ctcggtcaac agcaaagctt ggtgtcttgg cactgttagt   10920
gacagagccc agcatccctt ctgccccgt tccagctgac atcttgcacg gtgacccctt   10980
ttagtcagga gagtgcagat ctgtgctcat cggagactgc cccacggccc tgtcagagcc   11040
gccactccta tccccaggac aggtccctgg accagcctcc tgtttgcagg cccagaggag   11100
ccaagtcatt aaaaatggaag tggattctgg atggccgggc tgctgctgat gtaggagctg   11160
gatttgggag ctctgcttgc cgactggctg tgagacgagg caggggctct gcttcctcag   11220
```

```
ccctagaggc gagccaggca aggttggcga ctgtcatgtg gcttggtttg gtcatgcccg   11280
tcgatgtttt gggtattgaa tgtggtaagt ggaggaaatg ttggaactct gtgcaggtgc   11340
tgccttgaga cccccaagct tccacctgtc cctctcctat gtggcagctg gggagcagct   11400
gagatgtgga cttgtatgct gcccacatac gtgagggga gctgaaaggg agccctgct   11460 caaagggagc ccctcctctg agcagcctct gccaggcctg tatgaggctt ttcccaccag   11520
ctcccaacag aggcctcccc cagccaggac cacctcgtcc tcgtggcggg gcagcaggag   11580
cggtagaaag gggtccgatg tttgaggagg cccttaaggg aagctactga attataacac   11640
gtaagaaaat caccattctt ccgtattggt tgggggctcc tgtttctcat cctagctttt   11700
tcctggaaaa gcccgctaga aggtttggga acgaggggaa agttctcaga actgttgctg   11760
ctccccaccc gcctcccgcc tccccgcag gttatgtcag cagctctgag acagcagtat   11820
cacaggccag atgttgttcc tggctagatg tttacatttg taagaaataa cactgtgaat   11880
gtaaaacaga gccattccct tggaatgcat atcgctgggc tcaacataga gtttgtcttc   11940
ctcttgttta cgacgtgatc taaaccagtc cttagcaagg ggctcagaac accccgctct   12000
ggcagtaggt gtcccccacc cccaaagacc tgcctgtgtg ctccggagat gaatatgagc   12060
tcattagtaa aaatgacttc acccacgcat atacataaag tatccatgca tgtgcatata   12120
gacacatcta taattttaca cacacacctc tcaagacgga gatgcatggc ctctaagagt   12180
gcccgtgtcg gttcttcctg gaagttgact ttccttagac ccgccaggtc aagttagccg   12240
cgtgacggac atccaggcgt gggacgtggt cagggcaggg ctcattcatt gcccactagg   12300
atcccactgg cgaagatggt ctccatatca gctctctgca aagggagga agactttatc   12360 atgttcctaa aaatctgtgg caagcaccca tcgtattatc caaattttgt tgcaaatgtg   12420
attaatttgg ttgtcaagtt ttgggggtgg gctgtgggga gattgctttt gttttcctgc   12480
tggtaatatc gggaaagatt ttaatgaaac cagggtagaa ttgtttggca atgcactgaa   12540
gcgtgtttct ttcccaaaat gtgcctccct tccgctgcgg gcccagctga gtctatgtag   12600
gtgatgtttc cagctgccaa gtgctctttg ttactgtcca ccctcatttc tgccagcgca   12660
tgtgtccttt caaggggaaa atgtgaagct gaaccccctc cagacaccca gaatgtagca   12720
tctgagaagg ccctgtgccc taaaggacac ccctcgcccc catcttcatg gaggggtca   12780 tttcagagcc ctcggagcca atgaacagct cctcctcttg gagctgagat gagccccacg   12840
tggagctcgg gacggatagt agacagcaat aactcggtgt gtggccgcct ggcaggtgga   12900
acttcctccc gttgcggggt ggagtgaggt tagttctgtg tgtctggtgg gtggagtcag   12960
gcttctcttg ctacctgtga gcatccttcc cagcagacat cctcatcggg ctttgtccct   13020
cccccgcttc ctccctctgc ggggaggacc cgggaccaca gctgctggcc agggtagact   13080
tggagctgtc ctccagaggg gtcacgtgta ggagtgagaa gaaggaagat cttgagagct   13140
gctgagggac cttggagagc tcaggatggc tcagacgagg acactcgctt gccgggcctg   13200
gccctcctgg gaaggaggga gctgctcaga atgccgcatg acaactgaag gcaacctgga   13260
aggttcaggg cccgctcttc ccccatgtgc ctgtcacgct ctggtgcagt caaaggaacg   13320
ccttcccctc agttgtttct aagagcagag tctcccgctg caatctgggt ggtaactgcc   13380
agccttggag gatcgtggcc aacgtggacc tgcctacgga gggtgggctc tgacccaagt   13440
ggggcctcct tgcccaggtc tcactgcttt gcaccgtggt cagagggact gtcagctgag   13500
cttgagctcc cctggagcca gcagggctgt gatgggcgag tccggagcc ccacccgac   13560 ctgaatgctt ctgagagcaa agggaaggac tgacgagaga tgtatattta attttttaac   13620
```
tgctgcaaac attgtacatc caaattaaag ggaaaaaatg gaaaccatca at         13672

<210> SEQ ID NO 2
<211> LENGTH: 3144
<212> TYPE: PRT
<213> ORGANISM: Homo sapiens

<400> SEQUENCE: 2

Met Ala Thr Leu Glu Lys Leu Met Lys Ala Phe Glu Ser Leu Lys Ser
 1               5                  10                  15

Phe Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365

```
His Gln Asp His Asn Val Val Thr Gly Ala Leu Glu Leu Leu Gln Gln
        370                 375                 380

Leu Phe Arg Thr Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Ser Ser
                420                 425                 430

Cys Ser Pro Val Leu Ser Arg Lys Gln Lys Gly Lys Val Leu Leu Gly
            435                 440                 445

Glu Glu Glu Ala Leu Glu Asp Asp Ser Glu Ser Arg Ser Asp Val Ser
        450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
                500                 505                 510

Asp Leu Ala Ser Cys Asp Leu Thr Ser Ser Ala Thr Asp Gly Asp Glu
            515                 520                 525

Glu Asp Ile Leu Ser His Ser Ser Ser Gln Val Ser Ala Val Pro Ser
        530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
                580                 585                 590

Leu Gly Leu Gln Ile Gly Gln Pro Gln Asp Glu Asp Glu Glu Ala Thr
            595                 600                 605

Gly Ile Leu Pro Asp Glu Ala Ser Glu Ala Phe Arg Asn Ser Ser Met
        610                 615                 620

Ala Leu Gln Gln Ala His Leu Leu Lys Asn Met Ser His Cys Arg Gln
625                 630                 635                 640

Pro Ser Asp Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
                660                 665                 670

Gly Gln Ser Thr Asp Asp Ser Ala Pro Leu Val His Cys Val Arg
            675                 680                 685

Leu Leu Ser Ala Ser Phe Leu Leu Thr Gly Gly Lys Asn Val Leu Val
        690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
        755                 760                 765

Ala Thr Ala Ile Leu Cys Gly Thr Leu Ile Cys Ser Ile Leu Ser Arg
770                 775                 780

Ser Arg Phe His Val Gly Asp Trp Met Gly Thr Ile Arg Thr Leu Thr
                785                 790                 795                 800
```

-continued

```
Gly Asn Thr Phe Ser Leu Ala Asp Cys Ile Pro Leu Leu Arg Lys Thr
                805                 810                 815
Leu Lys Asp Glu Ser Ser Val Thr Cys Lys Leu Ala Cys Thr Ala Val
            820                 825                 830
Arg Asn Cys Val Met Ser Leu Cys Ser Ser Tyr Ser Glu Leu Gly
        835                 840                 845
Leu Gln Leu Ile Ile Asp Val Leu Thr Leu Arg Asn Ser Ser Tyr Trp
    850                 855                 860
Leu Val Arg Thr Glu Leu Leu Glu Thr Leu Ala Glu Ile Asp Phe Arg
865                 870                 875                 880
Leu Val Ser Phe Leu Glu Ala Lys Ala Glu Asn Leu His Arg Gly Ala
                885                 890                 895
His His Tyr Thr Gly Leu Leu Lys Leu Gln Glu Arg Val Leu Asn Asn
            900                 905                 910
Val Val Ile His Leu Leu Gly Asp Glu Asp Pro Arg Val Arg His Val
        915                 920                 925
Ala Ala Ala Ser Leu Ile Arg Leu Val Pro Lys Leu Phe Tyr Lys Cys
    930                 935                 940
Asp Gln Gly Gln Ala Asp Pro Val Val Ala Val Ala Arg Asp Gln Ser
945                 950                 955                 960
Ser Val Tyr Leu Lys Leu Leu Met His Glu Thr Gln Pro Pro Ser His
                965                 970                 975
Phe Ser Val Ser Thr Ile Thr Arg Ile Tyr Arg Gly Tyr Asn Leu Leu
            980                 985                 990
Pro Ser Ile Thr Asp Val Thr Met Glu Asn Asn Leu Ser Arg Val Ile
        995                 1000                1005
Ala Ala Val Ser His Glu Leu Ile Thr Ser Thr Arg Ala Leu Thr
    1010                1015                1020
Phe Gly Cys Cys Glu Ala Leu Cys Leu Leu Ser Thr Ala Phe Pro Val
1025                1030                1035                1040
Cys Ile Trp Ser Leu Gly Trp His Cys Gly Val Pro Pro Leu Ser Ala
                1045                1050                1055
Ser Asp Glu Ser Arg Lys Ser Cys Thr Val Gly Met Ala Thr Met Ile
            1060                1065                1070
Leu Thr Leu Leu Ser Ser Ala Trp Phe Pro Leu Asp Leu Ser Ala His
        1075                1080                1085
Gln Asp Ala Leu Ile Leu Ala Gly Asn Leu Leu Ala Ala Ser Ala Pro
    1090                1095                1100
Lys Ser Leu Arg Ser Ser Trp Ala Ser Glu Glu Glu Ala Asn Pro Ala
1105                1110                1115                1120
Ala Thr Lys Gln Glu Glu Val Trp Pro Ala Leu Gly Asp Arg Ala Leu
                1125                1130                1135
Val Pro Met Val Glu Gln Leu Phe Ser His Leu Leu Lys Val Ile Asn
            1140                1145                1150
Ile Cys Ala His Val Leu Asp Asp Val Ala Pro Gly Pro Ala Ile Lys
        1155                1160                1165
Ala Ala Leu Pro Ser Leu Thr Asn Pro Pro Ser Leu Ser Pro Ile Arg
    1170                1175                1180
Arg Lys Gly Lys Glu Lys Glu Pro Gly Glu Gln Ala Ser Val Pro Leu
1185                1190                1195                1200
Ser Pro Lys Lys Gly Ser Glu Ala Ser Ala Ala Ser Arg Gln Ser Asp
                1205                1210                1215
Thr Ser Gly Pro Val Thr Thr Ser Lys Ser Ser Ser Leu Gly Ser Phe
```

-continued

```
                1220              1225              1230
Tyr His Leu Pro Ser Tyr Leu Lys Leu His Asp Val Leu Lys Ala Thr
            1235              1240              1245
His Ala Asn Tyr Lys Val Thr Leu Asp Leu Gln Asn Ser Thr Glu Lys
            1250              1255              1260
Phe Gly Gly Phe Leu Arg Ser Ala Leu Asp Val Leu Ser Gln Ile Leu
1265              1270              1275              1280
Glu Leu Ala Thr Leu Gln Asp Ile Gly Lys Cys Val Glu Glu Ile Leu
            1285              1290              1295
Gly Tyr Leu Lys Ser Cys Phe Ser Arg Glu Pro Met Met Ala Thr Val
            1300              1305              1310
Cys Val Gln Gln Leu Leu Lys Thr Leu Phe Gly Thr Asn Leu Ala Ser
            1315              1320              1325
Gln Phe Asp Gly Leu Ser Ser Asn Pro Ser Lys Ser Gln Gly Arg Ala
            1330              1335              1340
Gln Arg Leu Gly Ser Ser Ser Val Arg Pro Gly Leu Tyr His Tyr Cys
1345              1350              1355              1360
Phe Met Ala Pro Tyr Thr His Phe Thr Gln Ala Leu Ala Asp Ala Ser
            1365              1370              1375
Leu Arg Asn Met Val Gln Ala Glu Gln Glu Asn Asp Thr Ser Gly Trp
            1380              1385              1390
Phe Asp Val Leu Gln Lys Val Ser Thr Gln Leu Lys Thr Asn Leu Thr
            1395              1400              1405
Ser Val Thr Lys Asn Arg Ala Asp Lys Asn Ala Ile His Asn His Ile
            1410              1415              1420
Arg Leu Phe Glu Pro Leu Val Ile Lys Ala Leu Lys Gln Tyr Thr Thr
1425              1430              1435              1440
Thr Thr Cys Val Gln Leu Gln Lys Gln Val Leu Asp Leu Leu Ala Gln
            1445              1450              1455
Leu Val Gln Leu Arg Val Asn Tyr Cys Leu Leu Asp Ser Asp Gln Val
            1460              1465              1470
Phe Ile Gly Phe Val Leu Lys Gln Phe Glu Tyr Ile Glu Val Gly Gln
            1475              1480              1485
Phe Arg Glu Ser Glu Ala Ile Ile Pro Asn Ile Phe Phe Phe Leu Val
            1490              1495              1500
Leu Leu Ser Tyr Glu Arg Tyr His Ser Lys Gln Ile Ile Gly Ile Pro
1505              1510              1515              1520
Lys Ile Ile Gln Leu Cys Asp Gly Ile Met Ala Ser Gly Arg Lys Ala
            1525              1530              1535
Val Thr His Ala Ile Pro Ala Leu Gln Pro Ile Val His Asp Leu Phe
            1540              1545              1550
Val Leu Arg Gly Thr Asn Lys Ala Asp Ala Gly Lys Glu Leu Glu Thr
            1555              1560              1565
Gln Lys Glu Val Val Ser Met Leu Leu Arg Leu Ile Gln Tyr His
            1570              1575              1580
Gln Val Leu Glu Met Phe Ile Leu Val Leu Gln Gln Cys His Lys Glu
1585              1590              1595              1600
Asn Glu Asp Lys Trp Lys Arg Leu Ser Arg Gln Ile Ala Asp Ile Ile
            1605              1610              1615
Leu Pro Met Leu Ala Lys Gln Gln Met His Ile Asp Ser His Glu Ala
            1620              1625              1630
Leu Gly Val Leu Asn Thr Leu Phe Glu Ile Leu Ala Pro Ser Ser Leu
            1635              1640              1645
```

-continued

Arg Pro Val Asp Met Leu Leu Arg Ser Met Phe Val Thr Pro Asn Thr
1650                1655                1660

Met Ala Ser Val Ser Thr Val Gln Leu Trp Ile Ser Gly Ile Leu Ala
1665                1670                1675                1680

Ile Leu Arg Val Leu Ile Ser Gln Ser Thr Glu Asp Ile Val Leu Ser
                1685                1690                1695

Arg Ile Gln Glu Leu Ser Phe Ser Pro Tyr Leu Ile Ser Cys Thr Val
                1700                1705                1710

Ile Asn Arg Leu Arg Asp Gly Asp Ser Thr Ser Thr Leu Glu Glu His
                1715                1720                1725

Ser Glu Gly Lys Gln Ile Lys Asn Leu Pro Glu Thr Phe Ser Arg
                1730                1735                1740

Phe Leu Leu Gln Leu Val Gly Ile Leu Leu Glu Asp Ile Val Thr Lys
1745                1750                1755                1760

Gln Leu Lys Val Glu Met Ser Glu Gln His Thr Phe Tyr Cys Gln
                1765                1770                1775

Glu Leu Gly Thr Leu Leu Met Cys Leu Ile His Ile Phe Lys Ser Gly
                1780                1785                1790

Met Phe Arg Arg Ile Thr Ala Ala Ala Thr Arg Leu Phe Arg Ser Asp
                1795                1800                1805

Gly Cys Gly Gly Ser Phe Tyr Thr Leu Asp Ser Leu Asn Leu Arg Ala
                1810                1815                1820

Arg Ser Met Ile Thr Thr His Pro Ala Leu Val Leu Leu Trp Cys Gln
1825                1830                1835                1840

Ile Leu Leu Leu Val Asn His Thr Asp Tyr Arg Trp Trp Ala Glu Val
                1845                1850                1855

Gln Gln Thr Pro Lys Arg His Ser Leu Ser Ser Thr Lys Leu Leu Ser
                1860                1865                1870

Pro Gln Met Ser Gly Glu Glu Asp Ser Asp Leu Ala Ala Lys Leu
                1875                1880                1885

Gly Met Cys Asn Arg Glu Ile Val Arg Arg Gly Ala Leu Ile Leu Phe
                1890                1895                1900

Cys Asp Tyr Val Cys Gln Asn Leu His Asp Ser Glu His Leu Thr Trp
1905                1910                1915                1920

Leu Ile Val Asn His Ile Gln Asp Leu Ile Ser Leu Ser His Glu Pro
                1925                1930                1935

Pro Val Gln Asp Phe Ile Ser Ala Val His Arg Asn Ser Ala Ala Ser
                1940                1945                1950

Gly Leu Phe Ile Gln Ala Ile Gln Ser Arg Cys Glu Asn Leu Ser Thr
                1955                1960                1965

Pro Thr Met Leu Lys Lys Thr Leu Gln Cys Leu Glu Gly Ile His Leu
                1970                1975                1980

Ser Gln Ser Gly Ala Val Leu Thr Leu Tyr Val Asp Arg Leu Leu Cys
1985                1990                1995                2000

Thr Pro Phe Arg Val Leu Ala Arg Met Val Asp Ile Leu Ala Cys Arg
                2005                2010                2015

Arg Val Glu Met Leu Leu Ala Ala Asn Leu Gln Ser Ser Met Ala Gln
                2020                2025                2030

Leu Pro Met Glu Glu Leu Asn Arg Ile Gln Glu Tyr Leu Gln Ser Ser
                2035                2040                2045

Gly Leu Ala Gln Arg His Gln Arg Leu Tyr Ser Leu Leu Asp Arg Phe
                2050                2055                2060

Arg Leu Ser Thr Met Gln Asp Ser Leu Ser Pro Ser Pro Pro Val Ser
2065                2070                2075                2080

Ser His Pro Leu Asp Gly Asp Gly His Val Ser Leu Glu Thr Val Ser
            2085                2090                2095

Pro Asp Lys Asp Trp Tyr Val His Leu Val Lys Ser Gln Cys Trp Thr
        2100                2105                2110

Arg Ser Asp Ser Ala Leu Leu Glu Gly Ala Glu Leu Val Asn Arg Ile
        2115                2120                2125

Pro Ala Glu Asp Met Asn Ala Phe Met Met Asn Ser Glu Phe Asn Leu
        2130                2135                2140

Ser Leu Leu Ala Pro Cys Leu Ser Leu Gly Met Ser Glu Ile Ser Gly
2145                2150                2155                2160

Gly Gln Lys Ser Ala Leu Phe Glu Ala Ala Arg Glu Val Thr Leu Ala
            2165                2170                2175

Arg Val Ser Gly Thr Val Gln Gln Leu Pro Ala Val His His Val Phe
            2180                2185                2190

Gln Pro Glu Leu Pro Ala Glu Pro Ala Ala Tyr Trp Ser Lys Leu Asn
            2195                2200                2205

Asp Leu Phe Gly Asp Ala Ala Leu Tyr Gln Ser Leu Pro Thr Leu Ala
        2210                2215                2220

Arg Ala Leu Ala Gln Tyr Leu Val Val Ser Lys Leu Pro Ser His
2225                2230                2235                2240

Leu His Leu Pro Pro Glu Lys Glu Lys Asp Ile Val Lys Phe Val Val
            2245                2250                2255

Ala Thr Leu Glu Ala Leu Ser Trp His Leu Ile His Glu Gln Ile Pro
            2260                2265                2270

Leu Ser Leu Asp Leu Gln Ala Gly Leu Asp Cys Cys Cys Leu Ala Leu
        2275                2280                2285

Gln Leu Pro Gly Leu Trp Ser Val Val Ser Ser Thr Glu Phe Val Thr
        2290                2295                2300

His Ala Cys Ser Leu Ile Tyr Cys Val His Phe Ile Leu Glu Ala Val
2305                2310                2315                2320

Ala Val Gln Pro Gly Glu Gln Leu Leu Ser Pro Glu Arg Arg Thr Asn
            2325                2330                2335

Thr Pro Lys Ala Ile Ser Glu Glu Glu Glu Val Asp Pro Asn Thr
            2340                2345                2350

Gln Asn Pro Lys Tyr Ile Thr Ala Ala Cys Glu Met Val Ala Glu Met
            2355                2360                2365

Val Glu Ser Leu Gln Ser Val Leu Ala Leu Gly His Lys Arg Asn Ser
        2370                2375                2380

Gly Val Pro Ala Phe Leu Thr Pro Leu Leu Arg Asn Ile Ile Ile Ser
2385                2390                2395                2400

Leu Ala Arg Leu Pro Leu Val Asn Ser Tyr Thr Arg Val Pro Pro Leu
            2405                2410                2415

Val Trp Lys Leu Gly Trp Ser Pro Lys Pro Gly Gly Asp Phe Gly Thr
            2420                2425                2430

Ala Phe Pro Glu Ile Pro Val Glu Phe Leu Gln Glu Lys Glu Val Phe
            2435                2440                2445

Lys Glu Phe Ile Tyr Arg Ile Asn Thr Leu Gly Trp Thr Ser Arg Thr
            2450                2455                2460

Gln Phe Glu Glu Thr Trp Ala Thr Leu Leu Gly Val Leu Val Thr Gln
2465                2470                2475                2480

Pro Leu Val Met Glu Gln Glu Glu Ser Pro Pro Glu Glu Asp Thr Glu
            2485                2490                2495

Arg Thr Gln Ile Asn Val Leu Ala Val Gln Ala Ile Thr Ser Leu Val

-continued

```
                2500                2505                2510
Leu Ser Ala Met Thr Val Pro Val Ala Gly Asn Pro Val Ser Cys
            2515                2520                2525

Leu Glu Gln Gln Pro Arg Asn Lys Pro Leu Lys Ala Leu Asp Thr Arg
            2530                2535            2540

Phe Gly Arg Lys Leu Ser Ile Ile Arg Gly Ile Val Glu Gln Glu Ile
2545                2550                2555                2560

Gln Ala Met Val Ser Lys Arg Glu Asn Ile Ala Thr His His Leu Tyr
            2565                2570                2575

Gln Ala Trp Asp Pro Val Pro Ser Leu Ser Pro Ala Thr Thr Gly Ala
            2580                2585                2590

Leu Ile Ser His Glu Lys Leu Leu Gln Ile Asn Pro Glu Arg Glu
            2595                2600            2605

Leu Gly Ser Met Ser Tyr Lys Leu Gly Gln Val Ser Ile His Ser Val
            2610                2615                2620

Trp Leu Gly Asn Ser Ile Thr Pro Leu Arg Glu Glu Glu Trp Asp Glu
2625                2630                2635                2640

Glu Glu Glu Glu Glu Ala Asp Ala Pro Ala Pro Ser Ser Pro Pro Thr
                2645                2650                2655

Ser Pro Val Asn Ser Arg Lys His Arg Ala Gly Val Asp Ile His Ser
            2660                2665            2670

Cys Ser Gln Phe Leu Leu Glu Leu Tyr Ser Arg Trp Ile Leu Pro Ser
            2675                2680            2685

Ser Ser Ala Arg Arg Thr Pro Ala Ile Leu Ile Ser Glu Val Val Arg
            2690                2695            2700

Ser Leu Leu Val Val Ser Asp Leu Phe Thr Glu Arg Asn Gln Phe Glu
2705                2710                2715                2720

Leu Met Tyr Val Thr Leu Thr Glu Leu Arg Arg Val His Pro Ser Glu
            2725                2730                2735

Asp Glu Ile Leu Ala Gln Tyr Leu Val Pro Ala Thr Cys Lys Ala Ala
            2740                2745                2750

Ala Val Leu Gly Met Asp Lys Ala Val Ala Glu Pro Val Ser Arg Leu
            2755                2760                2765

Leu Glu Ser Thr Leu Arg Ser Ser His Leu Pro Ser Arg Val Gly Ala
            2770                2775            2780

Leu His Gly Val Leu Tyr Val Leu Glu Cys Asp Leu Leu Asp Asp Thr
2785                2790                2795                2800

Ala Lys Gln Leu Ile Pro Val Ile Ser Asp Tyr Leu Leu Ser Asn Leu
            2805                2810                2815

Lys Gly Ile Ala His Cys Val Asn Ile His Ser Gln Gln His Val Leu
            2820                2825                2830

Val Met Cys Ala Thr Ala Phe Tyr Leu Ile Glu Asn Tyr Pro Leu Asp
            2835                2840                2845

Val Gly Pro Glu Phe Ser Ala Ser Ile Ile Gln Met Cys Gly Val Met
            2850                2855                2860

Leu Ser Gly Ser Glu Glu Ser Thr Pro Ser Ile Ile Tyr His Cys Ala
2865                2870                2875                2880

Leu Arg Gly Leu Glu Arg Leu Leu Leu Ser Glu Gln Leu Ser Arg Leu
            2885                2890                2895

Asp Ala Glu Ser Leu Val Lys Leu Ser Val Asp Arg Val Asn Val His
            2900                2905                2910

Ser Pro His Arg Ala Met Ala Ala Leu Gly Leu Met Leu Thr Cys Met
            2915                2920                2925
```

```
Tyr Thr Gly Lys Glu Lys Val Ser Pro Gly Arg Thr Ser Asp Pro Asn
        2930                2935                2940

Pro Ala Ala Pro Asp Ser Glu Ser Val Ile Val Ala Met Glu Arg Val
2945                2950                2955                2960

Ser Val Leu Phe Asp Arg Ile Arg Lys Gly Phe Pro Cys Glu Ala Arg
            2965                2970                2975

Val Val Ala Arg Ile Leu Pro Gln Phe Leu Asp Asp Phe Phe Pro Pro
        2980                2985                2990

Gln Asp Ile Met Asn Lys Val Ile Gly Glu Phe Leu Ser Asn Gln Gln
            2995                3000                3005

Pro Tyr Pro Gln Phe Met Ala Thr Val Val Tyr Lys Val Phe Gln Thr
        3010                3015                3020

Leu His Ser Thr Gly Gln Ser Ser Met Val Arg Asp Trp Val Met Leu
3025                3030                3035                3040

Ser Leu Ser Asn Phe Thr Gln Arg Ala Pro Val Ala Met Ala Thr Trp
            3045                3050                3055

Ser Leu Ser Cys Phe Phe Val Ser Ala Ser Thr Ser Pro Trp Val Ala
            3060                3065                3070

Ala Ile Leu Pro His Val Ile Ser Arg Met Gly Lys Leu Glu Gln Val
        3075                3080                3085

Asp Val Asn Leu Phe Cys Leu Val Ala Thr Asp Phe Tyr Arg His Gln
        3090                3095                3100

Ile Glu Glu Glu Leu Asp Arg Arg Ala Phe Gln Ser Val Leu Glu Val
3105                3110                3115                3120

Val Ala Ala Pro Gly Ser Pro Tyr His Arg Leu Leu Thr Cys Leu Arg
            3125                3130                3135

Asn Val His Lys Val Thr Thr Cys
            3140

<210> SEQ ID NO 3
<211> LENGTH: 40
<212> TYPE: DNA
<213> ORGANISM: Artificial Sequence
<220> FEATURE:
<223> OTHER INFORMATION: synthetic construct

<400> SEQUENCE: 3
ugcagcugau caucgaugug cugacccuga ggaacaguuc                         40

<210> SEQ ID NO 4
<211> LENGTH: 40
<212> TYPE: DNA
<213> ORGANISM: Artificial Sequence
<220> FEATURE:
<223> OTHER INFORMATION: synthetic construct

<400> SEQUENCE: 4
gaacuguucc ucaggucag cacaucgaug aucagcugca                          40

<210> SEQ ID NO 5
<211> LENGTH: 21
<212> TYPE: DNA
<213> ORGANISM: Artificial Sequence
<220> FEATURE:
<223> OTHER INFORMATION: synthetic construct

<400> SEQUENCE: 5
tgtgctgact ctgaggaaca g                                             21

<210> SEQ ID NO 6
```

```
<211> LENGTH: 21
<212> TYPE: DNA
<213> ORGANISM: Artificial Sequence
<220> FEATURE:
<223> OTHER INFORMATION: synthetic construct

<400> SEQUENCE: 6
ugugcugacu cugaggaaca g                                                   21

<210> SEQ ID NO 7
<211> LENGTH: 21
<212> TYPE: DNA
<213> ORGANISM: Artificial Sequence
<220> FEATURE:
<223> OTHER INFORMATION: synthetic construct

<400> SEQUENCE: 7 cuguccuca gagucagcac a                                                    21

<210> SEQ ID NO 8
<211> LENGTH: 21
<212> TYPE: DNA
<213> ORGANISM: Artificial Sequence
<220> FEATURE:
<223> OTHER INFORMATION: synthetic construct

<400> SEQUENCE: 8
catacctcaa actgcatgat g                                                   21

<210> SEQ ID NO 9
<211> LENGTH: 21
<212> TYPE: DNA
<213> ORGANISM: Artificial Sequence
<220> FEATURE:
<223> OTHER INFORMATION: synthetic construct

<400> SEQUENCE: 9
cauaccucaa acugcaugau g                                                   21

<210> SEQ ID NO 10
<211> LENGTH: 21
<212> TYPE: DNA
<213> ORGANISM: Artificial Sequence
<220> FEATURE:
<223> OTHER INFORMATION: synthetic construct

<400> SEQUENCE: 10
caucaugcag uuugagguau g                                                   21

<210> SEQ ID NO 11
<211> LENGTH: 21
<212> TYPE: DNA
<213> ORGANISM: Artificial Sequence
<220> FEATURE:
<223> OTHER INFORMATION: synthetic construct

<400> SEQUENCE: 11
gcctgcagag ccggcggcct a                                                   21

<210> SEQ ID NO 12
<211> LENGTH: 21
<212> TYPE: DNA
<213> ORGANISM: Artificial Sequence
<220> FEATURE:
<223> OTHER INFORMATION: synthetic construct

<400> SEQUENCE: 12
```

-continued gccugcagag ccggcggccu a    21

<210> SEQ ID NO 13
<211> LENGTH: 21
<212> TYPE: DNA
<213> ORGANISM: Artificial Sequence
<220> FEATURE:
<223> OTHER INFORMATION: synthetic construct

<400> SEQUENCE: 13
uaggccgccg gcucugcagg c    21

<210> SEQ ID NO 14
<211> LENGTH: 21
<212> TYPE: DNA
<213> ORGANISM: Artificial Sequence
<220> FEATURE:
<223> OTHER INFORMATION: synthetic construct

<400> SEQUENCE: 14
acagagtttg tgacccacgc c    21

<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
acagaguuug ugacccacgc c    21

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
ggcguggguc acaaacucug u    21

<210> SEQ ID NO 17
<211> LENGTH: 21
<212> TYPE: DNA
<213> ORGANISM: Artificial Sequence
<220> FEATURE:
<223> OTHER INFORMATION: synthetic construct

<400> SEQUENCE: 17
tccctcatct actgtgtgca c    21

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
ucccucaucu acugugugca c    21

<210> SEQ ID NO 19
<211> LENGTH: 21
<212> TYPE: DNA
<213> ORGANISM: Artificial Sequence
<220> FEATURE:

```
<223> OTHER INFORMATION: synthetic construct

<400> SEQUENCE: 19
gugcacacag uagaugaggg a                                              21

<210> SEQ ID NO 20
<211> LENGTH: 5
<212> TYPE: DNA
<213> ORGANISM: Artificial Sequence
<220> FEATURE:
<223> OTHER INFORMATION: synthetic construct

<400> SEQUENCE: 20 ugugc                                                                5

<210> SEQ ID NO 21
<211> LENGTH: 7
<212> TYPE: DNA
<213> ORGANISM: Artificial Sequence
<220> FEATURE:
<223> OTHER INFORMATION: synthetic construct

<400> SEQUENCE: 21 gcacauc                                                              7

<210> SEQ ID NO 22
<211> LENGTH: 5
<212> TYPE: DNA
<213> ORGANISM: Artificial Sequence
<220> FEATURE:
<223> OTHER INFORMATION: synthetic construct

<400> SEQUENCE: 22 guugc                                                                5

<210> SEQ ID NO 23
<211> LENGTH: 7
<212> TYPE: DNA
<213> ORGANISM: Artificial Sequence
<220> FEATURE:
<223> OTHER INFORMATION: synthetic construct

<400> SEQUENCE: 23 ggaagag                                                              7

<210> SEQ ID NO 24
<211> LENGTH: 21
<212> TYPE: DNA
<213> ORGANISM: Artificial Sequence
<220> FEATURE:
<223> OTHER INFORMATION: synthetic construct

<400> SEQUENCE: 24
ugugcugacc cugaggaaca g                                              21

<210> SEQ ID NO 25
<211> LENGTH: 21
<212> TYPE: DNA
<213> ORGANISM: Artificial Sequence
<220> FEATURE:
<223> OTHER INFORMATION: synthetic construct

<400> SEQUENCE: 25
guuccucagg gucagcacau c                                              21

<210> SEQ ID NO 26
```

```
<211> LENGTH: 21
<212> TYPE: DNA
<213> ORGANISM: Artificial Sequence
<220> FEATURE:
<223> OTHER INFORMATION: synthetic construct

<400> SEQUENCE: 26
ugugcugacc cugaggaaaa g                                              21

<210> SEQ ID NO 27
<211> LENGTH: 21
<212> TYPE: DNA
<213> ORGANISM: Artificial Sequence
<220> FEATURE:
<223> OTHER INFORMATION: synthetic construct

<400> SEQUENCE: 27
uuuccucagg gucagcacau c                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic construct

<400> SEQUENCE: 28
ugugcugacc cugaggaaaa g                                              21

<210> SEQ ID NO 29
<211> LENGTH: 21
<212> TYPE: DNA
<213> ORGANISM: Artificial Sequence
<220> FEATURE:
<223> OTHER INFORMATION: synthetic construct

<400> SEQUENCE: 29
guuccucagg gucagcacau c                                              21

<210> SEQ ID NO 30
<211> LENGTH: 42
<212> TYPE: DNA
<213> ORGANISM: Artificial Sequence
<220> FEATURE:
<223> OTHER INFORMATION: synthetic construct

<400> SEQUENCE: 30
gcgtaatacg actcactata ggaacagtat gtctcagaca tc                       42

<210> SEQ ID NO 31
<211> LENGTH: 21
<212> TYPE: DNA
<213> ORGANISM: Artificial Sequence
<220> FEATURE:
<223> OTHER INFORMATION: synthetic construct

<400> SEQUENCE: 31
uucgaaguau uccgcguacg u                                              21

<210> SEQ ID NO 32
<211> LENGTH: 42
<212> TYPE: DNA
<213> ORGANISM: Artificial Sequence
<220> FEATURE:
<223> OTHER INFORMATION: synthetic construct

<400> SEQUENCE: 32
```

```
gcgtaatacg actcactata ggacaagcct aattagtgat gc                        42

<210> SEQ ID NO 33
<211> LENGTH: 21
<212> TYPE: DNA
<213> ORGANISM: Artificial Sequence
<220> FEATURE:
<223> OTHER INFORMATION: synthetic construct

<400> SEQUENCE: 33
gaacagtatg tctcagacat c                                               21
```

RNA INTERFERENCE FOR THE TREATMENT OF GAIN-OF-FUNCTION DISORDERS

RELATED APPLICATIONS

This patent application claims the benefit of U.S. Provisional Patent Application Ser. No. 60/502,678, entitled "RNA Interference for the Treatment of Gain-of-Function Disorders", filed Sep. 12, 2003. The entire contents of the above-referenced provisional patent applications are incorporated herein by this reference.

STATEMENT AS TO FEDERALLY SPONSORED RESEARCH

This invention was made with government support under grant No. NS038194 awarded by the National Institutes of Health. The government has certain rights in the invention.

BACKGROUND OF THE INVENTION

RNA interference (RNAi) is the mechanism of sequence-specific, post-transcriptional gene silencing initiated by double-stranded RNAs (dsRNA) homologous to the gene being suppressed. dsRNAs are processed by Dicer, a cellular ribonuclease III, to generate duplexes of about 21 nt with 3'-overhangs (small interfering RNA, siRNA) which mediate sequence-specific mRNA degradation. In mammalian cells siRNA molecules are capable of specifically silencing gene expression without induction of the unspecific interferon response pathway. Thus, siRNAs have become a new and powerful alternative to other genetic tools such as antisense oligonucleotides and ribozymes to analyze gene function. Moreover, siRNA's are being developed for therapeutic purposes with the aim of silencing disease genes in humans.

Trinucleotide repeat diseases comprise a recently recognized group of inherited disorders. The common genetic mutation is an increase in a series of a particular trinucleotide repeat. To date, the most frequent trinucleotide repeat is CAG, which codes for the amino acid glutamine. At least 9 CAG repeat diseases are known and there, are more than 20 varieties of these diseases, including Huntington's disease, Kennedy's disease and many spinocerebellar diseases. These disorders share a neurodegenerative component in the brain and/or spinal cord. Each disease has a specific pattern of neurodegeneration in the brain and most have an autosomal dominant inheritance.

The onset of the diseases generally occurs at 30 to 40 years of age, but in Huntington's disease CAG repeats in the huntingtin gene of >60 portend a juvenile onset.

Recent research by the instant inventors has shown that the genetic mutation (increase in length of CAG repeats from normal <36 in the huntingtin gene to >36 in disease) is associated with the synthesis of a mutant huntingtin protein, which has >36 polyglutamines (Aronin et al., 1995). It has also been shown that the protein forms cytoplasmic aggregates and nuclear inclusions (Difiglia et al., 1997) and associates with vesicles (Aronin et al., 1999). The precise pathogenic pathways are not known.

Huntington's disease (and by implication other trinucleotide repeat diseases) is believed to be caused, at least in part, by aberrant protein interactions, which cause impairment of critical neuronal processes, neuronal dysfunction and ultimately neuronal death (neurodegeneration in brain areas called the striatum and cortex). In the search for an effective treatment for these diseases, researchers in this field emphasized understanding the pathogenesis of the disease and initially sought to intercede at the level of the presumed aberrant protein interactions. However, there is no effective treatment for Huntington's disease or other trinucleotide repeat diseases. Moreover, it is now appreciated that multiple abnormal processes might be active in these types of disease.

SUMMARY OF THE INVENTION

The present invention relates to the methods for treating a variety of gain-of-function diseases. In particular, the invention provides methods for the selective destruction of mutant mRNAs transcribed from gain-of-function mutant genes, thus preventing production of the mutant proteins encoded by such genes. Other RNAi-based methods for destroying mutant genes have been proposed in which siRNAs are targeted to, for example, a point mutation occurring in a single allele in the mutant gene (e.g., the point mutation in the superoxide dismutase (SOD) gene associated with amyotrophic lateral sclerosis (ALS)). However, there is a key difference between ALS and trinucleotide repeat diseases, such as Huntington's disease. ALS has a point mutation in one allele as the genetic change whereas trinucleotide repeat diseases have an expanded CAG repeat region in one allele as the genetic change. Use of RNAi against the expanded CAG repeat region has potential complications. Over 80 normal genes with CAG repeat regions are known to exist in cells. Thus, siRNAs targeting these CAG repeats cannot be used without risking widespread destruction of normal CAG repeat-containing mRNAs. Likewise, targeting non-allele-specific sites would result in loss of both normal and mutant huntingtin causes neuronal dysfunction.

The methods of the invention utilize RNA interference technology (RNAi) against selected polymorphic regions (i.e., regions containing allele-specific or allelic polymorphisms) which are distinct from the site of mutation in the genes encoding mutant proteins. The methodologies of the instant invention are effective treatments for gain-of-function diseases resulting from deletion mutations, insertion mutations, point mutations, and the like, provided that the mutant gene encodes a protein having a function not normally associated with wild type protein.

In a preferred aspect, the methodologies of the instant invention provide an effective treatment for Huntington's disease (HD). The methodologies also provide effective treatments for other polyglutamine disorders and/or trinucleotide repeat disease, as described in detail herein.

Accordingly, in one aspect, the present invention provides a method of treating a subject having or at risk of having a disease characterized or caused by a gain of function mutant protein by administering to the subject an effective amount of an RNAi agent targeting an allelic polymorphism within a gene encoding a mutant protein e.g.,) huntingtin protein, such that sequence-specific interference of a gene occurs resulting in an effective treatment for the disease. In one embodiment, the mutant protein contains an expanded polyglutamine region. In another one embodiment, the gene encoding the mutant protein contains an expanded trinucleotide repeat region.

In a yet another embodiment, the method of the invention can be used to treat Huntington's disease and a variety of other diseases selected from the group consisting of spino-cerebellar ataxia type 1, spino-cerebellar ataxia type 2, spino-cerebellar ataxia type 3, spino-cerebellar ataxia type 6, spino-cerebellar ataxia type 7, spino-cerebellar ataxia type 8, spino-cerebellar ataxia type 12, myotonic dystrophy, spinal bulbar muscular disease and dentatoiubral-pallidoluysian atrophy.

The method of the invention uses RNAi agents homologous to an allelic polymorphism within the gene encoding, for example, a mutant huntingtin protein for the treatment of Huntington's disease. In a preferred embodiment, the RNAi agent targets allelic polymorphism selected from the group consisting of P1-P5. In a further preferred embodiment, the RNAi agent targets an allelic polymorphism selected from the group consisting of P6-P43.

In a further embodiment, the invention provides RNAi agents comprising of a first and second strand each containing 16-25 nucleotides. The first strand of the present invention is homologous to a region of a gene encoding a gain-of-function mutant protein, wherein the nucleotide sequence of the gain-of-function mutant protein comprises an allelic polymorphism. The second strand includes 16-25 nucleotides complementary to the first strand. The RNAi agent can also have a loop portion comprising 4-11, e.g., 4, 5, 6, 7, 8, 9, 10, 11, nucleotides that connects the two nucleotides sequences. In still other embodiments, the target region of the mRNA sequence is located in a 5' untranslated region (UTR) or a 3' UTR of the mRNA of a mutant protein.

In another embodiment, the invention provides an expression construct comprising an isolated nucleic acid that encodes a nucleic acid molecule with a first sequence of 16-25 nucleotides homologous to an allelic polymorphism within, for example, the gene encoding a mutant huntingtin protein. The expression construct can be for example, a viral vector, retroviral vector, expression cassette or plasmid. The expression construct can also have an RNA polymerase II promoter sequence or RNA Polymerase II promoter sequence, such as, U6 snRNA promoter of H1 promoter.

In yet other embodiments, the present invention provides host cells e.g.,) mammalian cells) comprising nucleic acid molecules and expression constructs of the present invention.

In still other embodiments, the present invention provides therapeutic compositions comprising the nucleic acid molecules of the invention and a pharmaceutically acceptable carrier.

Other features and advantages of the invention will be apparent from the following detailed description and claims.

BRIEF DESCRIPTION OF THE DRAWINGS

FIG. 1a-k: Human huntingtin gene, nucleotide sequence (SEQ ID NO:1)

FIG. 2a-b: Human huntingtin protein, amino acid sequence (SEQ ID NO:2)

FIG. 3: Sense (SEQ ID NO: 3) and antisense (SEQ ID NO: 4) of the huntingtin (htt) target RNA sequence FIG. 4: Thermodynamic analysis of siRNA strand 5' ends for the siRNA duplex (SEQ ID NOs: 20-23).

FIG. 5a-c: In vitro RNAi reactions programmed with siRNA targeting a polymorphism within the huntingtin (htt) mRNA. (a) Standard siRNA (SEQ ID NOs: 24-25). (b) siRNA improved by reducing the base-pairing strength of the 5' end of the anti-sense strand of the siRNA duplex (SEQ ID NOs: 26-27). (c) siRNA improved by reducing the unpairing the 5' end of the anti-sense strand of the siRNA duplex (SEQ ID NOs: 28-29).

FIG. 6a-b. RNAi of endogenous Htt protein in HeLa cells. (a) Immunoblot of human Htt protein. (b) Quantification of same.

DETAILED DESCRIPTION OF THE INVENTION

Figure 5C:
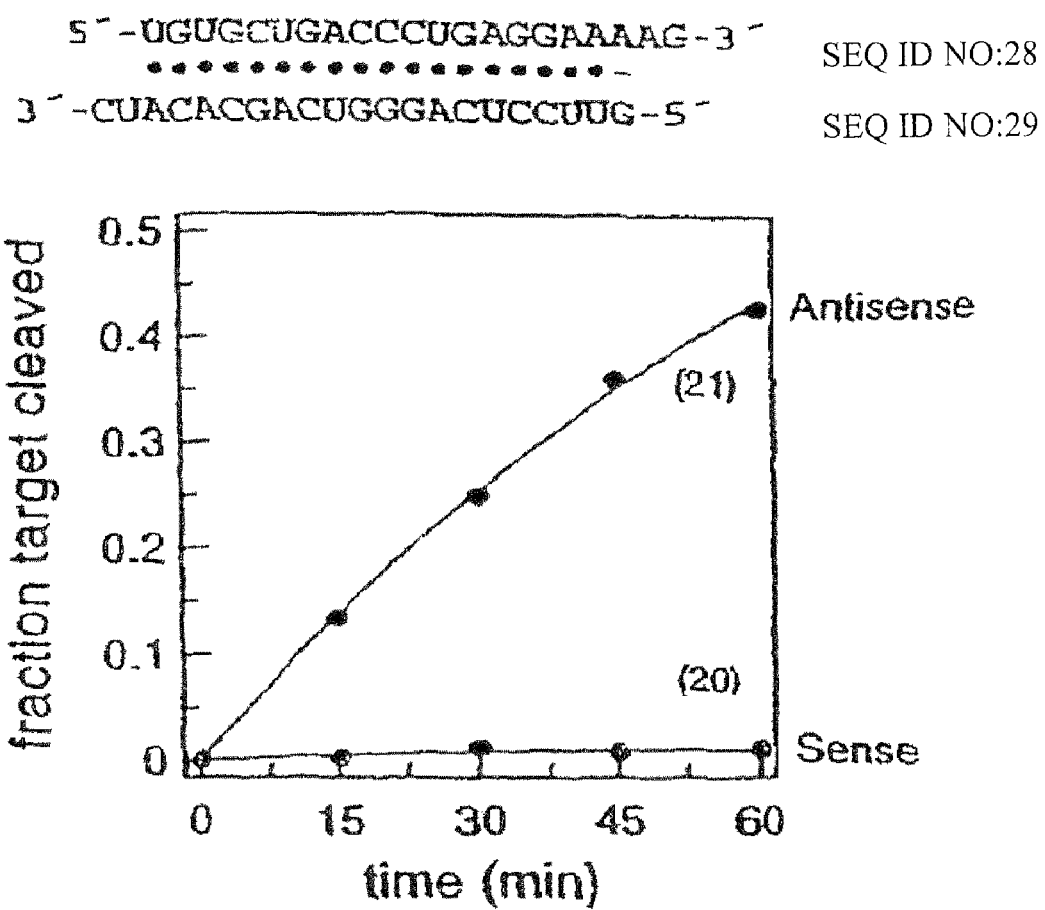

The present invention relates to methods and reagents for treating a variety of gain-of-function diseases. In one aspect, the invention relates to methods and reagents for treating a variety of diseases characterized by a mutation in one allele or copy of a gene, the mutation encoding a protein which is sufficient to contribute to or cause the disease. Preferably, the methods and reagents are used to treat diseases caused or characterized by a mutation that is inherited in an autosomal dominant fashion. In one embodiment, the methods and reagents are used for treating a variety of neurodegenerative disease caused by a gain-of-function mutation, e.g., polyglutamine disorders and/or trinucleotide repeat diseases, for example, Huntington's disease. In another embodiment, the methods and reagents are used for treating diseases caused by a gain-of-function in an oncogene, the mutated gene product being a gain-of-function mutant, e.g., cancers caused by a mutation in the ret oncogene (e.g., ret-1), for example, endocrine tumors, medullary thyroid tumors, parathyroid hormone tumors, multiple endocrine neoplasia type2, and the like. In another embodiment, the methods and reagents of the invention can be used to treat a variety of gastrointestinal cancers known to be caused by an autosomally-inherited, gain-of-function mutations.

The present invention utilizes RNA interference technology (RNAi) against allelic polymorphisms located within a gene encoding a gain-of-function mutant protein. RNAi destroys the corresponding mutant mRNA with nucleotide specificity and selectivity. RNA agents of the present invention are targeted to polymorphic regions of a mutant gene, resulting in cleavage of mutant mRNA. These RNA agents, through a series of protein-nucleotide interactions, function to cleave the mutant mRNAs. Cells destroy the cleaved mRNA, thus preventing synthesis of corresponding mutant protein e.g., the huntingtin protein.

Accordingly, in one aspect, the present invention provides a method of treating a subject having or at risk of having a disease characterized or caused by a gain of function mutant protein by administering to the subject an effective amount of an RNAi agent targeting an allelic polymorphism within a gene encoding a mutant protein e.g.,) huntingtin protein, such that sequence-specific interference of a gene occurs resulting in an effective treatment for the disease. In one embodiment, the mutant protein contains an expanded polyglutamine region. In another one embodiment, the gene encoding the mutant protein contains an expanded trinucleotide repeat region.

In a yet another embodiment, the method of the invention can be used to treat Huntington's disease and a variety of other diseases selected from the group consisting of spino-cerebellar ataxia type 1, spino-cerebellar ataxia type 2, spino-cerebellar ataxia type 3, spino-cerebellar ataxia type 6, spino-cerebellar ataxia type 7, spino-cerebellar ataxia type 8, spino-cerebellar ataxia type 12, myotonic dystrophy, spinal bulbar muscular disease and dentatoiubral-pallidoluysian atrophy.

The method of the invention uses RNAi agents homologous to an allelic polymorphism within the gene encoding, for example, a mutant huntingtin protein for the treatment of Huntington's disease. In a preferred embodiment, the RNAi agent targets allelic polymorphism selected from the group consisting of P1-P5. In a further preferred embodiment, the RNAi agent targets an allelic polymorphism selected from the group consisting of P6-P43.

In a further embodiment, the invention provides RNAi agents comprising of a first and second strand each containing 16-25 nucleotides. The first strand of the present invention is homologous to a region of a gene encoding a gain-of-function mutant protein, wherein the nucleotide sequence of the gain-of-function mutant protein comprises an allelic polymorphism. The second strand includes 16-25 nucleotides complementary to the first strand. The RNAi agent can also have a loop portion comprising 4-11, e.g., 4, 5, 6, 7, 8, 9, 10, 11, nucleotides that connect the two nucleotides sequences. In still other embodiments, the target region of the mRNA sequence is located in a 5' untranslated region (UTR) or a 3' UTR of the mRNA of a mutant protein.

In another embodiment, the invention provides an expression construct comprising an isolated nucleic acid that encodes a nucleic acid molecule with a first sequence of 16-25 nucleotides homologous to an allelic polymorphism within, for example, the gene encoding a mutant huntingtin protein. The expression construct can be for example, a viral vector, retroviral vector, expression cassette or plasmid. The expression construct can also have an RNA polymerase II promoter sequence or RNA Polymerase II promoter sequence, such as, U6 snRNA promoter of H1 promoter.

In yet other embodiments, the present invention provides host cells e.g.,) mammalian cells) comprising nucleic acid molecules and expression constructs of the present invention.

In still other embodiments, the present invention provides therapeutic compositions comprising the nucleic acid molecules of the invention and a pharmaceutically acceptable carrier.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH$_2$, NHR, NR$_2$, COOR, or OR, wherein R is substituted or unsubstituted C$_1$-C$_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11 (2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

The term "polymorphism" as used herein, refers to a variation (e.g., a deletion, insertion, or substitution) in a gene sequence that is identified or detected when the same gene sequence from different sources subjects (but from the same organism) are compared. For example, a polymorphism can be identified when the same gene sequence from different subjects (but from the same organism) are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. A variation in sequence between two alleles of the same gene within an organism is referred to herein as an "allelic polymorphism". The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene.

The term "polyglutamine domain," as used herein, refers to a segment or domain of a protein that consist of a consecutive glutamine residues linked to peptide bonds. In one embodiment the consecutive region includes at least 5 glutamine residues.

The term "expanded polyglutamine domain" or "expanded polyglutamine segment", as used herein, refers to a segment or domain of a protein that includes at least 35 consecutive glutamine residues linked by peptide bonds. Such expanded segments are found in subjects afflicted with a polyglutamine disorder, as described herein, whether or not the subject has shown to manifest symptoms.

The term "trinucleotide repeat" or "trinucleotide repeat region" as used herein, refers to a segment of a nucleic acid sequence e.g.,) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG, and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE Mental Retardation, Friedreich's ataxia and myotonic dystrophy. Preferred trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The term "polyglutamine disorder" as used herein, refers to any disease or disorder characterized by an expanded of a (CAG), repeats at the 5' end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also know as Machado-Joseph disease), and spino-cerebellar ataxia type 6, spino-cerebellar ataxia type 7 and dentatoiubral-pallidoluysian atrophy.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. Polyglutamine Disorders

Polyglutamine disorders are a class of disease or disorders characterized by a common genetic mutation. In particular, the disease or disorders are characterized by an expanded repeat of the trinucleotide CAG which gives rise, in the encoded protein, to an expanded stretch of glutamine residues. Polyglutamine disorders are similar in that the diseases are characterized by a progressive degeneration of nerve cells. Despite their similarities, polyglutamine disorders occur on different chromosomes and thus occur on entirely different segments of DNA. Examples of polyglutamine disorders include Huntington's disease, Dentatorubropallidoluysian Atrophy, Spinobulbar Muscular atrophy, Spinocerebellar Ataxia Type 1, Spinocerebellar Ataxia Type 2, Spinocerebellar Ataxia Type 3, Spinocerebellar Ataxia Type 6 and Spinocerebellar Ataxia Type 7 (Table 3).

TABLE 1

Polyglutamine disorders

| Disease | Gene | Locus | Protein | CAG repeat size Normal | Disease |
|---|---|---|---|---|---|
| Spinobulbar muscular atrophy (Kennedy disease) | AR | Xq13-21 | Androgen receptor (AR) | 9-36 | 38-62 |
| Huntington's disease | HD | 4p16.3 | Huntingtin | 6-35 | 36-121 |

TABLE 1-continued

Polyglutamine disorders

| Disease | Gene | Locus | Protein | CAG repeat size Normal | Disease |
|---|---|---|---|---|---|
| Dentatorubral-pallidoluysian atrophy (Haw-River syndrome) | DRPLA | 12p13.31 | Atrophin-1 | 6-35 | 49-88 |
| Spinocerebellar ataxia type 1 | SCA1 | 6p23 | Ataxin-1 | 6-44[a] | 39-82 |
| Spinocerebellar ataxia type 2 | SCA2 | 12q24.1 | Ataxin-2 | 15-31 | 36-63 |
| Spinocerebellar ataxia type 3 (Machado-Joseph disease) | SCA3 (MJD1) | 14q32.1 | Ataxin-3 | 12-40 | 55-84 |
| Spinocerebellar ataxia type 6 | SCA6 | 19p13 | $\alpha_{1A}$-voltage-dependent calcium channel subunit | 4-18 | 21-33 |
| Spinocerebellar ataxia type 7 | SCA7 | 13p12-13 | Ataxin-7 | 4-35 | 37-306 |

[a]Alleles with 21 or more repeats are interrupted by 1-3 CAT units; disease alleles contain pure CAG tracts.

Polyglutamine disorders of the invention are characterized by (e.g., domains having between about 30 to 35 glutamine residues, between about 35 to 40 glutamine residues, between about 40 to 45 glutamine residues and having about 45 or more glutamine residues. The polyglutamine domain typically contains consecutive glutamine residues (Q n>36).

II. Huntington Disease

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. CAG repeat varies in number from 8 to 35 in normal individuals (Kremer et al., 1994). The genetic mutation e.g.,) an increase in length of the CAG repeats from normal less than 36 in the huntingtin gene to greater than 36 in the disease is associated with the synthesis of a mutant huntingtin protein, which has greater than 36 polyglutamates (Aronin et al., 1995). In general, individuals with 36 or more CAG repeats will get Huntington's disease. Prototypic for as many as twenty other diseases with a lengthened CAG as the underlying mutation, Huntington's disease still has no effective therapy. A variety of interventions—such as interruption of apoptotic pathways, addition of reagents to boost mitochondrial efficiency, and blockade of NMDA receptors—have shown promise in cell cultures and mouse model of Huntington's disease. However, at best these approaches reveal a short prolongation of cell or animal survival.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Mutant huntingtin (protein) probably accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome—loss of mutant huntingtin.

III. Huntingtin Gene

The disease gene linked to Huntington's disease is termed Huntington or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein. The amino acid sequence of the human huntingtin protein is set forth in FIG. 2 (SEQ ID NO:2).

A consensus nucleotide sequence of the human huntingtin gene (cDNA) is set forth in FIG. 1 (SEQ ID NO:1). The coding region consists of nucleotides 316 to 9750 of SEQ ID NO:1. The two alternative polyadenylation signals are found at nucleotides 10326 to 10331 and nucleotides 13644 to 13649, respectively. The corresponding two polyadenylation sites are found at nucleotides 10348 and 13672, respectively. The first polyadenylation signal/site is that of the 10.3 kb transcript. The second polyadenylation signal/site is that of the 13.7 kb transcript, the predominant transcript in brain.

Five (5) polymorphisms in the human htt gene were identified as described in Example I. An additional 38 polymorphisms in the huntingtin gene sequence have been identified via SNP (single nucleotide polymorphism) analysis (see Table 3). The polymorphisms set forth in Tables 2 and 3 represent preferred sites to target via single-nucleotide-specific RNAi, as described herein.

TABLE 2

Polymorphic sites (P) in the htt gene of human cell lines.

| Cell line | P1 (2886) | P2 (4034) | P3 (6912) | P4 (7222) | P5 (7246) |
|---|---|---|---|---|---|
| GFP-Htt (9 kb construct) | C | G | A | T | C |
| HeLa | t | a | A | g | C |
| HEK 293T | t | a | G | g | t |
| HepG2 | t | a | G | g | t |
| FP-4 | t | a | g, A | g | t, C |

TABLE 3

Polymorphic sites (P) in the human htt gene identified by SNP analysis.

| | consensus | polymorphism | | db xref |
|---|---|---|---|---|
| complement 103 | G | A | P6 | dbSNP: 396875 |
| complement 432 | T | C | P7 | dbSNP: 473915 |
| complement 474 | C | A | P8 | dbSNP: 603765 |
| 1509 | T | C | P9 | dbSNP: 1065745 |
| complement 1857 | T | C | P10 | dbSNP: 2301367 |
| 3565 | G | C, A | P11, P12 | dbSNP: 1065746 |
| 3594 | T | G | P13 | dbSNP: 1143646 |

TABLE 3-continued

Polymorphic sites (P) in the human htt gene identified by SNP analysis.

| | consensus | polymorphism | | db xref |
|---|---|---|---|---|
| 3665 | G | C | P14 | dbSNP: 1065747 |
| complement 4122 | G | A | P15 | dbSNP: 363099 |
| complement 4985 | G | A | P16 | dbSNP: 363129 |
| complement 5480 | T | G | P17 | dbSNP: 363125 |
| 6658 | T | G | P18 | dbSNP: 1143648 |
| complement 6912 | T | C | P19 | dbSNP: 362336 |
| complement 7753 | G | A | P20 | dbSNP: 3025816 |
| complement 7849 | G | C | P21 | dbSNP: 3025814 |
| complement 8478 | T | C | P22 | dbSNP: 2276881 |
| 8574 | T | C | P23 | dbSNP: 2229985 |
| complement 9154 | C | A | P24 | dbSNP: 3025807 |
| 9498 | T | C | P25 | dbSNP: 2229987 |
| complement 9699 | G | A | P26 | dbSNP: 362308 |
| complement 9809 | G | A | P27 | dbSNP: 362307 |
| complement 10064 | T | C | P28 | dbSNP: 362306 |
| complement 10112 | G | C | P29 | dbSNP: 362268 |
| complement 10124 | G | C | P30 | dbSNP: 362305 |
| complement 10236 | T | G | P31 | dbSNP: 362304 |
| complement 10271 | G | A | P32 | dbSNP: 362303 |
| complement 10879 | G | A | P33 | dbSNP: 1557210 |
| complement 10883 | G | A | P34 | dbSNP: 362302 |
| complement 10971 | C | A | P35 | dbSNP: 3025805 |
| complement 11181 | G | A | P36 | dbSNP: 362267 |
| complement 11400 | C | A | P37 | dbSNP: 362301 |
| 11756 ... 11757 | G | — | P38 | dbSNP: 5855774 |
| 12658 | G | A | P39 | dbSNP: 2237008 |
| complement 12911 | T | C | P40 | dbSNP: 362300 |
| complement 13040 | G | A | P41 | dbSNP: 2530595 |
| 13482 | G | A | P42 | dbSNP: 1803770 |
| 13563 | G | A | P43 | dbSNP: 1803771 |

The present invention targets mutant huntingtin using RNA interference (Hutvagner et al., 2002). One strand of double-stranded RNA (siRNA) complements a polymorphic region within the mutant huntingtin mRNA. After introduction of siRNA into neurons, the siRNA partially unwinds, binds to polymorphic region within the huntingtin mRNA in a site-specific manner, and activates an mRNA nuclease. This nuclease cleaves the huntingtin mRNA, thereby halting translation of the mutant huntingtin. Cells rid themselves of partially digested mRNA, thus precluding translation, or cells digest partially translated proteins. Neurons survive on the wild-type huntingtin (from the normal allele); this approach prevents the ravages of mutant huntingtin by eliminating its production.

IV. siRNA Design siRNAs are designed as follows. First, a portion of the target gene (e.g., the htt gene) is selected that includes the polymorphism. Exemplary polymorphisms are selected from the 5' untranslated region of a target gene. Cleavage of mRNA at these sites should eliminate translation of corresponding mutant protein. Polymorphisms from other regions of the mutant gene are also suitable for targeting. A sense strand is designed based on the sequence of the selected portion. Preferably the portion (and corresponding sense strand) includes about 19 to 25 nucleotides, e.g., 19, 20, 21, 22, 23, 24 or 25 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably the RNAi agents of the invention do not elicit a PKR response (i.e., are of a sufficiently short length). However, longer RNAi agents may be useful, for example, in cell types incapable of generating a PRK response or in situations where the PKR response has been downregulated or dampened by alternative means.

The sense strand sequence is designed such that the polymorphism is essentially in the middle of the strand. For example, if a 21-nucleotide siRNA is chosen, the polymorphism is at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, the polymorphism is at, for example, nucleotide 7, 8, 9, 10, 11, 12, 13, 14, 15 or 16. For a 23-nucleotide siRNA, the polymorphism is at, for example, 7, 8, 9, 10, 11, 12, 13, 14, 15 or 16. For a 24-nucleotide siRNA, the polymorphism is at, for example, 9, 10, 11, 12, 13, 14 or 16. For a 25-nucleotide siRNA, the polymorphism is at, for example, 9, 10, 11, 12, 13, 14, 15, 16 or 17. Moving the polymorphism to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and include complementary nucleotides. In one embodiment, the strands are fully complementary, i.e., the strands are blunt-ended when aligned or annealed. In another embodiment, the strands comprise align or anneal such that 1-, 2- or 3-nucleotide overhangs are generated, i.e., the 3' end of the sense strand extends 1, 2 or 3 nucleotides further than the 5' end of the antisense strand and/or the 3' end of the antisense strand extends 1, 2 or 3 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Provisional patent application Nos. 60/475,386 entitled "Methods and Compositions for Controlling Efficacy of RNA Silencing" (filed Jun. 2, 2003) and 60/475,331 entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. Preferably, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). Preferably, the base pair is selected from the group consisting of an I:A, I:U and I:C. In yet another embodiment, the base pair strength is less due to at least one base pair comprising a modified nucleotide. In preferred embodiments, the modified nucleotide is selected from the group consisting of 2-amino-G, 2-amino-A, 2,6-diamino-G, and 2,6-diamino-A.

The design of siRNAs suitable for targeting the htt polymorphisms set forth in Table 2 is described in detail below

```
P1 DNA        TGTGCTGACTCTGAGGAACAG                                (SEQ ID NO: 5)

sense         UGUGCUGACUCUGAGGAACAG                                (SEQ ID NO: 6)

antisense     ACACGACUGAGACUCCUUGUC    (blunt-ends, 21-mer)(SEQ ID NO: 7)

(2-nt overhangs) see FIG. 5

P2 DNA        CATACCTCAAACTGCATGATG                                (SEQ ID NO: 8)

sense         CAUACCUCAAACUGCAUGAUG                                (SEQ ID NO: 9)

antisense     GUAUGGAGUUUGACGUACUAC    (blunt ends, 21-mer)(SEQ ID NO: 10)

P3 DNA        GCCTGCAGAGCCGGCGGCCTA                                (SEQ ID NO: 11)

sense         GCCUGCAGAGCCGGCGGCCUA                                (SEQ ID NO: 12)

antisense     CGGACGUCUCGGCCGCCGGAU    (blunt ends, 21-mer)(SEQ ID NO: 13)

P4 DNA        ACAGAGTTTGTGACCCACGCC                                (SEQ ID NO: 14)

sense         ACAGAGUUUGUGACCCACGCC                                (SEQ ID NO: 15)

antisense     UGUCUCAAACACUGGGUGCGG    (blunt ends, 21-mer)(SEQ ID NO: 16)

P5 DNA        TCCCTCATCTACTGTGTGCAC                                (SEQ ID NO: 17)

sense         UCCCUCAUCUACUGUGUGCAC                                (SEQ ID NO: 18)

antisense     AGGGAGUAGAUGACACACGUG    (blunt ends, 21 mer)(SEQ ID NO: 19)
``` siRNAs can be designed according to the above exemplary teachings for any other polymorphisms found in the htt gene. Moreover, the technology is applicable to targeting any other disease gene having associated polymorphisms, i.e., non-disease causing polymorphisms.

To validate the effectiveness by which siRNAs destroy mutant mRNAs (e.g., mutant huntingtin mRNA), the siRNA is incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA and use of wild-type huntingtin cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

While the instant invention primarily features targeting polymorphic regions in the target mutant gene (e.g., in mutant htt) distinct from the expanded CAG region mutation, the skilled artisan will appreciate that targeting the mutant region may have applicability as a therapeutic strategy in certain situations. Targeting the mutant region can be accomplished using siRNA that complements CAG in series. The siRNA$^{cag}$ would bind to mRNAs with CAG complementation, but might be expected to have greater opportunity to bind to an extended CAG series. Multiple siRNA$^{cag}$ would bind to the mutant huntingtin mRNA (as opposed to fewer for the wild type huntingtin mRNA); thus, the mutant huntingtin mRNA is more likely to be cleaved. Successful mRNA inactivation using this approach would also eliminate normal or wild-type huntingtin mRNA. Also inactivated, at least to some extent, could be other normal genes (approximately 70) which also have CAG repeats, where their mRNAs could interact with the siRNA. This approach would thus rely on an attrition strategy—more of the mutant huntingtin mRNA would be destroyed than wild type huntingtin mRNA or the other approximately 69 mRNAs that code for polyglutamines.

V. RNAi Agents

The present invention includes siRNA molecules designed, for example, as described above. The siRNA molecules of the invention can be chemically synthesized, or can be transcribed in vitro from a DNA template, or in vivo from e.g., shRNA, or, by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002. supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katahdin.cshl.org:9331/RNAi/docs/BseRI-BamHI_Strategy.pdf and katahdin.cshl.org:9331/RNAi/docs/Web_version_of PCR_strategy1.pdf.

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, supra).

Synthetic siRNAs can be delivered into cells by methods known in the art, including cationic liposome-transfection and electroporation. However, these exogenous siRNA generally show short term persistence of the silencing effect (4~5 days in cultured cells), which may be beneficial in only certain embodiments. To obtain longer term suppression of the target genes (i.e., mutant genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs; such as multiple regions of the gene encoding mutant htt, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals.

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles), Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25): 14428-33. Epub 2001 Nov. 27).

VI. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In a preferred aspect, the efficacy of an RNAi agent of the invention (e.g., an siRNA targeting a polymorphism in a mutant gene) is tested for its ability to specifically degrade mutant mRNA (e.g., mutant htt mRNA and/or the production of mutant huntingtin protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant huntingtin cDNA). Standard siRNA, modified siRNA or vectors able to produce siRNA from U-looped mRNA are co-transfected. Selective reduction in mutant mRNA (e.g., mutant huntingtin mRNA) and/or mutant protein (e.g., mutant huntingtin) is measured. Reduction of mutant mRNA or protein can be compared to levels of normal mRNA or protein. Exogenously-introduced normal mRNA or protein (or endogenous normal mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

VII. Methods of Treatment:

The present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In a preferred embodiment, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment", or "treating" as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for a polymorphism within the gene, such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

VIII. Pharmaceutical Compositions

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Unlike other types of autosomal dominant diseases, Huntington's disease does not contain a point mutation e.g.,) single nucleotide change. Therefore, the strategy to design siRNA directed against a point mutation in the disease allele cannot be implemented. Instead, the present invention directs designed siRNAs against polymorphisms in the Huntingtin gene, of which there are about 30 available in GenBank. The present invention also identifies the polymorphism in the Huntington disease allele which differs from the wild type allele, so that siRNA destroys only the disease mRNA and leaves intact the wild type (normal) allele mRNA. Thus, only the mutant Huntingtin protein is destroyed and the normal protein is intact.

Example I

Testing of RNAi Agents (e.g., siRNAs) Against Mutant htt in *Drosophila* Lysates A siRNA targeting position 2886 in the htt mRNA was designed as described supra. The sequence of the siRNA is depicted in FIG. 5a (SEQ ID NO:24 sense; 25 anti-sense). Synthetic RNA (Dharmacon) was deprotected according to the manufacturer's protocol. siRNA strands were annealed (Elbashir et al., 2001a).

Target RNAs were prepared as follows. Target RNAs were transcribed with recombinant, histidine-tagged, T7 RNA polymerase from PCR products as described (Nykänen et al., 2001; Hutvágner et al., 2002). PCR templates for htt sense and anti-sense were generated by amplifying 0.1 ng/ml (final concentration) plasmid template encoding htt cDNA using the following primer pairs: htt sense target, 5'-GCG TAA TAC GAC TCA CTA TAG GAA CAG TAT GTCTCA GAC ATC-3' (SEQ ID NO:30) and 5'-UUCG AAG UAU UCC GCG UAC GU-3' (SEQ ID NO:31); htt anti-sense target, 5'-GCG TAA TAC GAC TCA CTA TAG GAC AAG CCT AAT TAG TGA TGC-3' (SEQ ID NO:32) and 5'-GAA CAG TAT GTC TCA GAC ATC-3' (SEQ ID NO:33).

The siRNA was tested using an in vitro RNAi assay, featuring *Drosophila* embryo lysates. In vitro RNAi reactions and analysis was carried out as previously described (Tuschl et al., 1999; Zamore et al., 2000; Haley et al., 2003). Target RNAs were used at ~5 nM concentration so that reactions are mainly under single-turnover conditions. Target cleavage under these conditions is proportionate to siRNA concentration.

FIG. 5a shows the efficacy of the siRNA directed against position 2886 in the mutant htt. The data clearly demonstrate that the siRNA directs cleavage of the sense target to a greater degree than observed for the anti-sense target. However, it is noticed that this first-designed siRNA did not produce a very active molecule, at least in this in vitro assay. Thermodynamic analysis of the base pair strength at the two ends of the siRNA duplex indicated roughly equivalent base pair strengths. FIG. 4 depicts the thermodynamic analysis of siRNA sense (SEQ ID NO:20; 22 respectively) and anti-sense (SEQ ID NO:21; 23 respectively) strand 5' ends for the siRNA duplex in 5a. ΔG (kcal/mole) was calculated in 1 M NaCl at 37° C.

To improved the efficacy of the designed siRNA duplex, the 5 end of the sense strand or position 19 of the anti-sense strand of the htt siRNA tested in FIG. 5a was altered to produce siRNA duplexes in which the 5 end of the sense strand was either fully unpaired (FIG. 5c; SEQ ID NO: 28 sense; SEQ ID NO:29 anti-sense) or in an A:U base pair (FIG. 5b; SEQ ID NO:26 sense; SEQ ID NO:27 anti-sense). The unpairing the 5' end of an siRNA strand—the sense strand, in this case—causes that strand to function to the exclusion of the other strand. When the htt sense strand 5' end was present in an A:U base pair and the htt anti-sense strand 5' end was in a G:C pair, the sense strand dominated the reaction (FIG. 5b-c), but the htt anti-sense strand retained activity similar to that seen for the originally-designed siRNA.

Example II

RNAi Knockdown of Htt Protein in Cultured Cells

In a first experiment, siRNAs targeting a polymorphism in the htt mRNA (i.e., the polymorphism at position 2886 in the htt mRNA) were tested for their ability to down-regulate endogenous Htt protein in HeLa cells. HeLa cells were cultures and transfected as follows. HeLa cells were maintained at 37° C. in Dulbecco's modified Eagle's medium (DMEM, Invitrogen) supplemented with 10% fetal bovine serum (FBS), 100 unit/ml penicillin and 100 µg/ml streptomycin (Invitrogen). Cells were regularly passaged at sub-confluence and plated at 70% confluency 16 hours before transfection. Lipofectamine™ (Invitrogen)-mediated transient transfection of siRNAs were performed in duplicate 6-well plates (Falcon) as described for adherent cell lines by the manufacturer. A standard transfection mixture containing 100-150 nM siRNA and 9-10 µl Lipofectamine™ in 1 ml serum-reduced OPTI-MEM® (Invitrogen) was added to each well. Cells were incubated in transfection mixture at 37 C for 6 hours and further cultured in antibiotic-free DMEM. For Western blot analysis at various time intervals, the transfected cells were harvested, washed twice with phosphate buffered saline (PBS, Invitrogen), flash frozen in liquid nitrogen, and stored at −80° C. for analysis.

Three siRNAs were tested against a common target sequence in exon 1 and four siRNAs were tested for the position 2886 polymorphism. Western blot analysis was performed as follows. Cells treated with siRNA were harvested as described above and lysed in ice-cold reporter lysis buffer (Promega) containing protease inhibitor (complete, EDTA-free, 1 tablet/10 ml buffer, Roche Molecular Biochemicals). After clearing the resulting lysates by centrifugation, protein in clear lysates was quantified by Dc protein assay kit (Bio-Rad). Proteins in 60 µg of total cell lysate were resolved by 10% SDS-PAGE, transferred onto a polyvinylidene difluoride membrane (PVDF, Bio-Rad), and immuno-blotted with antibodies against CD80 (Santa Cruz). Protein content was visualized with a BM Chemiluminescence Blotting Kit (Roche Molecular Biochemicals). The blots were exposed to x-ray film (Kodak MR-1) for various times (30 s to 5 min). FIG. 6a depicts the results of the Western analysis. Tubulin served as the loading control. The data are quantified and normalized in FIG. 6b. Of the siRNAs tested, 28864, reproducibly showed enhanced efficacy in cultured HeLa cells (FIG. 6). This siRNA also reproducibly showed enhanced efficacy in vitro (not shown). GFP siRNA is a control siRNA that shares no sequence homology with htt mRNA.

siRNAs against polymorphic regions in the htt mRNA can likewise be tested in cells transfected with human htt cDNA or in cells transfected with htt reporter constructs. Lipofectamine™ (Invitrogen)-mediated transient cotransfections of cDNAs or reporter plasmids and siRNAs are performed as described supra. To test the ability of siRNAs to target htt reported constructs, RNAi was used to inhibit GFP-htt expression in cultured human Hela cell lines. Briefly, HeLa cells were transfected with GFP-htt siRNA duplex, targeting the GFP-htt mRNA sequence. To analyze RNAi effects against GFP-htt, lysates were prepared from siRNA duplex-treated cells at various times after transfection. Western blot experiments were carried out as described supra. Briefly, HeLa cells were harvested at various times post transfection, their protein content was resolved on 10% SDS-PAGE, transferred onto PVDF membranes, and immunoblotted with appropriate antibodies. Results of this study indicated that siRNA against GFP can eliminate expression of GFP-htt expression in Hela cells transfected with the GFP-htt gene. For studies targeting exogenously introduces htt, procedures are as described except that anti-Htt antibodies are used for immunoblotting.

RNAi can be used to inhibit htt expression in cultured neuronal cells as well. Exemplary cells include PC12 (Scheitzer et al., Thompson et al.) and NT-3293 (Tagle et al.) cell lines as previously described. Additional exemplary cells include stably-transfected cells, e.g. neuronal cells or neuronally-derived cells. PC12 cell lines expressing exon 1 of the human huntingtin gene (Htt) can be used although expression of exon 1 reduces cell survival. GFP-Htt PC12 cells having an inducible GFP-Htt gene can also be used to test or validate siRNA efficacy.

Example III

Htt siRNA Delivery in an In Vivo Setting

R6/2 mice models (expressing the R6/2 human htt cDNA product) are an accepted animal model to study the effectiveness of siRNA delivery in an in vivo setting. Genetically engineered R6/2 mice were used to test the effectiveness of siRNA at the 5' terminus of huntingtin mRNA. Htt siRNA was injected into the striatum of R6/2 mice through an Alzet pump. Mice were treated for 14 days with the siRNA/Alzet pump delivery system.

Results of this study indicated that two mice receiving the siRNA with Trans-IT TKO (Mirus) as either a 20 or 200 nM solution at 0.25 µl/hour showed no deterioration of motor impairment from day 67 to day 74. Generally, these R6/2 are expected to have a continued reduction in rotarod beyond day 60.

REFERENCES

Aronin et al., Neuron, November; 15(5):1193-201 (1995)
Aronin et al., Phil Trans Royal Society, June 29; 354 (1386): 995-1003 (1999)
Bagella et al., J. Cell. Physiol. 177:206-213 (1998)
Brummelkamp et al., Science 296:550-553 (2002)
Calegari et al., Proc. Natl. Acad. Sci. USA 99(22):14236-40 (2002)
Difiglia et al., Science, September 26; 277(5334):1990-3 (1997)
Elbashir et al., Genes Dev 15, 188-200 (2001a)
Haley et al., Methods 30, 330-336 (2003)
Hutvágner and Zamore, Science 297, 2056-2060 (2002)
Jacque et al., (2002)
Kremer et al., (1994)
Laforet et al., J. Neurosci., December 1; 21(23):9112-23 (2001)
Lee et al., EMBO J. 21: 4663-4670. (2002)
Lewis et al., Nature Genetics 32:107-108 (2002)
Lin et al., (1993)
Liu et al., (1999)
McCaffrey et al., Gene Ther. 2002 December; 9(23): 1563 (2002)
McManus et al., RNA 8, 842-850 (2002)
Miyagishi et al., Nature Biotechnol. 20:497-500 (2002)
Nykänen et al., Cell 107, 309-321 (2001)
Paddison et al., Genes Dev 16, 948-958. (2002)
Paul et al., Nat Biotechnol 20, 505-508 (2002)

Scheitzer et al.
Sui et al., Proc Natl Acad Sci USA 99, 5515-5520 (2002)
Tagle et al.
Thompson et al.
Tuschl, T., Nat. Biotechnol. 2002 May; 20(5):446-8 (2002)
Tuschl et al., Genes Dev 13, 3191-3197 (1999)
Xia et al., (2002)
Yohrling G. J. et al., Mol Cell Neurosci. May; 23(1):28-38 (2003)
Yu et al., Proc Natl Acad Sci USA 99, 6047-6052 (2002)
Zamore et al., Cell 101, 25-33 (2000)
Zamore et al., Nature Medicine, volume 9 Number 3 pp 266-267 (2003)
Zeng et al., (2002)

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having Huntington's disease caused by a mutation within the htt gene encoding a gain-of-function mutant huntingtin protein, comprising: administration to the subject of an effective amount of siRNA or shRNA targeting a non-disease causing allelic polymorphism located at a site distinct from the disease causing mutation within the htt gene encoding the mutant huntingtin protein, such that sequence-specific interference of the htt gene occurs; thereby treating the disease in the subject, wherein the effective amount is an amount effective to inhibit the expression or activity of the mutant huntingtin protein, and wherein the administration is direct administration of the siRNA or shRNA to neuronal cells or tissue.

2. The method of claim 1, wherein the siRNA or shRNA targets a polymorphism selected from the group consisting of P1-P5, wherein P1 corresponds to position 2886 of the htt nucleic acid sequence set forth in SEQ ID NO:1, P2 corresponds to position 4034 of the htt nucleic acid sequence set forth in SEQ ID NO:1, P3 corresponds to position 6912 of the htt nucleic acid sequence set forth in SEQ ID NO:1, P4 corresponds to position 7222 of the htt nucleic acid sequence set forth in SEQ ID NO:1, and P5 corresponds to position 7246 of the htt nucleic acid sequence set forth in SEQ ID NO:1.

3. The method of claim 1, wherein the siRNA or shRNA targets a polymorphism selected from the group consisting of P6-P43.

4. The method of claim 1, wherein the siRNA comprises a first strand comprising about 16-25 nucleotides homologous to a region of the gene comprising the polymorphism and a second strand comprising about 16-25 nucleotides complementary to the first strand.

5. A method of silencing a target mRNA transcribed from an htt gene comprising a mutation encoding a gain-of-function mutant huntingtin protein in a cell, comprising administering to the cell an effective amount of a siRNA or shRNA targeting a non-disease causing allelic polymorphism located at a site distinct from the disease causing mutation within the target htt mRNA, such that sequence-specific interference of said target htt mRNA occurs, wherein the effective amount is an amount effective to inhibit the expression or activity of the mutant huntingtin protein.

6. The method of claim 5, wherein the siRNA or shRNA targets a polymorphism selected from the group consisting of P1-P5, wherein P1 corresponds to position 2886 of the htt nucleic acid sequence set forth in SEQ ID NO:1, P2 corresponds to position 4034 of the htt nucleic acid sequence set forth in SEQ ID NO:1, P3 corresponds to position 6912 of the htt nucleic acid sequence set forth in SEQ ID NO:1, P4 corresponds to position 7222 of the htt nucleic acid sequence set forth in SEQ ID NO:1, and P5 corresponds to position 7246 of the htt nucleic acid sequence set forth in SEQ ID NO:1.

7. The method of claim 5, wherein the siRNA or shRNA targets a polymorphism selected from the group consisting of P6-P43.

8. The method of claim 5, wherein the siRNA or shRNA comprises a first strand comprising about 16-25 nucleotides homologous to a region of the target mRNA comprising the polymorphism and a second strand comprising about 16-25 nucleotides complementary to the first strand.

9. The method of claims 1 or 5, wherein the siRNA or shRNA does not target a trinucleotide repeat region.

\* \* \* \* \*